US008871686B2

(12) United States Patent
Ghadessy et al.

(10) Patent No.: US 8,871,686 B2
(45) Date of Patent: Oct. 28, 2014

(54) METHODS OF IDENTIFYING A PAIR OF BINDING PARTNERS

(75) Inventors: John Farid Ghadessy, Singapore (SG); Saurabh Nirantar, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 13/382,910

(22) PCT Filed: Jul. 7, 2010

(86) PCT No.: PCT/SG2010/000258
§ 371 (c)(1),
(2), (4) Date: Apr. 23, 2012

(87) PCT Pub. No.: WO2011/005221
PCT Pub. Date: Jan. 13, 2011

(65) Prior Publication Data
US 2013/0143749 A1    Jun. 6, 2013

Related U.S. Application Data

(60) Provisional application No. 61/223,524, filed on Jul. 7, 2009.

(51) Int. Cl.
*C12Q 1/68* (2006.01)
*G01N 33/53* (2006.01)
*C12N 15/66* (2006.01)
*G03C 1/015* (2006.01)

(52) U.S. Cl.
USPC .............................................. 506/7

(58) Field of Classification Search
CPC .................................. G01N 33/6845
USPC .............................................. 506/7
See application file for complete search history.

(56) References Cited

U.S. PATENT DOCUMENTS

| 6,270,964 B1 | 8/2001 | Michnick et al. |
| 7,323,313 B2 | 1/2008 | Pruitt et al. |
| 2007/0105117 A1 | 5/2007 | Heinis |

FOREIGN PATENT DOCUMENTS

| WO | WO 96/23879 A1 | 8/1996 |
| WO | WO 01/04144 A2 | 1/2001 |

(Continued)

OTHER PUBLICATIONS

Wilson et al., Nature Methods, Dec. 2004, vol. 1, No. 3, pp. 255-262.*

(Continued)

*Primary Examiner* — Larry Riggs
*Assistant Examiner* — Karla Dines
(74) *Attorney, Agent, or Firm* — Blakely, Sokoloff, Taylor & Zafman LLP

(57) ABSTRACT

The invention relates to methods of identifying a binding partner of a target molecule within a plurality of analyte molecules, including a plurality of peptides and/or proteins. The target molecule is physically combined with a target labeling nucleic acid molecule. Each member of the plurality of analyte molecules is physically linked to an analyte labeling nucleic acid molecule, each analyte labeling nucleic acid molecule comprising a selected nucleotide sequence. This specific nucleotide sequence may include a sequence encoding a peptide/protein combined therewith. The target molecule is contacted with the analyte molecules and a complex between the target molecule and an analyte molecule forms. The mixture is subdivided into compartments. The target labeling nucleic acid molecule and the analyte labeling nucleic acid molecule are linked and the plurality of compartments allowed to disintegrate. The linked nucleic acid molecule is retrieved and the sequence determined.

31 Claims, 17 Drawing Sheets

(56) References Cited

FOREIGN PATENT DOCUMENTS

| WO | WO 03/029462 A1 | 4/2003 |
|---|---|---|
| WO | WO 2005/019254 A1 | 3/2005 |
| WO | WO 2005/019255 A1 | 3/2005 |
| WO | WO 2005/019256 A2 | 3/2005 |
| WO | WO 2005/049787 A2 | 6/2005 |
| WO | WO 2009/011808 A1 | 1/2009 |

OTHER PUBLICATIONS

PCT International Search Report for PCT Counterpart Application No. PCT/SG2010/000258 containing Communication relating to the Results of the International Search Report, 5 pgs., (Aug. 23, 2010).

PCT Written Opinion of the International Searching Authority for PCT Counterpart Application No. PCT/SG2010/000258, 6 pgs., (Aug. 23, 2010).

PCT Notification concerning Transmittal of International Preliminary Report on Patentability (Chapter I of the Patent Cooperation Treaty) for PCT Counterpart Application No. PCT/SG2010/000258, 8 pgs., (Jan. 19, 2012).

Benhar, Itai, "Biotechnological Applications of Phage and Cell Display", Biotechnology Advances, vol. 19, pp. 1-33, (2001).

Beste, Gerald, et al., "Small Antibody-Like Proteins with Prescribed Ligand Specificities Derived from the Lipocalin Fold", Proc. Natl. Acad. Sci. USA, vol. 96, pp. 1898-1903, (Mar. 1999).

Bowley, Diana R., et al., "Libraries against Libraries for Combinatorial Selection of Replicating Antigen-Antibody Pairs", PNAS, vol. 106, No. 5. pp. 1380-1385, (Feb. 3, 2009).

Cañizares, Pablo, et al., "Coagulation and Electrocoagulation of Oil-in-Water Emulsions", Journal of Hazardous Materials, vol. 151, No. 1, pp. 44-51, (Feb. 28, 2008).

Charles, I., et al., "Synthesis of Neomycin-DNA/Peptide Nucleic Acid Conjugates", Journal of Carbohydrate Chemistry, vol. 24, pp. 145-160, (2005).

Cohen, Helen M., et al., "Altering the Sequence Specificity of *Hae*III methyltransferase by Directed Evolution using in vitro Compartmentalization", Protein Engineering, Design & Selection, vol. 17, No. 1, pp. 3-11, (2004).

Di Lallo, G., et al , "Use of a Two-Hybrid Assay to Study the Assembly of a Complex Multicomponent Protein Machinery: Bacterial Septosome Differentiation", Microbiology, vol. 149, pp. 3353-3359, (2003).

Doi, Nobuhide, et al., "Stable: Protein-DNA Fusion System for Screening of Combinatorial Protein Libraries In Vitro", FEBS Letters, vol. 457, pp. 227-230, (1999).

Fu, Ling, et al., "Detection of Protein-Protein Interactions among Lens Crystallins in a Mammalian Two-Hybrid System Assay", The Journal of Biological Chemistry, vol. 277, No. 6, pp. 4255-4260, (Feb. 8, 2002).

Gavin, Anne-Claude, et al., "Functional Organization of the Yeast Proteome by Systematic Analysis of Protein Complexes", Nature, vol. 415, pp. 141-147, (Jan. 10, 2002).

Ghadessy, Farid J., et al., "Directed Evolution of Polymerase Function by Compartmentalized Self-Replication", PNAS, vol. 98, No. 8, pp. 4552-4557, (Apr. 10, 2001).

Giot, L., et al., "A Protein Interaction Map of *Drosophila melanogaster*", Science, vol. 302, pp. 1727-1736, (Dec. 5, 2003).

Gogoi, Khirud, et al., "A Versatile Method for the Preparation of Conjugates of Peptides with DNA/PNA/Analog by Employing Chemo-Selective Click Reaction in Water", Nucleic Acids Research, vol. 35, No. 21, e139, 7 pgs., (2007).

Greaves, Tamar L., et al., "Protic Ionic Liquids: Properties and Applications", Chem. Rev., vol. 108, pp. 206-237, (2008).

Griffiths, Andrew D., et al., "Miniaturising the Laboratory in Emulsion Droplets", Trends in Biotechnology, vol. 24, No. 9, pp. 395-402, (2006).

Grigoriev, Andrei, "On the No. Of Protein-Protein Interactions in the Yeast Proteome", Nucleic Acids Research, vol. 31, No. 14, pp. 4157-4161, (2003).

Hart, G Traver, et al., "How Complete are current Yeast and Human Protein-Interaction Networks?", Genome Biology, vol. 7, No. 11, pp. 120-120.9, (2006).

Hastie, Alex R., et al., "Yeast Two-Hybrid Interaction Partner Screening through in vivo Cre-mediated Binary Interaction Tag Generation", Nucleic Acids Research, vol. 35, No. 21, e141, 8 pgs., (2007).

He, Mingyue, et al., "Ribosome Display: Cell-Free Protein Display Technology", Briefings in Functional Genomics and Proteomics, vol. 1, No. 2, pp. 204-212, (Jul. 2002).

He, Mingyue, et al., "Eukaryotic Ribosome Display with in situ DNA Recovery", Nature Methods, vol. 4, No. 3, pp. 281-288, (Mar. 2007).

Ho, Yuen, et al., "Systematic Identification of Protein Complexes in *Saccharomyces cerevisiae* by Mass Spectrometry", Nature, vol. 415, pp. 180-183, (Jan. 10, 2002).

Holt, Lucy J., et al., "Domain Antibodies: Proteins for Therapy", Trends in Biotechnology. vol. 21, No. 11, pp. 484-490, (Nov. 2003).

Horisawa, Kenichi, et al., "3'-Untranslated Region of *doublecortin* mRNA is a Binding Target of the Musashi1 RNA-Binding Protein", FEBS Letters, vol. 583, pp. 2429-2434, (2009).

Huang, Hailiang, et al., "Where Have All the Interactions Gone? Estimating the Coverage of Two-Hybrid Protein Interaction Maps", PLoS Computational Biology, vol. 3, No. 11, e214, pp. 2155-2174, (Nov. 2007).

Iliades, Peter, et al., "Triabodies: Single Chain Fv Fragments without a Linker form Trivalent Trimers", FEBS Letters, vol. 409, pp. 437-441, (1997).

Ito, Takashi, et al., "A Comprehensive Two-Hybrid Analysis to Explore the Yeast Protein Interactome", PNAS, vol. 98, No. 8, pp. 4569-4574, (Apr. 10, 2001).

Jung, Sabine, et al., "Selectively Infective Phage (SIP) Technology: Scope and Limitations", Journal of Immunological Methods, vol. 231, pp. 93-104, (1999).

Karimova, Gouzel, et al., "A Bacterial Two-Hybrid System based on a Reconstituted Signal Transduction Pathway", Proc. Natl. Acad. Sci. USA, vol. 95, pp. 5752-5756. (May 1998).

Karimova, Gouzel, et al., "Interaction Network among *Escherichia coli* Membrane Proteins Involved in Cell Division as Revealed by Bacterial Two-Hybrid Analysis", Journal of Bacteriology, vol. 187, No. 7, pp. 2233-2243, (Apr. 2005).

Krogan, Nevan J., et al., "Global Landscape of Protein Complexes in the Yeast *Saccharomyces cerevisiae*", Nature, vol. 440, pp. 637-643, (Mar. 30, 2006).

Kwon, Yong-Uk, et al., "Quantitative Evaluation of the Relative Cell Permeability of Peptoids and Peptides", J. Am. Chem. Soc., vol. 129, No. 6, pp. 1508-1509, (Feb. 14, 2007).

Lacount, Douglas J., et al., "A Protein Interaction Network of the Malaria Parasite *Plasmodium falciparum*", Nature, vol. 438, pp. 103-107, (Nov. 3, 2005).

Li, Hanying, et al., "Single-Chain Antibodies against DNA Aptamers for Use as Adapter Molecules on DNA Tile Arrays in Nanoscale Materials Organization", Org. Biomol. Chem., vol. 4, pp. 3420-3426, (2006).

Li, Siming, et al., "A Map of the Interactome Network of the Metazoan *C. elegans*", Science, vol. 303. No. 5657, pp. 540-543, (Jan. 23, 2004).

Liu, Bin, et al., "Characterization of TectoRNA Assembly with Cationic Conjugated Polymers", J. Am. Chem. Soc., vol. 126, pp. 4076-4077, (2004).

Luo, Ying, et al., "Mammalian Two-Hybrid System: A Complementary Approach to the Yeast Two-Hybrid System", BioTechniques, vol. 22, No. 2, pp. 350-352, (Feb. 1997).

Maggi, Silvia, et al., "Division Protein Interaction Web: Identification of a Phylogenetically Conserved Common Interactome between *Streptococcus pneumoniae* and *Escherichia coli*", Microbiology, vol. 154, pp. 3042-3052, (2008).

Marbouty, Martial, et al., "Characterization of the *Synechocystis* Strain PCC 6803 Penicillin-Binding Protein and Cytokinetic Proteins FtsQ and FtsW and Their Network of Interactions with ZipN", Journal of Bacteriology, vol. 191, No. 16, pp. 5123-5133, (Aug. 2009).

Moreau, Valérie, et al., "Zip Nucleic Acids: New High Affinity Oligonucleotides as Potent Primers for PCR and Reverse Transcription", Nucleic Acids Research, vol. 37, No. 19, e130, 14 pgs., (2009).

(56) References Cited

OTHER PUBLICATIONS

Mosavi, Leila K., et al., "The Ankyrin Repeat as Molecular Architecture for Protein Recognition", Protein Science, vol. 13, pp. 1435-1448, (2004).

Nakano, Michihiko, et al., "Single-Molecule Reverse Transcription Polymerase Chain Reaction using Water-in-Oil Emulsion", Journal of Bioscience and Bioengineering, vol. 99, No. 3, pp. 293-295, (2005).

Olejnik, Jerzy, et al., "Photocleavable Peptide-DNA Conjugates: Synthesis and Applications to DNA Analysis using MALDI-MS", Nucleic Acids Research, vol. 27, No. 23, pp. 4626-4631, (1999).

Parrish, Jodi R., et al., "A Proteome-Wide Protein Interaction Map for *Campylobacter jejuni*", Genome Biology, vol. 8, No. 7, pp. R130-R130.19, (2007).

Pelletier, Joelle N., et al., "Oligomerization Domain-Directed Reassembly of Active Dihydrofolate Reductase from Rationally Designed Fragments", Proc. Natl. Acad. Sci. USA, vol. 95, pp. 12141-12146, (Oct. 1998).

Rain, Jean-Christophe, et al., "The Protein-Protein Interaction Map of *Helicobacter pylori*", Nature, vol. 409, pp. 211-215, (Jan. 11, 2001).

Ratushny, Vladimir, et al., "Resolving the Network of Cell Signaling Pathways using the Evolving Yeast Two-Hybrid System", BioTechniques, vol. 44, No. 5, pp. 655-662, (2008).

Rothe, Achim, et al., "In vitro Display Technologies Reveal Novel Biopharmaceutics", The FASEB Journal, vol. 20, pp. 1599-1610, (Aug. 2006).

Rothe, Achim, et al., "Novel Biotechnology in Emulsions using In Vitro Compartmentalization", Trends in Biotechnology, vol. 24, No. 12, pp. 587-592, (2006).

Schaffitzel, Christiane, et al., "Ribosome Display: An in vitro Method for Selection and Evolution of Antibodies from Libraries", Journal of Immunological Methods, vol. 231, pp. 119-135, (1999).

Secco, Paola, et al., "Antibody Library Selection by the β-lactamase Protein Fragment Complementation Assay", Protein Engineering, Design & Selection, vol. 22, No. 3, pp. 149-158, (2009).

Sergeeva, Anna, et al., "Display Technologies: Application for the Discovery of Drug and Gene Delivery Agents", Adv. Drug Deliv. Rev., vol. 58, No. 15, pp. 1622-1654, (Dec. 30, 2006).

Silverman, Joshua, et al., "Multivalent Avimer Proteins Evolved by Exon Shuffling of a Family of Human Receptor Domains", Nature Biotechnology, vol. 23, No. 12, pp. 1556-1561, (Dec. 2005).

Skerra, Arne, "Engineered Protein Scaffolds for Molecular Recognition", Journal of Molecular Recognition, vol. 13, pp. 167-187, (2000).

Stelzl, Ulrich, et al., "A Human Protein-Protein Interaction Network: A Resource for Annotating the Proteome", Cell, vol. 122, pp. 957-968, (Sep. 23, 2005).

Tavvfik, Dan S., et al., "Man-made Cell-like Compartments for Molecular Evolution", Nature Biotechnology, vol. 16, pp. 652-656, (Jul. 1998).

Terradot, Laurent, et al., "Biochemical Characterization of Protein Complexes from the *Helicobacter pylori* Protein Interaction Map", Molecular & Cellular Proteomics, vol. 3, No. 8, pp. 809-819, (2004).

Titz, Björn, et al., "The Binary Protein Interactome of *Treponema pallidum*—The Syphilis Spirochete". PLoS ONE, vol. 3, No. 5, e2292, pp. 1-11, (May 2008).

Uetz, Peter, et al., "Herpesviral Protein Networks and Their Interaction with the Human Proteome", Science, vol. 311, pp. 239-242, (Jan. 13, 2006).

Uetz, Peter, et al., "A Comprehensive Analysis of Protein-Protein Interactions in *Saccharomyces cerevisiae*", Nature, vol. 403, pp. 623-627, (Feb. 10, 2000).

Yamaguchi, Junichi, et al., "cDNA Display: A Novel Screening Method for Functional Disulfide-Rich Peptides by Solid-Phase Synthesis and Stabilization of mRNA-Protein Fusions", Nucleic Acids Research, vol. 37, No, 16, e108, 13 pgs., (2009).

Yan, Xianghua, et al., "Ribosome-Display Technology: Applications for Directed Evolution of Functional Proteins", Drug Discovery Today, vol. 11, Nos. 19/20, pp. 911-916, (Oct. 2006).

Zatsepin, Timofei S., et al., "Synthesis of DNA Conjugates by Solid-Phase Fragment Condensation via Aldehyde-Nucleophile Coupling", Tetrahedron Letters, vol. 46, pp. 3191-3195, (2005).

Zahnd, Christian, et al., "Ribosome Display: Selecting and Evolving Proteins In Vitro that Specifically Bind to a Target", Nature Methods, vol. 4, No. 3, pp. 269-279, (Mar. 2007).

Zhu, Heng, et al., "Global Analysis of Protein Activities using Proteome Chips", Science, vol. 293, pp. 2101-2105, (Sep. 14, 2001).

Extended European Search Report for EP Counterpart Patent Application No. 10797427.1, 12 pgs. (Nov. 6, 2012).

Saurabh R. Nirantar, et al., "Compartmentalized linkage of genes encoding interacting protein pairs," Proteomic 2011, vol. 11, pp. 1335-1339 (2011).

* cited by examiner

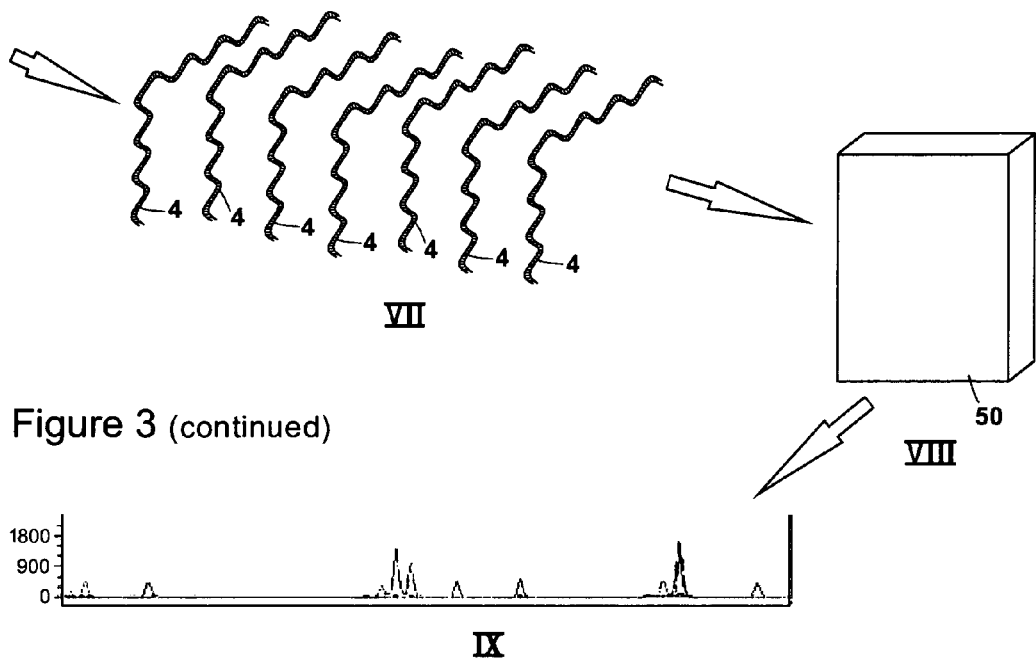
Figure 3 (continued)
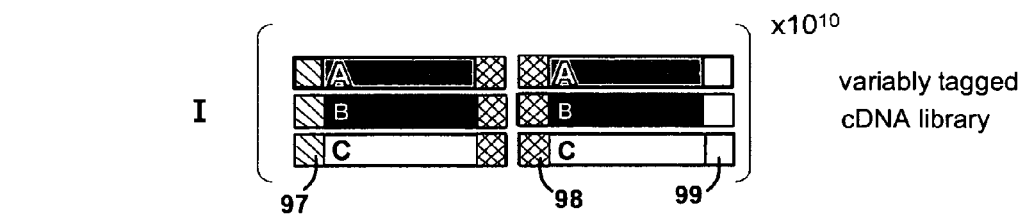
Figure 4
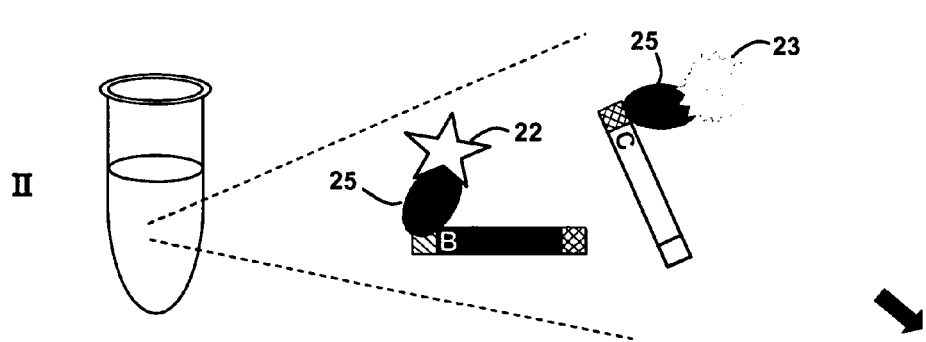

Figure 6A
yeast two hybrid system
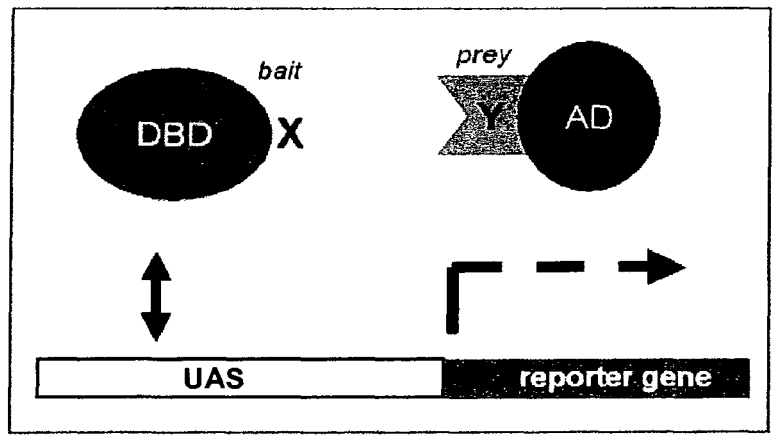
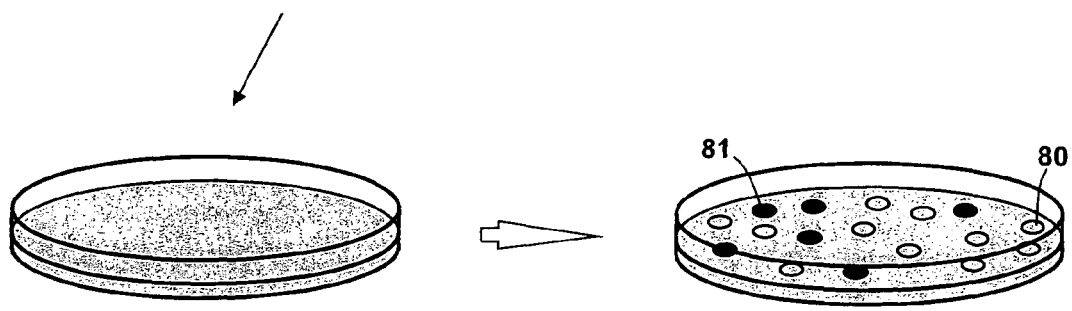
Figure 6B
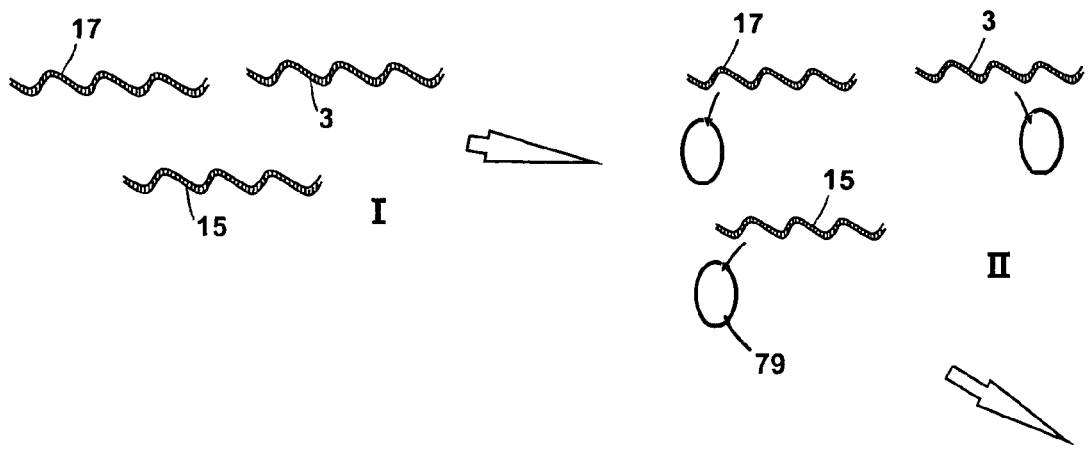

Figure 6B (continued)
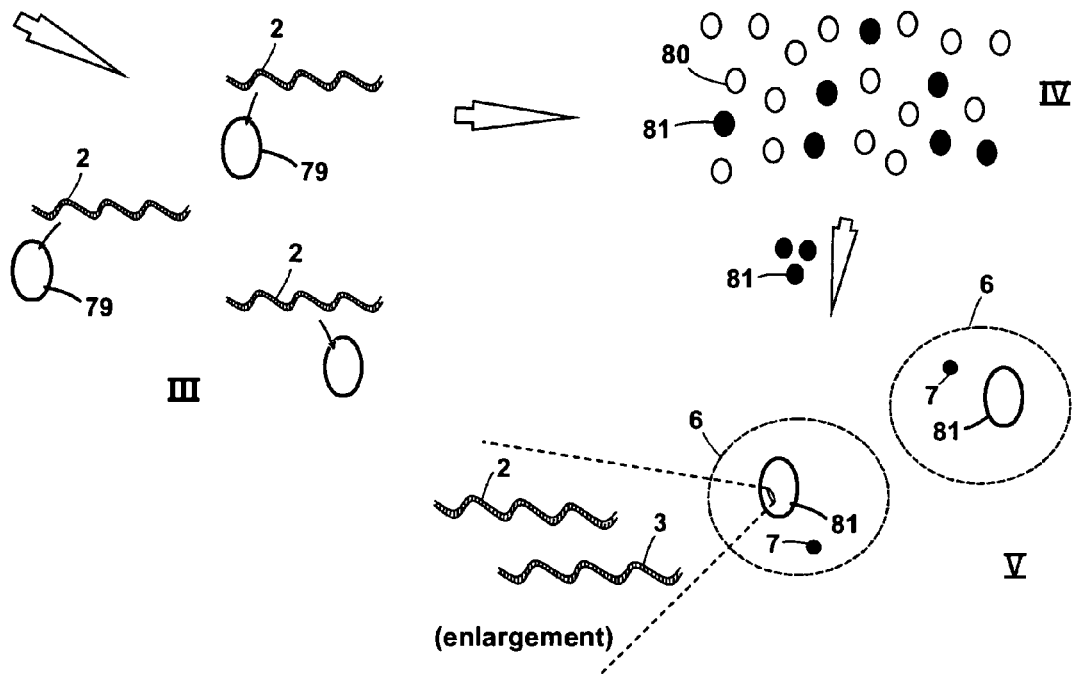
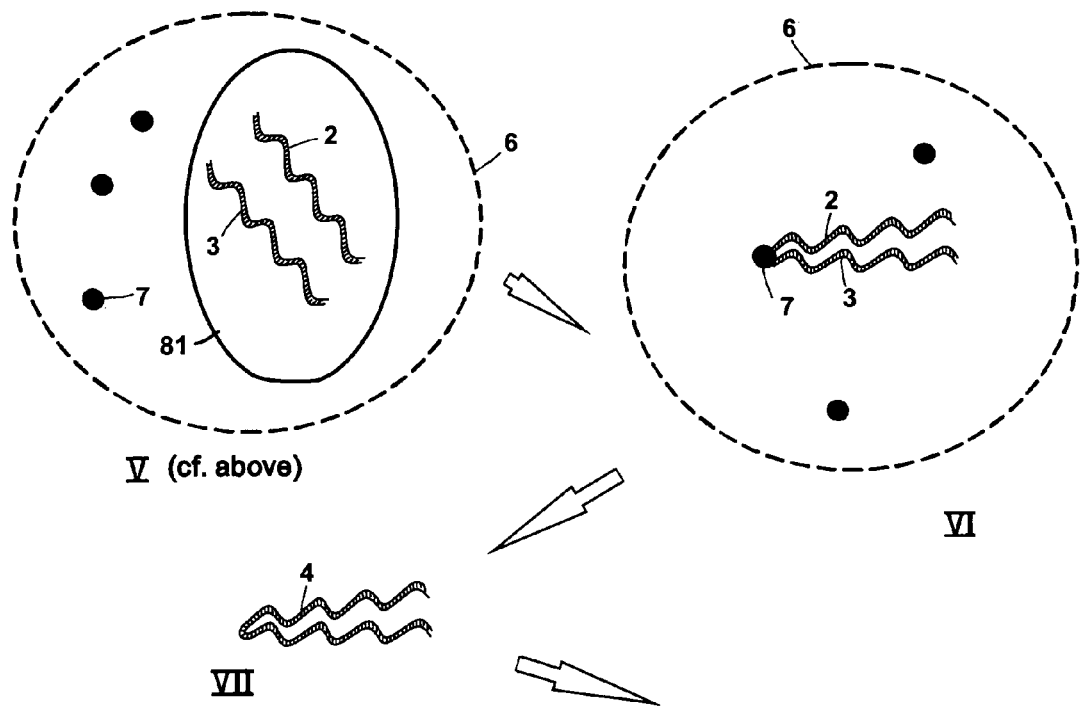

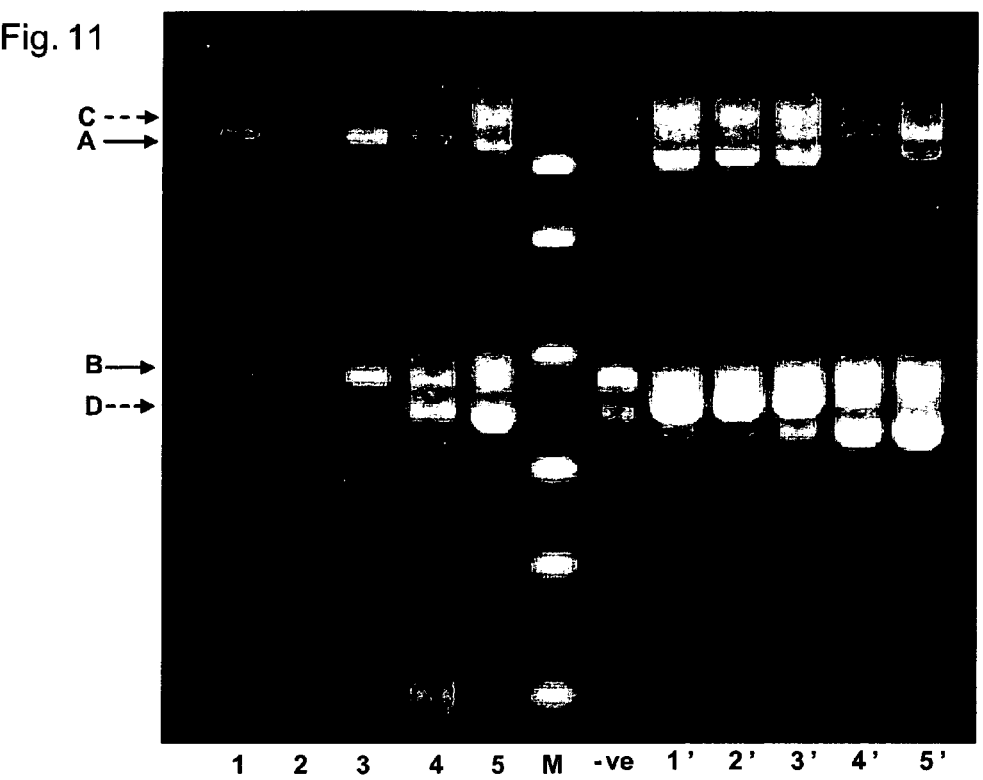
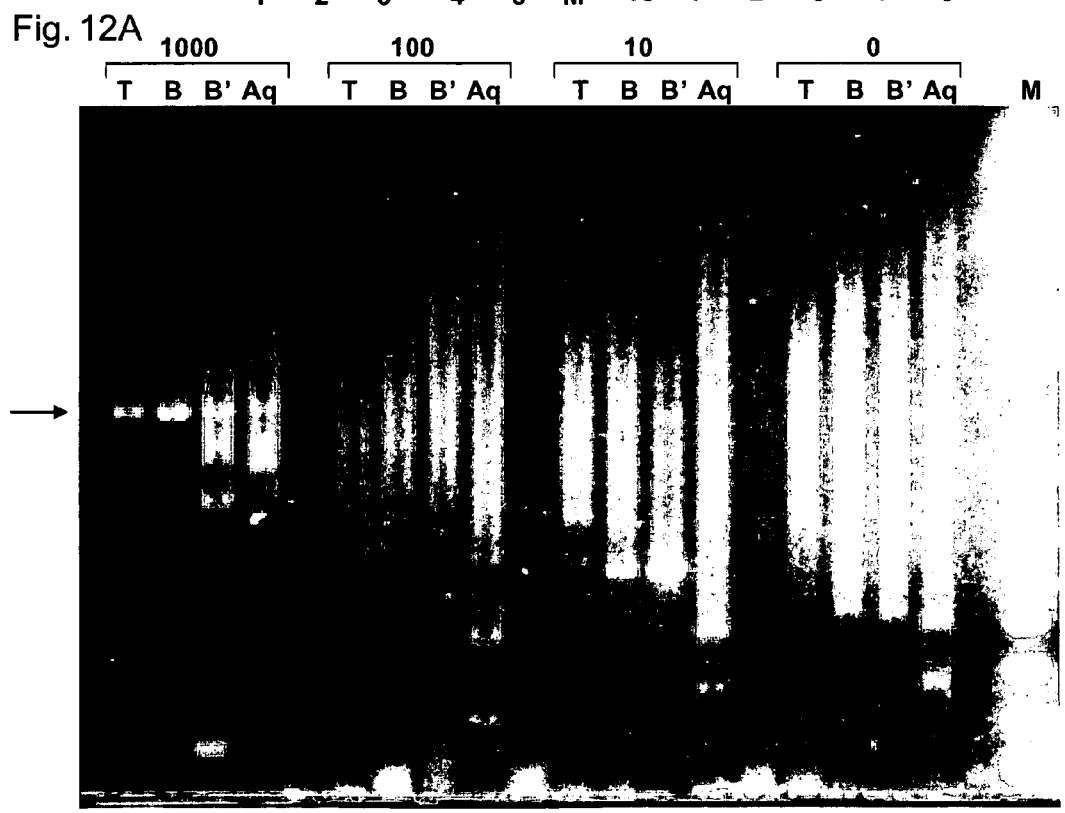

SEQUENCE LISTING

```
<160> NUMBER OF SEQ ID NOS: 13

<210> SEQ ID NO 1
<211> LENGTH: 19
<212> TYPE: DNA
<213> ORGANISM: Artificial Sequence
<220> FEATURE:
<221> NAME/KEY: misc_binding
<223> OTHER INFORMATION: primer

<400> SEQUENCE: 1
catcggtgat gtcggcgat                                                  19

<210> SEQ ID NO 2
<211> LENGTH: 23
<212> TYPE: DNA
<213> ORGANISM: Artificial Sequence
<220> FEATURE:
<221> NAME/KEY: misc_binding
<223> OTHER INFORMATION: primer

<400> SEQUENCE: 2
ataggcgcca gcaaccgcac ctg                                             23

<210> SEQ ID NO 3
<211> LENGTH: 43
<212> TYPE: DNA
<213> ORGANISM: Artificial Sequence
<220> FEATURE:
<221> NAME/KEY: misc_binding
<223> OTHER INFORMATION: primer

<400> SEQUENCE: 3
ggcgcgccat gggaatagct aggttagcag ccggatctca gtg                       43

<210> SEQ ID NO 4
<211> LENGTH: 45
<212> TYPE: DNA
<213> ORGANISM: Artificial Sequence
<220> FEATURE:
<221> NAME/KEY: misc_binding
<223> OTHER INFORMATION: primer

<400> SEQUENCE: 4
```
ctagctattc ccatggcgcg cctagcgcta ccggactcag atctc                45

<210> SEQ ID NO 5
<211> LENGTH: 19
<212> TYPE: DNA
<213> ORGANISM: Artificial Sequence
<220> FEATURE:
<221> NAME/KEY: misc_binding
<223> OTHER INFORMATION: primer

<400> SEQUENCE: 5
caccttgaac atgaactcc                                              19

<210> SEQ ID NO 6
<211> LENGTH: 16
<212> TYPE: DNA
<213> ORGANISM: Artificial Sequence
<220> FEATURE:
<221> NAME/KEY: misc_binding
<223> OTHER INFORMATION: primer

<400> SEQUENCE: 6
ctcggaggcc atggtg                                                 16

<210> SEQ ID NO 7
<211> LENGTH: 22
<212> TYPE: DNA
<213> ORGANISM: Artificial Sequence
<220> FEATURE:
<221> NAME/KEY: misc_binding
<223> OTHER INFORMATION: oligonucleotide for SOE PCR

<400> SEQUENCE: 7
aataccacta caatggatga tg                                          22

<210> SEQ ID NO 8
<211> LENGTH: 23
<212> TYPE: DNA
<213> ORGANISM: Artificial Sequence
<220> FEATURE:
<221> NAME/KEY: misc_binding
<223> OTHER INFORMATION: oligonucleotide for SOE PCR

<400> SEQUENCE: 8
cccggaatta gcttggctgc aac                                         23

<210> SEQ ID NO 9
<211> LENGTH: 44
<212> TYPE: DNA
<213> ORGANISM: Artificial Sequence
<220> FEATURE:
<221> NAME/KEY: misc_binding
<223> OTHER INFORMATION: oligonucleotide for SOE PCR

<400> SEQUENCE: 9
ccgccgctac caccaccgcc aagatggtgc acgatgcaca gttg                  44

<210> SEQ ID NO 10
<211> LENGTH: 49
<212> TYPE: DNA
<213> ORGANISM: Artificial Sequence
<220> FEATURE:
<221> NAME/KEY: misc_binding
<223> OTHER INFORMATION: oligonucleotide for SOE PCR

<400> SEQUENCE: 10

-continued

```
ggcggtggtg gtagcggcgg agtgcgacat catcatcgga agagagtag                    49

<210> SEQ ID NO 11
<211> LENGTH: 31
<212> TYPE: DNA
<213> ORGANISM: Artificial Sequence
<220> FEATURE:
<221> NAME/KEY: misc_binding
<223> OTHER INFORMATION: oligonucleotide for secondary PCR

<400> SEQUENCE: 11
ctattcgatg atgaagatac cccaccaaac c                                       31

<210> SEQ ID NO 12
<211> LENGTH: 25
<212> TYPE: DNA
<213> ORGANISM: Artificial Sequence
<220> FEATURE:
<221> NAME/KEY: misc_binding
<223> OTHER INFORMATION: oligonucleotide for secondary PCR

<400> SEQUENCE: 12
ggaactgtta cacatgtagt tgtag                                              25

<210> SEQ ID NO 13
<211> LENGTH: 19
<212> TYPE: DNA
<213> ORGANISM: Artificial Sequence
<220> FEATURE:
<221> NAME/KEY: misc_binding
<223> OTHER INFORMATION: primer

<400> SEQUENCE: 13
ctcggaggag gccatggtg                                                     19
```

METHODS OF IDENTIFYING A PAIR OF BINDING PARTNERS

CROSS-REFERENCE TO RELATED APPLICATIONS

This patent application is a U.S. National Phase application under 35 §371 of International Application No. PCT/SG2010/000258, filed Jul. 7, 2010, entitled METHODS OF IDENTIFYING A PAIR OF BINDING PARTNERS, which makes reference to and claims the benefit of priority of a U.S. provisional patent application for "Methods Of Identifying A Pair Of Binding Partners" filed on Jul. 7, 2009 with the United States Patent and Trademark Office, and there duly assigned Ser. No. 61/223,524. The content of said application filed on Jul. 7, 2009 is incorporated herein by reference for all purposes in its entirety.

INCORPORATION BY REFERENCE

This application incorporates by reference the material (Sequence Listing) in the ASCII text file called P106056 ST25.txt, created Apr. 24, 2012, having a file size of 3,032 bytes.

FIELD OF THE INVENTION

The present invention relates to methods of identifying a pair of binding partners, in particular of identifying binding partners of one or more proteins. One or both binding partners are linked to a selected nucleic acid molecule. The invention also provides kits that can be used to carry out methods of the invention as well as a kit with components that are based on the method of the invention.

BACKGROUND OF THE INVENTION

In vitro selection of desired biological macromolecules from a pool of available biological macromolecules has become a useful tool in for instance the research on molecular interactions, medical imaging including diagnosis, or in the generation of protein-based biopharmaceuticals including recombinant antibodies. In vitro display technology for the selection of peptides and proteins relies on a physical linkage between the peptide or protein and a nucleic acid encoding the same. A large panel of techniques has been established for this purpose, with the most commonly used being phage/virus display, ribosome display, cell-surface display, 'peptides on plasmids', mRNA display, DNA display, cDNA display and in vitro compartmentalisation including micro-bead display (for reviews see e.g. Rothe, A., et al., *FASEB J.* (2006) 20, 1599-1610; Sergeeva, A., et al., *Advanced Drug Delivery Reviews* (2006) 58, 1622-1654).

Display techniques allow the generation of engineered antibodies and ligands with high affinities for a selected target molecule. It is thus also possible to display an array of peptides or proteins that differ only slightly, typically by way of genetic engineering. Thereby it is possible to screen and subsequently evolve proteins or peptides in terms of properties of interaction and biophysical parameters. Iterative rounds of mutation and selection can be applied on an in vitro basis.

Different means of physically linking the protein or peptide and the respective nucleic acid have been disclosed. Expression in a cell with a cell surface molecule, expression as a fusion polypeptide with a viral/phage coat protein, a stabilised in vitro complex of an RNA molecule, the ribosome and the respective polypeptide, covalent coupling in vitro via a puromycin molecule or via micro-beads are examples of ways of linking the protein/peptide and the nucleic acid presently used in the art.

A further technique of linking a protein or peptide and the respective nucleic acid that does not involve the formation of a physical linkage relies on a water-in-oil emulsion. The water droplets serve as compartments in each of which a single gene is transcribed and translated (Tawfik, D. S., & Griffiths, A. D., *Nature Biotech.* (1998) 16, 652-656, US patent application 2007/0105117). This physical linkage between the peptide or protein and the nucleic acid (encoding it) provides the possibility of recovering the nucleic acid encoding the selected protein or peptide. A nucleic acid with a respective gene and a corresponding protein are clonally constrained within a compartment. Compared to techniques such as immunoprecipitation, in display techniques thus not only binding partners of a selected target molecule can be identified or selected, but the nucleic acid of this binding partner can be recovered and used for further processing.

A further technique for the selection of desired proteins is the use of the yeast two-hybrid system with vectors having a Lox site and the recombinase Cre (Hastie, A. R., & Pruitt, S. C., *Nucleic Acids Research* (2007) 35, 12, e141).

Present display techniques thus provide means for e.g. target discovery, lead discovery and lead optimisation. Vast libraries of peptides or proteins, e.g. antibodies, potentially can be screened on a large scale. However, in order to be able to isolate a complex between a protein or peptide and a target molecule and to remove low-affinity binders, immobilisation of one of the two binding partners is required. Thus current display techniques depend on immobilising the target molecule prior to analysis, typically on the surface a multi-well plate used in the screening process or, in case of in vitro compartmentalisation micro-beads.

Furthermore, current display techniques are one-dimensional in that they require providing a single target molecule against which a broad spectrum of (potentially binding) peptides or proteins can be tested. Simultaneous testing of different target molecules would require isolating and analysing both the respective target and its binding partner and is therefore not practicable.

Accordingly it is an object of the present invention to provide a method of identifying binding partners that can be applied to both immobilised analytes and analytes in solution. As indicated above, such a method would also drastically improve the flexibility of in vitro display technology.

SUMMARY OF THE INVENTION

In a first aspect the present invention provides a method of identifying a binding partner of at least one target molecule within a plurality of analyte molecules. The target molecule is physically combined with a target labeling nucleic acid molecule. The target labeling nucleic acid molecule includes a specific nucleotide sequence that is suitable for identifying the target molecule combined therewith. The method includes contacting the target molecule with the plurality of analyte molecules. Thereby a mixture is formed. The binding partner is suspected to be a member of the plurality of analyte molecules. Each member of the plurality of analyte molecules is physically combined with an analyte labeling nucleic acid molecule. Each analyte labeling nucleic acid molecule includes a selected nucleotide sequence. This nucleotide sequence is suitable for identifying the analyte molecule combined therewith. The method also includes allowing the formation of a complex between the target molecule and the binding partner thereof within the mixture. Further the method includes subdividing the mixture into a plurality of compartments. As a result each compartment includes at most about one target molecule or about one complex between a target molecule and an analyte molecule. By subdividing the mixture into compartments a complex between a target molecule and an analyte molecule is segregated from the residual members of the plurality of analyte molecules. The method also includes allowing the target labeling nucleic acid molecule and the analyte labeling nucleic acid molecule to be linked. Thereby a composite nucleic acid molecule is formed. The composite nucleic acid molecule may still be physically combined with the complex between the target molecule and the analyte molecule. However, this physical combination may also be released after subdividing the mixture into compartments. The method further includes allowing the plurality of compartments to disintegrate. The method also includes retrieving the composite nucleic acid molecule. Further, the method includes determining the sequence of the analyte labeling nucleic acid molecule. Thereby the method includes identifying the binding partner of the target molecule.

In some embodiments retrieving the composite nucleic acid molecule includes carrying out a polymerase chain reaction (PCR) using a pair of a first and a second primer. The first primer is complementary to a part of the sequence of the target labeling nucleic acid molecule. The second primer is a universal primer. As a result the composite nucleic acid molecule, which includes the target labeling nucleic acid molecule and the analyte labeling nucleic acid molecule, is amplified.

In some embodiments the method includes providing a solution suitable for handling nucleic acid molecules. It may also be suitable for handling peptides and/or proteins. In this regard the analyte molecules are in some embodiments peptides, including polypeptides, and/or proteins. In such a method subdividing into compartments the mixture, which has been formed by contacting the plurality of peptides and/or proteins with the target molecule, may include subdividing the solution into compartments. The physical combination of an analyte molecule and the analyte labeling nucleic acid molecule combined therewith is in some embodiments releasable. In some of these embodiments a physical linkage between the analyte molecules and the analyte labeling nucleic acid molecule linked thereto is broken during the method of the invention. In such embodiments thereby the member encoding nucleic acid molecule is released. In other embodiments the physical combination of the analyte molecule and the analyte labeling nucleic acid molecule combined therewith is left to remain intact. The method may in some embodiments include determining the sequence of the released member encoding nucleic acid molecule.

In a second aspect the present invention provides a method of identifying a pair of a first and a second binding partner within a plurality of peptides and/or proteins. Typically in this method the identity of one of the binding partners, e.g. the first binding partner, is known. The first and the second binding partner are capable of forming a complex. The method includes providing the plurality of peptides and/or proteins. Each member of the plurality of peptides and/or proteins is physically combined with a member encoding nucleic acid molecule. The member encoding nucleic acid molecule includes a nucleotide sequence that encodes the peptide or protein combined therewith. The method also includes subdividing the plurality of peptides and/or proteins into compartments. As a result each compartment includes at most about one complex formed between a pair of binding partners. Alternatively a compartment includes at most about one member of the plurality of peptides and/or proteins. Accordingly, by subdividing the plurality of peptides and/or proteins into compartments, a complex between the first and the second binding partner is segregated from the residual peptides and/or proteins of the plurality of peptides and/or proteins. Further, the method includes allowing the member encoding nucleic acid molecule of the first binding partner and the member encoding nucleic acid molecule of the second binding partner to be linked. Thereby a composite nucleic acid molecule is formed. The method further includes allowing the plurality of compartments to disintegrate. The method also includes retrieving the composite nucleic acid molecule. Further, the method includes determining the sequence of the amplified composite nucleic acid molecule. Thereby the method includes identifying the first and/or the second binding partner.

In some embodiments the method also includes adding a capture probe. The capture probe is capable of associating to the above mentioned complex between the first and the second binding partner. Further, the method includes allowing the capture probe to associate to the complex between the first and the second binding partner. Further, the method includes retrieving the capture probe. Thereby the complex between the first and the second binding partner, which is linked to the composite nucleic acid molecule, is retrieved.

In some embodiments the physical combination between the nucleic acid molecule and the peptide or protein is releasable. In some of these embodiments the method also includes releasing the physical combination between the first binding partner and the member encoding nucleic acid molecule combined therewith. Likewise, in some embodiments the method includes breaking the physical linkage between the second binding partner and the member encoding nucleic acid molecule combined therewith. In some embodiments the physical combination between the first binding partner and the corresponding member encoding nucleic acid molecule is the same as the physical combination linkage between the second binding partner and the corresponding member encoding nucleic acid molecule. In these embodiments the physical combination is thus released concurrently. Thereby the method includes releasing the two linked member encoding nucleic acid molecules. In this case the method includes determining the sequence of the released linked member encoding nucleic acid molecules of the pair of binding partners.

In a third aspect the present invention provides a method of identifying a binding partner of a target peptide or protein within a plurality of peptides and/or proteins. The target peptide or protein is included in a member of a first plurality of peptides and/or proteins. The binding partner is suspected to be included in a member of a second plurality of peptides and/or proteins. Each member of the first and the second plurality of peptides and/or proteins is physically combined with a member encoding nucleic acid molecule. The respective member encoding nucleic acid molecule includes a nucleotide sequence encoding the peptide or protein combined therewith. The method includes combining the first and the second plurality of peptides and/or proteins. Thereby a mixture is formed. The method further includes allowing the formation of a complex between the target peptide or protein and the binding partner thereof. The method also includes subdividing the mixture into compartments. As a result each compartment includes at most about one member or about one complex between members of the combined pluralities of peptides and/or proteins. Further, the method includes allowing the member encoding nucleic acid molecule of the target peptide or protein and the member encoding nucleic acid molecule of the binding partner of the formed complex to be linked. Thereby the method includes forming a composite nucleic acid molecule. The method also includes allowing the compartments to disintegrate. The method also includes retrieving the composite nucleic acid molecule. Further, the method includes determining the sequence of the composite nucleic acid molecule. Thereby the method includes identifying the binding partner.

In a fourth aspect the present invention provides a method of identifying one or more pairs of a first and a second binding partner within a plurality of peptides and/or proteins. The first and the second binding partner are capable of forming a complex. The method includes providing a library of nucleic acid molecules, which encode a plurality of peptides and/or proteins. The plurality of peptides and/or proteins is suspected to include the one or more pairs of a first and a second binding partner. Further, the method includes providing a plurality of molecules of a first vector (e.g. a first plasmid) and a plurality of molecules of a second vector (e.g. a second plasmid). The first vector has a nucleic acid sequence that encodes a first complementing moiety, and the second vector has a nucleic acid sequence that, encodes a second complementing moiety. The first and the second complementing moiety, when brought into physical proximity, complement each other. These two moieties complement each other in such a way that a reporter factor is defined. The method also includes providing each member of the two pluralities of a first and of a second vector with one nucleic acid molecule. The nucleic acid molecule is a nucleic acid molecule of the library of nucleic acid molecules that encode the plurality of peptides and/or proteins. The method further includes introducing one of the members (or specimen) of the first vector and of the members (or specimen) of the second vector into the same suitable cell. Both the first and the second vector are each provided with a nucleic acid molecule. This nucleic acid molecule encodes one of the plurality of peptides and/or proteins. The method also includes allowing in the cell the expression of the pair of peptides and/or proteins that is encoded by the nucleic acids with which the vectors that have been introduced into the cell have been provided. Further, the method includes collecting, for example isolating, any cell in which the formation of the reporter factor is detected. The method also includes subdividing any individual collected, e.g. isolated, cells in which the formation of the reporter factor is detected into compartments. As a result of this division into compartments each compartment includes at most about one cell. Further, the method includes allowing the member encoding nucleic acid molecule of the first binding partner and the member encoding nucleic acid molecule of the second binding partner to be linked in the compartments. Thereby the method includes forming a composite nucleic acid molecule. The method also includes allowing the compartments to disintegrate. The method also includes retrieving the composite nucleic acid molecule. Further, the method includes determining the sequence of the composite nucleic acid molecule. Thereby the method includes identifying the second binding partner and/or identifying the first binding partner.

In a fifth aspect the present invention provides a method of identifying one or more binding partners of at least one target peptide or protein within a plurality of analyte peptides and/or proteins. The target peptide or protein and the binding partner thereof are capable of forming a complex. The method includes providing a library of nucleic acid molecules encoding the plurality of analyte peptides and/or proteins. The plurality of peptides and/or proteins is suspected to include a binding partner of the at least one target peptide or protein. The method also includes providing at least one nucleic acid molecule encoding the at least one target peptide or protein. Further, the method includes providing a plurality of a plurality of members of a first vector. The method also includes providing a plurality of members of a second vector. The first vector has a nucleic acid sequence, which encodes a first complementing moiety, and the second vector has a nucleic acid sequence, which encodes a second complementing moiety. The first and the second complementing moiety complement each other when brought into physical proximity. Thereby the first and the second complementing moiety together define a reporter factor. The method also includes providing each member of the plurality of members of the first vector with one nucleic acid molecule. This nucleic acid molecule, provided with the respective first vector, is a nucleic acid molecule of the library of nucleic acid molecules encoding the plurality of analyte peptides and/or proteins. The method also includes providing each member of the plurality of molecules of the second vector with one nucleic acid molecule. The nucleic acid molecule provided with the respective second vector is a nucleic acid molecule of the at least one nucleic acid molecule, which encodes the at least one target peptide or protein. The method of the invention includes introducing one of the plurality of molecules of the first vector and one of the plurality of molecules of the second vector into the same suitable cell. The method of the invention also includes allowing in the cell the expression of the pair of peptides and/or proteins, which is encoded by the nucleic acid that has been included in the respective vectors. Further, the method includes collecting, for example isolating, any cell in which the formation of the reporter factor is detected. The method also includes subdividing any individual collected, e.g. isolated, cells in which the formation of the reporter factor is detected into compartments. As a result of this division into compartments each compartment includes at most about one cell. Further, the method includes allowing the member encoding nucleic acid molecule of the target peptide or protein and the member encoding nucleic acid molecule of the binding partner thereof to be linked in the compartments. Thereby the method includes forming a composite nucleic acid molecule. The method also includes allowing the compartments to disintegrate. The method also includes retrieving the composite nucleic acid molecule. Further, the method includes determining the sequence of the composite nucleic acid molecule. Thereby the method includes identifying the binding partner of the target peptide or protein.

In a sixth aspect the present invention provides a kit of parts for identifying a binding partner of a target peptide or protein. The kit includes a plurality of composite nucleic acid molecules. Each composite nucleic acid molecule of the plurality of composite nucleic acid molecules includes the sequences of a pair of a first peptide or protein and a second peptide or protein. The first peptide or protein and the second peptide or protein define binding partners in that they are capable of forming a complex with each other. The kit also includes a universal primer. Typically the kit includes a plurality of containers, e.g. vials, tubes etc. One of the containers includes the plurality of composite nucleic acid molecules. One container includes the universal primer.

BRIEF DESCRIPTION OF THE DRAWINGS

The invention will be better understood with reference to the detailed description when considered in conjunction with non-limiting examples and the accompanying drawings, in which:

FIG. 6A illustrates a technique used in the art, the yeast two hybrid system, suitable for incorporation into the method of the invention.

Figure 8A:
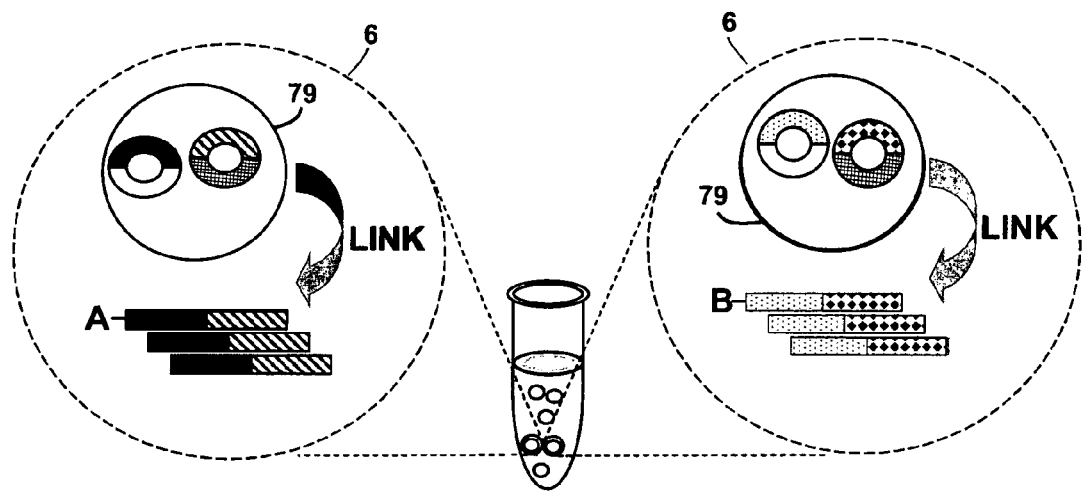
FIG. 8A shows cells containing two different plasmids (white and hatched donuts), each of which carries a different insert (black, striped, stippled, diamond)-emulsified in reaction mixture. Emulsification ensures segregation of cells into individual compartments and correct (clonal) linkage of the plasmid inserts (products A and B).
Figure 8B:
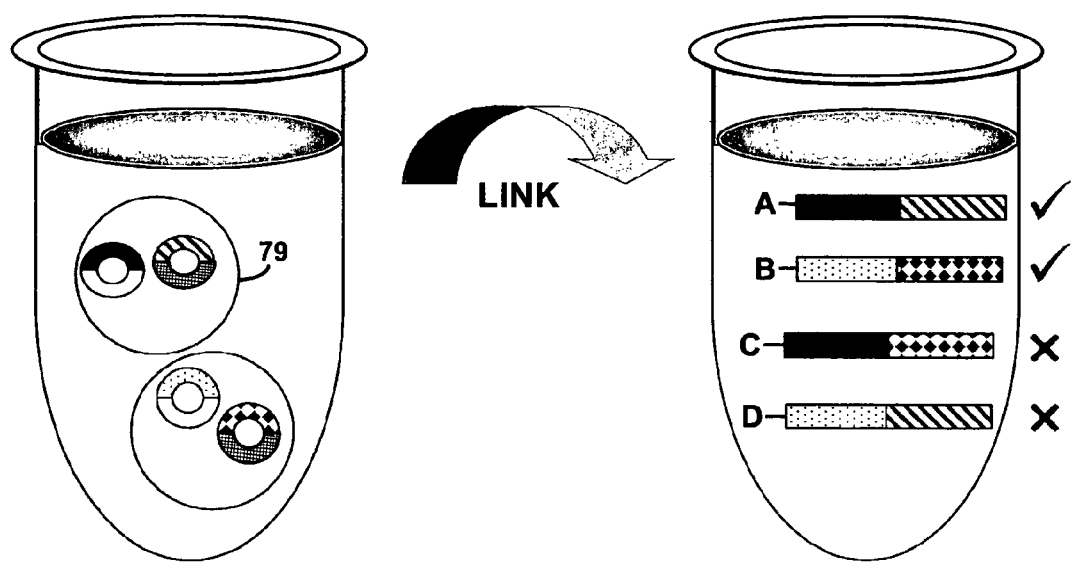

As FIG. 8B illustrates, in the absence of emulsification the cells (and plasmids) freely interact during linkage procedure, resulting in both correct linkage products (A and B) and incorrect linkage products (C and D).

Figure 9:
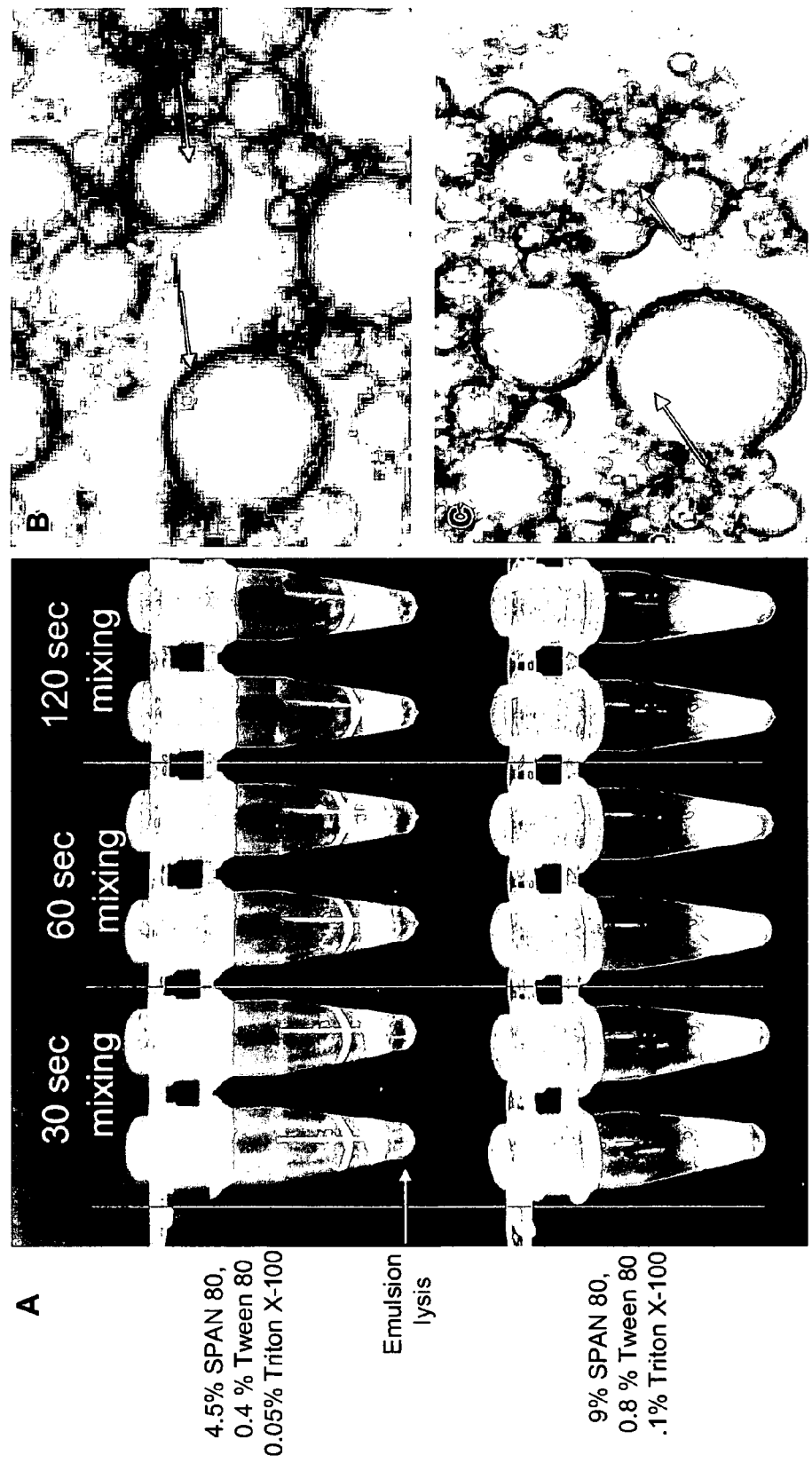

FIG. 9 illustrates schematically the emulsion optimization in a method of the invention. A: Various mixing times and two oil phases with different surfactant concentrations were used as indicated. Emulsion lysis was monitored by gauging the amount of aqueous phase accumulation at the bottom of the tubes. B, C: Representative images of optimized emulsions containing yeast cells (arrows).

Figure 10:
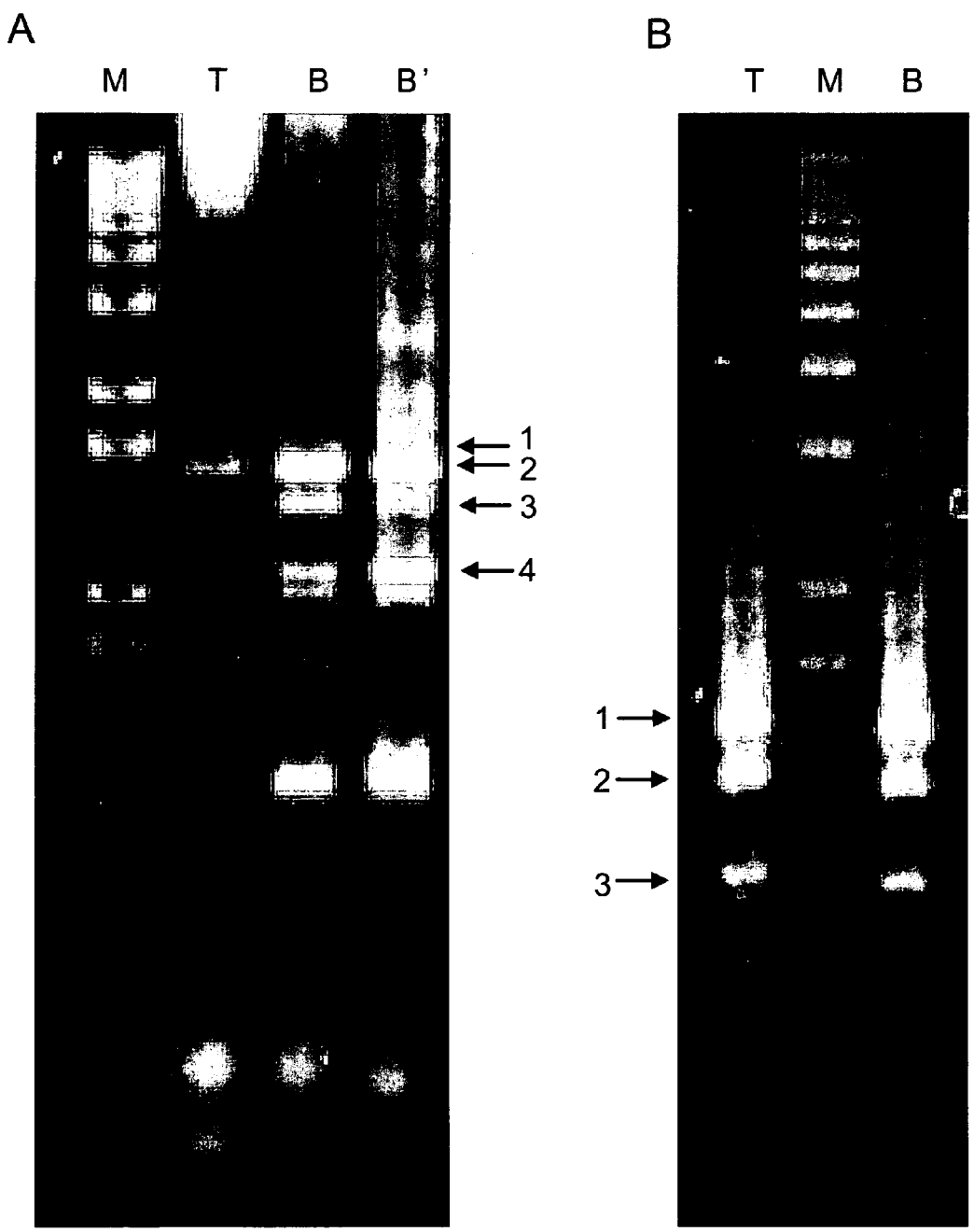

FIG. 10 illustrates the analysis of the linkage of interacting partner cDNA. A: 2,3: Correctly spliced 1350 bp and 1200 bp bands arising from cognate pairing between YC16_14 and Yc16_6. 1,4: (T=top fraction and B=bottom fraction of emulsion SOE-PCR, B'=lysed emulsion; M=Molecular weight marker). B: nested secondary PCR in emulsion.

FIG. 11 is a further example of an analysis of the linkage of interacting partner cDNA. 1: Top emulsion fraction, 2: Middle emulsion fraction, 3: Bottom emulsion fraction, 4: Lysed emulsion fraction, 5: Aqueous control, M: Molecular weight marker, 1' to 5': nested secondary PCRs of lanes 1 to 5. Correctly spliced 1100 bp and 625 bp bands from cognate pairing between two inserts in YC9 (A) and two inserts in YC3 (B) are indicated vs. incorrect linkage (C, D).

FIG. 12: Model selection and threshold of detection (T=top fraction and B=bottom fraction of emulsion SOE-PCR, B'=lysed emulsion, Aq=non-emulsified aqueous control; M=Molecular weight marker). (A) Emulsion SOE-PCR with subsequent secondary PCR of 1000, 100, 10 with 0 YC8 cells and 250,000 YC16 library cells. (B) Emulsion SOE-PCR with subsequent secondary PCR of 500, 300, 200, 100 and 0 YC8 cells with 250,000 YC16 library cells.

DETAILED DESCRIPTION OF THE INVENTION

Protein-protein interactions are fundamental constituents of all biological processes. Many techniques have been developed to uncover the global protein-protein interaction network in the cell. Two-hybrid methods, especially genome-wide yeast two-hybrid screens, have for example been regarded as promising in this context, because they enable in-parallel and in vivo interrogation of all possible binary interactions. However, these efforts are limited by throughput issues, sequencing capabilities and the primary information content of these screens is not in a convenient format.

The present invention provides methods of identifying a pair of binding partners. Hence, the method may in some embodiments also be defined as a method of determining whether a target molecule interacts with, i.e. binds to or forms a complex with, any member of a plurality of analyte molecules. A method according to the invention may be carried out as a screening method, including a high-throughput method. Where one of the binding partners is known the method may include providing the known partner and contacting it with a plurality of test partners, i.e. analyte molecules.

A method according to the invention employs compartmentalization, such as in vitro compartmentalization, in a technique that can be called in vitro Compartmentalized Linkage of Interacting Partners, or iCLIP. Such a method enables genes encoding interacting proteins to be linked in a single segment of DNA. As a result the information from for instance diverse two-hybrid assays can stored, duplicated and interrogated with ease.

In one aspect the invention provides a method of identifying a binding partner of at least one target molecule within a plurality of analyte molecules, such as two or at least two, three or at least three, four or at least four, five or at least five, six or at least six, seven or at least seven, or more analyte molecules. The target molecule is physically combined with, for instance physically linked to, a target labeling nucleic acid molecule. The physical combination between the target molecule and the target labelling nucleic acid molecule combined therewith may be of any nature. The physical combination may in some embodiments include one of a covalent bond, a non-covalent bond, a linking molecule, a cell, a virus, a phage, a ribosome, and any combination thereof. A respective cell may for instance be a prokaryotic or a eukaryotic cell. Three illustrative examples of an eukaryotic cell that may be used are a yeast such as *S. cerevisiae*, an insect cell such as an Sf9 cell, and a fungus cell such as *Aspergillus nidulans*. Two illustrative examples of a prokaryotic cell are *E. coli* and *B. subtilis*.

The target molecule may for example include one of a peptide, a protein, a peptoid, a metabolite, a drug molecule, a drug candidate molecule, a drug metabolite, a lipid, a carbohydrate, a vitamin, a synthetic polymer, a cell, a microorganism, a virus or any combination thereof. The target labeling nucleic acid molecule has or includes a specific nucleotide sequence that is suitable for identifying the target molecule that is combined with the target labeling nucleic acid molecule. In some embodiments the target labeling nucleic acid molecule is or includes DNA or RNA. In some embodiments where the target molecule is one of a peptide, a polypeptide, a protein, and a nucleic acid, the target labeling nucleic acid molecule includes a nucleotide sequence that encodes the target molecule combined with the target labeling nucleic acid molecule. A respective nucleic acid molecule is in some embodiments an aptamer.

The method includes providing the one or more target molecule(s). The method also includes providing the plurality of analyte molecules. Typically the target molecule(s) and the analyte molecules are provided in solution of a suitable solvent, such as a polar solvent, e.g. an aqueous solution (cf also below). In some embodiments the plurality of analyte molecules is provided in a liquid suitable for handling nucleic acid molecules and for handling the target molecule, which may—depending on the physical nature of the target molecule—be a polar solvent, e.g. an aqueous solution.

The present method includes contacting the target molecule with the plurality of analyte molecules. Any analyte molecule that is capable of defining a binding partner to a selected target molecule may be included in the plurality of analyte molecules. The analyte molecules may for instance include one of a peptide, a protein, a peptoid, a metabolite, a drug molecule, a drug candidate molecule, a drug metabolite, a lipid, a carbohydrate, a vitamin, a synthetic polymer, a cell, a microorganism, a virus or any combination thereof.

The binding partner of the at least one target molecule is suspected to be a member of this plurality of analyte molecules. Each member of the plurality of analyte molecules is physically combined with an analyte labeling nucleic acid molecule. A respective analyte labeling nucleic acid molecule may for example be or include DNA or RNA. Each analyte labeling nucleic acid molecule includes a selected nucleotide sequence, which is suitable for identifying the analyte molecule that is combined with the respective analyte labeling nucleic acid molecule. In some embodiments each of the plurality of analyte molecules is a peptide or a protein, with the analyte labeling nucleic acid molecule including a nucleotide sequence that encodes the analyte molecule combined therewith. In some of these embodiments the selected nucleotide sequence, which is suitable for identifying the analyte molecule, includes the nucleotide sequence encoding the analyte molecule. In some embodiments the analyte labeling nucleic acid molecule further includes a tag sequence. This tag sequence may encode a peptide tag.

Accordingly, in some embodiments a plurality of peptides and/or proteins defines the plurality of analyte molecules. Such a plurality of peptides and/or proteins is in some embodiments formed by providing a plurality of member encoding nucleic acid molecules. Each of the member encoding nucleic acid molecules may have a nucleotide sequence encoding one member of the plurality of peptides and/or proteins that define the plurality of analyte molecules. The nucleotide sequences of the member encoding nucleic acid molecules may be expressed, thereby forming the encoded protein or peptide. Further, the formation of a physical linkage between the member encoding nucleic acid molecule and the peptide or protein encoded by the same may be allowed. The physical linkage between the member encoding nucleic acid molecule and the peptide or protein encoded by the same is in some embodiments a linkage in cis. Allowing the formation of a physical linkage between the member encoding nucleic acid molecule and the member of the plurality of peptides, polypeptides and/or proteins may in some embodiments include one of a covalent linkage to puromycin, a complex with a ribosome and inclusion in a bacteriophage or a virus particle. In some embodiments the specific nucleotide sequence suitable for identifying the target molecule includes the nucleotide sequence encoding the target molecule.

In some embodiments each one of the plurality of member encoding nucleic acid molecules is included in one vector, for example a plasmid. Accordingly, individual vectors may carry each one of the member encoding nucleic acid molecules.

The physical combination between the analyte molecules, which are suspected to be capable of forming a complex with the target molecule, and the analyte labelling nucleic acid molecules combined therewith may be of any nature. In some embodiments the physical combination between an analyte molecule and a respective analyte labelling nucleic acid molecule may include one of a covalent bond, a non-covalent bond, a linking molecule, a cell, a virus, a phage, a ribosome, and any combination thereof.

In some embodiments the physical combination between the target molecule and the target labeling nucleic acid molecule and between each analyte molecule and the analyte labeling nucleic acid molecule is a cell. In such an embodiment the cell may include a target molecule, a target labeling nucleic acid molecule, an analyte molecule and an analyte labeling nucleic acid molecule. The target molecule may be coupled to a first complementing moiety and each member of the plurality of analyte molecules may be coupled, for instance covalently linked, to a second complementing moiety. Further, in such an embodiment the first and the second complementing moiety, when brought into physical proximity, may complement each other. Thereby they may be taken to together define a reporter factor.

A respective reporter factor may be a factor that is capable of activating the expression of a protein that affects the phenotype of a suitable host cell. The first and the second complementing moiety may in some embodiments be two fragments of the protein. The two fragments may for example define two domains of the protein. In some embodiments the first and the second complementing moiety are capable of being expressed in the cell. In some embodiments the target molecule and the first complementing moiety are included in a fusion protein encoded by the target labeling nucleic acid molecule. In some embodiments each one of the plurality of analyte molecules and the second complementing moiety are included in a fusion protein that is encoded by the analyte labeling nucleic acid molecule.

As explained above, the target molecule may be included in a fusion protein that is encoded by the target labeling nucleic acid molecule. In such an embodiment the analyte molecule may for example be included in a fusion protein encoded by the analyte labeling nucleic acid molecule. The fusion proteins may in such embodiments be provided by expressing under suitable conditions a target labeling nucleic acid molecule and a plurality of analyte labeling nucleic acid molecules in a plurality of cells. In some embodiments in the present method of the invention the expression of only one pair of about one target labeling nucleic acid molecule and about one analyte labeling nucleic acid molecule is allowed to occur in each of the plurality of cells. The pair of about one target labeling nucleic acid molecule and of about one analyte labeling nucleic acid molecule may for example be expressed using a two hybrid system.

By contacting the target molecule with the plurality of analyte molecules a mixture is formed. In some embodiments this mixture is included in a liquid that is suitable for handling nucleic acid molecules and for handling the target molecule. This liquid may be taken to be a first liquid (vide infra). In the method of the invention the formation of a complex between the target molecule and the binding partner thereof is allowed to occur within the mixture.

In some embodiments the present method is a method of identifying a binding partner of at least two target molecules within a plurality of analyte molecules. Accordingly, in such an embodiment the target molecule or target molecules is/are suspected to be, or is/are, included in the plurality of analyte molecules. In such an embodiment forming the mixture is carried out by contacting the at least two target molecules with the plurality of analyte molecules.

Further, in the present method of the invention the mixture is subdivided into a plurality of compartments, such that each compartment includes or has at most about one target molecule or at most about one complex between a target molecule and an analyte molecule. In some embodiments subdividing the mixture into a plurality of compartments is carried out such that each compartment includes at most about one target molecule, at most about one complex between a target molecule and an analyte molecule, or at most about one analyte molecule. Any technique for subdividing the mixture into a plurality of compartments known in the art may be employed as long as it leaves the analyte molecules and the at least one target molecule to such an extent intact that the formation of a complex can occur. As noted above, in some embodiments this mixture is included in a first liquid that is suitable for handling nucleic acid molecules and for handling the target molecule. In such an embodiment subdividing the mixture into compartments may include adding a second liquid. Such a second liquid may be immiscible with the first liquid. In some embodiments subdividing the mixture into compartments includes allowing phase separation. In phase separation two phases are formed. The first phase is defined by the first liquid, the second phase is defined by the second liquid added thereto. Typically the first phase forms a plurality of compartments within the second phase.

In some embodiments subdividing the mixture into compartments includes emulsification. Subdividing the mixture into compartments may for example include forming a water-in-oil emulsion, a water-in-ionic liquid emulsion or a water-in-water emulsion. Subdividing the mixture into compartments is in some embodiments carried out after allowing the formation of a complex between the target molecule and the binding partner thereof.

By subdividing the mixture into a plurality of compartments a complex between a target molecule and an analyte molecule is segregated from the residual members of the plurality of analyte molecules. In some embodiments after subdividing the mixture into compartments the physical combination between the analyte molecule defining the binding partner of the target molecule and the analyte labeling nucleic acid molecule combined therewith is released. Thereby the analyte labeling nucleic acid molecule is released. The present method of the invention further includes allowing the target labeling nucleic acid molecule and the analyte labeling nucleic acid molecule to be linked. As a result a composite nucleic acid molecule is formed.

The plurality of compartments is allowed to disintegrate and the composite nucleic acid molecule is retrieved. Retrieving the composite nucleic acid molecule may in some embodiments include carrying out a primer based nucleic acid amplification using at least one primer that is complementary to a part of the sequence of the target labeling nucleic acid molecule. As two illustrative examples of primer based nucleic acid amplification, a polymerase chain reaction (PCR) or isothermal amplification may be carried out. Isothermal amplification may for example be carried out as strand displacement amplification (SDA), helicase based amplification or rolling circle amplification. PCR may be carried out using a pair of a first and a second primer. The first primer is complementary to a part of the sequence of the target labeling nucleic acid molecule. The second primer may be a universal primer. By carrying out a primer based nucleic acid amplification the composite nucleic acid molecule may be amplified. Retrieving the composite nucleic acid molecule may in some embodiments include (additionally or alternatively) adding to the mixture a capture probe. Such a capture probe may be capable of associating to the complex between the target molecule and the binding partner thereof. Further, the capture probe may be retrieved. Thereby the complex between the target molecule and the binding partner thereof may be retrieved.

In some embodiments the present method further includes purifying the amplified composite nucleic acid molecule, for instance by extracting the same.

In the following the method of the invention is explained and exemplified by means of embodiments in which at least one binding partner is a peptide and/or protein. It is understood that pluralities of pairs of binding partners can likewise be identified using the method of the invention. For sake of clarity the applicability to pluralities of pairs of binding partners is not constantly recited throughout the description but only mentioned casually. While both binding partners may be any molecule, cell, virus or microorganism, the focus will now be on embodiments where one or both binding partners are a peptide or a protein. In embodiments where one of the binding partners is different from a peptide or protein, this binding partner may be referred to as a target molecule.

Accordingly, in such embodiments the method can also be taken as a method of identifying a peptide and/or protein that is a binding partner of a target molecule. The target molecule may include or be any molecule that is capable of forming a complex with a peptide or a protein.

Examples of a suitable target molecule include, but are not limited to, a peptide, a polypeptide, a protein, a peptoid, a nucleic acid molecule, a metabolite, a drug molecule, a drug candidate molecule, a drug metabolite, a lipid, a carbohydrate, a vitamin, a synthetic polymer, a cell, a microorganism, a virus or any combination thereof. The target molecule may be a molecule within a plurality of analyte molecules. The target molecule may also be a nucleic acid that is capable of forming a complex with a peptide or protein. An illustrative example in this regard is an aptamer that is an oligonucleic acid. Aptamers have properties that can be compared to those of antibodies. Aptamers are typically engineered by systematic in vitro selection, a process that can be carried out in an automated manner. In some embodiments a method according to the present invention is accordingly a method of screening aptamers. In one embodiment of a method according to the invention a plurality, e.g. a library, of tagged aptamers may be screened against a library of peptides/proteins. Each of the peptides/proteins is physically combined with, e.g. physically linked to a labeling nucleic acid molecule, which may include a sequence encoding the peptide/protein. A respective method may be a method of generating (e.g. producing) a library of composite nucleic acids. These composite nucleic acids have a sequence of an aptamer and of a sequence encoding a protein that defines a binding partner of the aptamer.

Numerous other examples of interactions of nucleic acid molecules and peptides/proteins are known. As an illustrating example, the specific interaction of the RNA-binding protein Musashi1 and mRNA of the doublecortin gene has been identified using an embodiment of the mRNA display technique (Horisawa, K., et al., *FEBS Lett.* (2009) 583, 14, 2429-2434). A similar screening can be carried out using a method according to the present invention. Those skilled in the art will appreciate that additionally a method according to the present invention not only allows identifying binding partners of one target molecule at a time, but that any desired number of target molecules may be analysed for binding partners without the need of running numerous individual screens in parallel. Due to this advantage the present invention is particularly well suited for high throughput screening approaches.

The target molecule may be included in any sample of any origin. It may for instance, but not limited to, be derived from human or non-human animals, plants, bacteria, viruses, spores, fungi, or protozoa, or from organic or inorganic material of synthetic or biological origin. Accordingly, any of the following samples selected from, but not limited to, the group consisting of a soil sample, an air sample, an environmental sample, a cell culture sample, a bone marrow sample, a rainfall sample, a fallout sample, a sewage sample, a ground water sample, an abrasion sample, an archaeological sample, a food sample, a blood sample, a serum sample, a plasma sample, an urine sample, a stool sample, a semen sample, a lymphatic fluid sample, a cerebrospinal fluid sample, a nasopharyngeal wash sample, a sputum sample, a mouth swab sample, a throat swab sample, a nasal swab sample, a bronchoalveolar lavage sample, a bronchial secretion sample, a milk sample, an amniotic fluid sample, a biopsy sample, a cancer sample, a tumour sample, a tissue sample, a cell sample, a cell culture sample, a cell lysate sample, a virus culture sample, a nail sample, a hair sample, a skin sample, a forensic sample, an infection sample, a nosocomial infection sample, a production sample, a drug preparation sample, a biological molecule, a production sample, a protein preparation sample, a lipid preparation sample, a carbohydrate preparation sample, a space sample, an extraterrestrial sample or any combination thereof may be processed in a method of the invention. Where desired, a respective sample may have been pre-processed to any degree. As an illustrative example, a tissue sample may have been digested, homogenised or centrifuged prior to being used with the device of the present invention. The sample may furthermore have been prepared in form of a fluid, such as a solution. Examples include, but are not limited to, a solution or a slurry of a nucleotide, a polynucleotide, a nucleic acid, a peptide, a polypeptide, an amino acid, a protein, a biochemical composition, an organic chemical composition, an inorganic chemical composition, a synthetic polymer, a metal, a lipid, a carbohydrate, a combinatory chemistry product, a drug candidate molecule, a drug molecule, a drug metabolite or of any combinations thereof. Further examples include, but are not limited to, a suspension of a metal, a suspension of metal alloy, and a solution of a metal ion or any combination thereof, as well as a suspension of a cell, a virus, a microorganism, a pathogen, a radioactive compound or of any combinations thereof. It is understood that a sample may furthermore include any combination of the aforementioned examples. As an illustrative example, the sample that includes a target molecule that is a nucleic acid molecule may be a mammal sample, for example a human or mouse sample, such as a sample of total mRNA.

The term "nucleic acid molecule" as used herein refers to any nucleic acid in any possible configuration, such as single stranded, double stranded or a combination thereof. Nucleic acids include for instance DNA molecules, RNA molecules, analogues of the DNA or RNA generated using nucleotide analogues or using nucleic acid chemistry, locked nucleic acid molecules (LNA), protein nucleic acids molecules (PNA) and tecto-RNA molecules (e.g. Liu, B., et al., *J. Am. Chem. Soc.* (2004) 126, 4076-4077). A PNA molecule is a nucleic acid molecule in which the backbone is a pseudopeptide rather than a sugar. Accordingly, PNA generally has a charge neutral backbone, in contrast to for example DNA or RNA. Nevertheless, PNA is capable of hybridising at least complementary and substantially complementary nucleic acid strands, just as e.g. DNA or RNA (to which PNA is considered a structural mimic). An LNA molecule has a modified RNA backbone with a methylene bridge between C4' and O2', which locks the furanose ring in a N-type configuration, providing the respective molecule with a higher duplex stability and nuclease resistance. Unlike a PNA molecule an LNA molecule has a charged backbone. DNA or RNA may be of genomic or synthetic origin and may be single or double stranded. Such nucleic acid can be e.g. mRNA, cRNA, synthetic RNA, genomic DNA, cDNA synthetic DNA, a copolymer of DNA and RNA, oligonucleotides, etc. A respective nucleic acid may furthermore contain non-natural nucleotide analogues and/or be linked to an affinity tag or a label.

Many nucleotide analogues are known and can be detected and/or used (see below) in the methods of the invention. A nucleotide analogue is a nucleotide containing a modification at for instance the base, sugar, or phosphate moieties. As an illustrative example, a substitution of 2'-OH residues of siRNA with 2'F, 2'O-Me or 2'H residues is known to improve the in vivo stability of the respective RNA. Modifications at the base moiety include natural and synthetic modifications of A, C, G, and T/U, different purine or pyrimidine bases, such as uracil-5-yl, hypoxanthin-9-yl, and 2-aminoadenin-9-yl, as well as non-purine or non-pyrimidine nucleotide bases.

Other nucleotide analogues serve as universal bases. Universal bases include 3-nitropyrrole and 5-nitroindole. Universal bases are able to form a base pair with any other base. Base modifications often can be combined with for example a sugar modification, such as for instance 2'-O-methoxyethyl, e.g. to achieve unique properties such as increased duplex stability.

In some embodiments binding partners of a plurality of target molecules are concurrently identified, i.e. without running the method several-fold in parallel. Hence, the method may be a method of identifying a binding partner of at least two target molecules within a plurality of analyte molecules. In embodiments where the target molecule is added to a plurality of analyte molecules suspected to include binding partners, accordingly a plurality of the target molecules of interest, i.e. two or more target molecules—as the case may be—are used in the method of the invention.

As noted above, the binding partner of the target molecule may be or may include a peptide and/or a protein. The term "peptide" as used herein refers to any peptide, including an oligopeptide, a polypeptide and a protein. Besides the amino acid chain the term "peptide" also includes any co- and post-translational modification thereof, such as glycosylation, methylation, acetylation, phosphorylation, sulfatation, deamidation, ubiquitinylation etc. Where the expression "peptide and/or a protein" is used herein, it is thus intended as a clarification that the corresponding molecule may also be a protein and not only an oligo- or polypeptide. In embodiments where the binding partner is or includes a peptide (such as a protein) the binding partner of the target molecule may be suspected to be included in a plurality of peptides and/or proteins. Within this plurality of peptides and/or proteins the respective binding partner is to be identified. Accordingly the method of the invention can be used as a screening method (cf also above), for example for screening a library of peptides and/or proteins. Typically a method according to the invention includes selecting as well as providing the plurality of peptides and/or proteins that is suspected to include the binding partner of the target molecule. In some embodiments the plurality of peptides and/or proteins also includes the target molecule. In some embodiments the target molecule is added to the plurality of peptides and/or proteins. In embodiments where the target molecule is a peptide or a protein the target molecule is in some embodiments included in the plurality of peptides and/or proteins that are suspected to include a binding partner of the target molecule. In embodiments where the target molecule is a nucleic acid molecule the method is in some embodiments a screening method of determining whether the nucleic acid molecule forms a complex or interacts with any of a plurality of peptides and/or proteins.

When provided or when formed, each member of the plurality of peptides and/or proteins is in some embodiments physically combined with a member encoding nucleic acid molecule. In some embodiments a corresponding physical combination may also be formed in the course of carrying out the method of the invention. In such embodiments the peptides and/or proteins are not yet physically combined with a member encoding nucleic acid molecule when provided. However, in any case a physical combination of each member of the plurality of peptides and/or proteins and the corresponding member encoding nucleic acid molecule exists or is established at one point of time. This point of time is typically defined by allowing a pair of nucleic acid molecules to be linked. This pair of nucleic acid molecules is or corresponds to the nucleic acid molecules that encode a target molecule and its binding partner, when the target molecule and its binding partner form a complex (see also below). After linkage of the two nucleic acid molecules the physical combination may be released. In some embodiments a peptide or protein encoded by a member encoding nucleic acid molecule is denatured, disrupted or destructed. This occurs for example in embodiments where the composite nucleic acid molecule of target labeling and analyte labeling nucleic acid molecules (or member encoding nucleic acid molecules, as the case may be) is formed by means of a PCR technique (see below). Thereby a complex between target molecule and analyte molecule may likewise be disrupted or cease to exist. In such embodiments a physical combination of the respective nucleic acid molecule and a complex between target and analyte molecule may accordingly be released due to disintegration of the complex and/or due to destruction of one or both binding partners of the complex between target and analyte molecule.

The physical combination may take a variety of embodiments such as spatial combination, combination by a common defined phase or combination via attractive forces including a chemical bond. The peptide/protein may for instance be linked to a member encoding nucleic acid molecule, which may be a linkage in cis. This member encoding nucleic acid molecule includes a sequence that encodes the respective member of the plurality of peptides and/or proteins. Accordingly, each of the peptides and/or proteins, one or more of which are suspected to be capable to form a complex with the target molecule, is coupled to a sequence encoding it on a nucleic acid molecule.

Each member of the plurality of peptides and/or proteins may be physically combined with the corresponding member encoding nucleic acid molecule by any desired combination. The means of combining each of the members with the corresponding member encoding nucleic acid molecule may be independently selected for each of the members. In some embodiments all of the members are physically combined with their member encoding nucleic acid molecule via the same means. Examples of a suitable physical combination between a peptide and/or protein and a member encoding nucleic acid molecule include, but are not limited to, a covalent bond, a non-covalent bond, a linking molecule, a cell, a virus, a phage and a ribosome (cf. also FIG. 1). A linking molecule may be any desired molecule such as a peptide, a low molecular weight organic compound, an oligomeric or polymeric organic compound such as polyethyleneglycol, a nucleic acid molecule, a lipid molecule or an oligo- or polysaccharide.

Where a cell provides the physical combination any cell may be used in the method of the invention. The cell may be prokaryotic or eukaryotic. Examples of a suitable prokaryotic host include, but are not limited to bacteria such as *E. coli, Bacillus* (e.g. *B. subtilis*), *Pseudomonas, Salmonella*, and *Serratia*. Prokaryotic hosts are, generally, very efficient and convenient for the expression of heterologous peptides/proteins. However, in terms of expression (see also below) certain posttranslational modifications such as glycosylation require the expression of additional factors. Examples of eukaryotic hosts include, but are not limited to, yeast, fungi, insect cells, mammalian cells, for instance in tissue culture. In terms of expression eukaryotic cells such as yeast provide substantial advantages in that they can also carry out post-translational modifications. Yeast such as *S. cerevisiae* for instance recognizes leader sequences on cloned mammalian genes and secretes peptides bearing leader sequences (i.e., pre-peptides). The cell may also be a somatic cell. A somatic cell may be a cell of any tissue, such as for instance skin, kidney, spleen, adrenal, liver, lung, ovary, pancreas, uterus, stomach, colon, small intestine, spleen, bladder, prostate, testicular, thymus, muscle, connective tissue, bone, cartilage, vascular tissue, heart, eye or neural tissue. A somatic cell may be obtained, derived or isolated from a respective tissue. The cell may be directly taken from a respective host organism in form of a sample such as e.g. a biopsy or a blood sample. It may also have been derived from a host organism and subsequently been cultured, grown, transformed or exposed to a selected treatment. It may also be a cell of a cell line. A large variety of mammalian cell lines are for example available in the art. Methods according to the invention where a cell is used, e.g. as a host cell, and/or to provide a physical combination as explained above, generally include providing a plurality, e.g. a population, of a suitable cell. As also explained below, in some embodiments a plurality of cell may also be a collected ("picked") colony of cells. A plurality of cells providing the above detailed physical combination may also be provided in the form of a cell library, which may be ready to be used in the method of the invention.

In some embodiments each member of the plurality of analyte molecules, e.g. analyte peptides and/or proteins, is physically combined with a member encoding nucleic acid molecule by means of spatial combination. In such embodiments typically a confined circumferential space with defined borders encompasses both the respective analyte molecule (e.g. protein/peptide). An illustrative example of such spatial combination is a cell. Into a suitable cell a nucleic acid molecule may be introduced and a peptide/protein encoded by a sequence included in the nucleic acid molecule may be expressed in the cell.

As already indicated above, the peptides and/or proteins may for example carry the sequence encoding them on a connected nucleic acid molecule. Where in such embodiments a physical linkage is provided the potential binding partner of the target molecule may be provided in the form of a member of a plurality of hybrid molecules, which include both a nucleic acid moiety and a peptide and/or protein moiety. Such a hybrid molecule may include one or more other nucleic acid sequences as well as one or more additional moieties including a further peptide and/or protein moiety. An example of such a further peptide and/or protein moiety is a peptide linker or a protein linker, which may connect the member encoding nucleic acid molecule to the peptide or protein that is a member of the plurality of potential binding partners of the target molecule.

In some embodiments a physical link serves as the physical combination of peptide/protein or other analyte molecule and corresponding labelling, including encoding, nucleic acid molecule. In such embodiments a covalent bond may be formed between a member encoding nucleic acid molecule and a peptide and/or protein. Such a covalent bond may for example be obtained by using a nucleic acid molecule with one or more modified bases or a nucleic acid molecule modified at one end, such as a 5'-thiolated nucleic acid molecule. A 5'-end of a member encoding nucleic acid molecule (Olejnik, J., et al., *Nucleic Acids Research* (1999) 27, 23, 4626-4631) or the 2'-position of a nucleotide therein at a selected position (Zatsepin, T. S., et al., *Tetrahedron Lett*. (2005) 46, 3191-3195) may also be linked to a phosphoramidite moiety, which may be, via a reactive functional group, covalently linked to a corresponding peptide or protein. In this way a photocleavable linkage can be provided as described by Olejnik et al. (1999, supra). A further example of a modified base that may be used for a covalent linkage to a peptide or a protein is 5'-amino-5'-deoxythymidine, which may be obtained from thymidine and tetrachlorophtalimide as described by Tetzlaff et al. (*Tetrahedron Lett*. (1998) 39, 4215-4218). By converting it to its 5'-methoxytrityl protected 3' phosphoramidite this base has one residue available for coupling to a nucleic acid molecule and one residue for coupling to a peptide or protein (ibid.). A nucleic acid molecule may also be linked to an alkyne terminated moiety and covalently linked to a peptide or protein carrying a 4-azidoprolyl group in a [3+2] cycloaddition reaction known to those skilled in the art as the 'click-reaction'. This approach has been demonstrated by Gogoi et al. (*Nucleic Acids Research* (2007) 35, 21, e139) for the coupling of a peptide to a PNA molecule.

A covalent bond between a member encoding nucleic acid molecule and a peptide and/or protein may also be obtained by using a PNA molecule as the nucleic acid molecule. Typically a PNA molecule contains repeated N-(2-aminoethyl) glycin units. The bases are typically attached via methylenecarbonyl linking groups. One or more of the glycin units, for instance a terminal one, may be exchanged for an amino acid with a functional group and thus serve to link a peptide or protein chain.

As another example a nucleic acid molecule covalently coupled to an aminonucleoside antibiotic such as puromycin or A201A may be provided. A member encoding RNA molecule with an aminonucleoside antibiotic, e.g. puromycin group, at its 3'-end may for instance be formed in in vitro translation (e.g. Kurz, M., et al., *ChemBioChem* (2001) 2, 666-672). This peptidyl-acceptor antibiotic is thereby covalently linked to the polypeptide chain grown at the ribosome particle. In some embodiments a replication initiator protein from the *E. coli* bacteriophage P2 may be used in the formation of a covalent linkage between the member of the plurality of peptides and/or proteins and the nucleic acid molecule encoding the same. The replication initiator typically replicates by attaching the P2A protein to its ownDNA. P2A is an endonuclease that binds to the viral origin and introduces a single-strand break, a "nick", in the nucleic acid molecule and attaches to the molecule of DNA from which it has been expressed. The sequence of a peptide/protein linked to P2A can thus be synthesized in vitro and become covalently attached to its own coding DNA.

As a further example, a pair of specifically interacting moieties such as the biotin/(strept)avidin pair may be used to physically link the member encoding nucleic acid molecule and the encoded peptide or protein. The well-known system of biotin and avidin or streptavidin has for example been briefly reviewed by Wilchek et al. (*Immunol. Lett*. (2006) 103, 27-32). In one embodiment a 5'-thiolated member encoding nucleic acid molecule may be coupled to streptavidin using standard protocols (see Doi et al., *Journal of Biotechnology* (2007) 131, 231-239 and references cited therein as an example). A corresponding peptide or protein may be linked to biotin. Upon adding the streptavidin-conjugated member encoding nucleic acid molecule and the biotin-conjugated peptide or protein a complex between biotin and streptavidin forms, thereby physically linking the member encoding nucleic acid molecule and the corresponding peptide or protein. A biotinylated nucleic acid molecule may for example be linked to a protein or peptide that includes streptavidin.

In some embodiments a member of the plurality of peptides and/or proteins may be physically, e.g. covalently linked to an oligonucleotide that hybridises to a terminal sequence of a strand of the member encoding nucleic acid molecule, for instance as exemplified above. Following providing a single stranded member encoding nucleic acid molecule a corresponding peptide or protein may then be coupled thereto. In this regard other antibiotics such as aminoglycoside antibiotics may also be provided. Examples of an aminonucleoside antibiotic include, but are not limited to, amikacin, gentamicin, kanamycin, tobramycin, neomycin, netilmicin, neamine, paromomycin, monomycin, streptomycin, ribostamycin, lividomycin and apramycin. Such antibiotics however do generally not resembles the 3' end of the aminoacylated tRNA and are thus not transferred to the growing peptide chain at the ribosome. Rather they inhibit the translocation of the peptidyl-tRNA at the ribosome. They may nevertheless be covalently linked to a nucleic acid molecule, e.g. via their amino group as described by Charles and Arya (*Journal of Carbohydrate Chemistry* (2005) 24, 145-160). If a further functional group is introduced into the aminonucleoside antibiotic it may be linked to a peptide or protein via this further functional group and thus serve as a linker molecule.

In some embodiments the peptide or protein may be linked to a nucleic acid molecule that is capable of hybridizing to the member encoding nucleic acid molecule, for example a cDNA molecule. Such an embodiment may be useful where the member encoding nucleic acid molecule is of relatively low stability under typical laboratory conditions, for instance where the member encoding nucleic acid molecule is a RNA molecule. An illustrative example of a suitable technique in this regard has been disclosed by Yamaguchi et al. (*Nucleic Acids Research* (2009), doi:10.1093/nar/gkp514).

In some embodiments the peptide or protein may be linked to an aptamer. An aptamer is a nucleic acid molecule that can be selected from a random nucleic acid pool based on its ability to bind a selected other molecule. In some embodiments the peptide or protein may be linked to a linker peptide or a linker protein. Such a linker peptide or linker protein may include a peptide bound by an aptamer. Such a linker peptide or linker protein may also include or be an antibody, a fragment thereof or a proteinaceous binding molecule with antibody-like functions, which binds to an aptamer.

Examples of (recombinant) antibody fragments are Fab fragments, Fv fragments, single-chain Fv fragments (scFv), diabodies, triabodies (Iliades, P., et al., *FEBS Lett* (1997) 409, 437-441), decabodies (Stone, E., et al., *Journal of Immunological Methods* (2007) 318, 88-94) and other domain antibodies (Holt, L. J., et al., *Trends Biotechnol.* (2003), 21, 11, 484-490). Single-chain Fv fragments are for instance fusions of variable regions from one heavy chain and one light chain of an immunoglobulin molecule. An example of a proteinaceous binding molecule with antibody-like functions is a mutein based on a polypeptide of the lipocalin family (WO 2003/029462; WO 2005/019254; WO 2005/019255; WO 2005/019256; Beste et al., *Proc. Natl. Acad. Sci. USA* (1999) 96, 1898-1903). Lipocalins, such as the bilin binding protein, the human neutrophil gelatinase-associated lipocalin, human Apolipoprotein D, human tear lipocalin, or glycodelin, posses natural ligand-binding sites that can be modified so that they bind to selected small protein regions known as haptens. Other non-limiting examples of further proteinaceous binding molecules so-called glubodies (see WO 96/23879), proteins based on the ankyrin scaffold (Mosavi, L. K., et al., *Protein Science* (2004) 13, 6, 1435-1448) or the crystalline scaffold (WO 2001/04144), the proteins described by Skerra (*J. Mol. Recognit.* (2000) 13, 167-187), AdNectins, tetranectins, avimers and peptoids. Avimers contain so called A-domains that occur as strings of multiple domains in several cell surface receptors (Silverman, J, et al., *Nature Biotechnology* (2005) 23, 1556-1561). Adnectins, derived from a domain of human fibronectin, contain three loops that can be engineered for immunoglobulin-like binding to targets (Gill, D. S. & Damle, N. K., *Current Opinion in Biotechnology* (2006) 17, 653-658). Tetranectins, derived from the respective human homotrimeric protein, likewise contain loop regions in a C-type lectin domain that can be engineered for desired binding (ibid.). Peptoids, which can act as protein ligands, are oligo(N-alkyl) glycines that differ from peptides in that the side chain is connected to the amide nitrogen rather than the a carbon atom. Peptoids are typically resistant to proteases and other modifying enzymes and can have a much higher cell permeability than peptides (see e.g. Kwon, Y.-U., and Kodadek, T., *J. Am. Chem. Soc.* (2007) 129, 1508-1509). Where desired, a modifying agent may be used that further increases the affinity of the respective moiety for any or a certain form, class etc. of target matter.

Any form of antibody, antibody fragment or proteinaceous binding molecule with antibody-like functions may be selected to obtain a linker peptide for physically linking the member encoding nucleic acid molecule and the peptide or protein. A conventional display technology (supra) may be used to generate such an antibody, antibody fragment or proteinaceous binding molecule. Li et al. (*Organic & Biomolecular Chemistry* (2006), 4, 3420-3426) have for example demonstrated how a single-chain Fv fragment capable of forming a complex with a selected DNA adapter can be obtained using phage display.

In some embodiments the linker peptide or linker protein may include or be a methyltransferase, such as M.Hae III of *Haemophilus aegypticus*, M.Ha I of *Haemophilus haemolyticus*, M.Hpa I of *Haemophilus parainfluenzae*, M.Msp I of *Moraxella* species, Alu I of *Arthrobacter luteus*, or a methyltransferase domain, e.g. of M.Hae III. Methyl transferases are known to bind in vitro to nucleic acid molecules with high stability.

Hae III DNA methyltransferase is for example capable of forming a covalent bond with nucleic acid molecules that include the sequence 5'-GGCC-3' or 5'-GGFC-3' (F=5-fluoro-2'-deoxycytidine). The sequence specificity of this enzyme may be altered by means of genetic engineering and directed evolution as described by Cohen et al. (Protein Engineering, Design & Selection (2004) 17, 1, 3-11). In some embodiments the linker peptide or linker protein may include or be the replication initiator protein of *E. coli* bacteriophage P2A. This enzyme has a cis-nicking activity and becomes linked to the 5'-end of the nicked nucleic acid molecule (Liu, J., et al., *Journal of Molecular Biology* (1993) 231, 2, 361-374; indicated also in Kurz, M., et al., ChemBioChem (2001) 2, 666-672).

This physical linkage between the member encoding nucleic acid molecule and the member of the plurality of peptides and/or proteins may also be formed via the formation of a complex with a ribosome (He, M., & Taussig, M. J., *Briefings in Functional Genomics and Proteomics* (2002) 1, 2, 204-212; Yan, X., & Xu, Z., *Drug Discovery Today* (2006) 11, 19/20, 911-916). For example a complex of an RNA molecule with a ribosome and a nascent peptide or protein may be formed by ribosome stalling using an antibiotic such as rifampicin, chloramphenicol or cycloheximide. As a further example, the stop codon of an RNA molecule may be removed—or replaced by a spacer such as the immunoglobulin Cκ domain—in order to form the complex of RNA molecule, ribosome and peptide or protein (see Zhand, C., et al., *Nature Methods* (2007) 4, 3, 269-279, or He, M., & Taussig, M. J., *Nature Methods* (2007) 4, 3, 281-288 for exemplary procedures).

Its formation may for example include or be the inclusion in a bacteriophage or into a virus particle, such as a retrovirus, a baculovirus, an adeno-associated virus or a hepatitis virus. Such techniques are well known to those skilled in the art under the names "phage display" and "virus display" (for an overview see e.g. Benhar, I., *Biotechnology Advances* (2001) 19, 1-33 or Dani, M., *J. of Receptor & Signal Transduction*

*Research* (2001) 21, 4, 469-488). They trace back to a method of mapping epitope-binding sites of antibodies by panning random peptide-phage libraries on immobilized immunoglobulins. As an example, a filamentous phage may be used, which replicates and assembles in a host cell such as *E. coli* without killing the same. In some embodiments each member of the plurality of peptides and/or proteins is expressed as a fusion protein with a phage coat protein. The member of the plurality of peptides and/or proteins is thus incorporated into phage particles along with the nucleic acid molecule encoding the displayed fusion protein. In some embodiments a helper phage may be used, for example if the member of the plurality of peptides and/or proteins is too large for the phage protein to maintain its function. The respective helper phage may provide one or more, including all, proteins required for replication of the phage used. This technique is therefore also known to those skilled in the art as "phage rescue".

The corresponding physical linkage between the member encoding nucleic acid molecule and the member of the plurality of peptides and/or proteins may also be formed via an entire cell, on the surface of which the respective peptide/protein is situated. Such techniques are known to those skilled in the art under the name "cell surface display" (for a partial overview, see e.g. Benhar, I., 2001, supra). As an illustrative example, a cell may be transfected with a nucleic acid encoding a fusion protein that includes the member of the plurality of peptides and/or proteins and a cell surface protein (e.g., a receptor). Any cell may be used for this purpose, such as a bacterial cell, a yeast cell, an insect cell and a mammalian cell. It is noted that in embodiments where a baculovirus is used for the virus display technique (supra), typically both the virus itself and infected insect cells are capable of presenting the respective member of the plurality of peptides and/or proteins. In embodiments where a Gram-negative bacterium is selected, an outer membrane protein may for instance be selected for the formation of a fusion protein with a member of the plurality of peptides and/or proteins. It is noted in this regard that a physical combination, generally not being a physical linkage, is also provided by expressing a protein in a cell, where the protein remains located within the cell.

Technological aspects that may be useful for considerations on the technique to be selected—as well as embodiments thereof—in establishing a physical linkage between a nucleic acid molecule and a peptide/protein have been published in the art, e.g. by Graddis et al. (*Current Pharmaceutical Biotechnology* (2002) 3, 285-297). Where a physical linkage by means of a further molecule is selected, this further molecule may also be linked to a solid phase such as a particle, including a nanoparticle or a magnetic bead (see e.g. Yamaguchi et al., 2009, supra; Horisawa, et al., 2009, supra). A respective further molecule may also carry a detectable label such as a dye (ibid.).

The member encoding nucleic acid molecule may be or include any desired nucleic acid (supra). It may for instance be a DNA molecule or an RNA molecule. As a few examples of a suitable DNA molecule, such a molecule may be of genomic DNA, cDNA, plasmid DNA, cosmid DNA, artificial chromosome DNA, synthetic DNA, phasemid DNA or phagemid DNA. In some embodiments the member encoding nucleic acid molecules may include a spacing sequence that separates the sequence encoding the member peptide or protein from the position to which the member peptide or protein is physically linked.

In some embodiments a method according to the invention includes forming the plurality of peptides and/or proteins. Typically a plurality of member encoding nucleic acid molecules is provided, each of which has a nucleotide sequence that encodes one member of the plurality of peptides and/or proteins to be provided. As noted above, for use in the method of the invention each of the peptides and/or proteins needs to be physically linked to a corresponding member encoding nucleic acid molecule. Accordingly, in some embodiments the nucleotide sequences of the member encoding nucleic acid molecules are expressed to produce their respective protein or peptide. A physical combination such as a physical linkage between the member encoding nucleic acid molecule and the peptide or protein encoded by the same is further allowed to form. This physical combination between the member encoding nucleic acid molecule and the member of the plurality of peptides and/or proteins may be formed via any desired means.

As should be apparent from the above, in some embodiments a nucleic acid molecule used in the invention is capable of expressing a peptide/protein encoded by the nucleic acid molecule. The terms "expression" and "expressed", as used herein, are used in their broadest meaning, to signify that a sequence included in a nucleic acid molecule and encoding a peptide/protein is converted into its peptide/protein product. Thus, where the nucleic acid is DNA, expression refers to the transcription of a sequence of the DNA into RNA and the translation of the RNA into protein. Where the nucleic acid is RNA, expression may include the replication of this RNA into further RNA copies and/or the reverse transcription of the RNA into DNA and optionally the transcription of this DNA into further RNA molecule(s). In any case expression of RNA includes the translation of any of the RNA species provided/produced into protein. Hence, expression is performed by translation and includes one or more processes selected from the group consisting of transcription, reverse transcription and replication. Expression of the protein or peptide of the member of the plurality of peptides and/or proteins may be carried out using an in vitro expression system. Such an expression system may include a cell extract, typically from bacteria, rabbit reticulocytes or wheat germ. Many suitable systems are commercially available. The mixture of amino acids used may include synthetic amino acids if desired, to increase the possible number or variety of proteins produced in the library. This can be accomplished by charging tRNAs with artificial amino acids and using these tRNAs for the in vitro translation of the proteins to be selected. A nucleic acid molecule, such as DNA, is said to be "capable of expressing" a peptide/protein if it contains nucleotide sequences which contain transcriptional and translational regulatory information and such sequences are operably linked to nucleotide sequences which encode the polypeptide (see below). A suitable embodiment for expression purposes is the use of an expression vector as further explained below.

In some embodiments a method of the invention includes providing a library of nucleic acid molecules encoding a plurality of peptides and/or proteins. The library may for instance be a cDNA library. The plurality of peptides and/or proteins that is encoded by the plurality of nucleic acid molecules of the library is suspected to include one or more pairs of binding partners that can be identified by the method of the invention. In some embodiments a method of the invention includes providing a library of nucleic acid molecules (e.g. a cDNA library) encoding a plurality of analyte peptides and/or proteins. The plurality of peptides and/or proteins is suspected to include a binding partner of one or more target peptides or proteins of interest. In such embodiments the method further includes providing one or more nucleic acid molecules that encode the one or more target peptides or proteins. In any such embodiment physically combining members of the library of nucleic acid molecules and analyte peptides and/or proteins can be achieved by introducing a respective nucleic acid molecule into a suitable host cell. In the host cell a respective peptide/protein encoded by the nucleic acid molecule can be expressed.

In embodiments where a library of nucleic acid molecules is provided vectors may be provided with the respective nucleic acids. The term 'vector' refers to a unit such as a molecule or a particle such as a nanoparticle capable of transporting a nucleic acid molecule with which it has been provided, for instance to which it has been linked. Generally the unit is capable of transporting a nucleic acid molecule into a cell. The vector may in some embodiments be or include a nucleic acid molecule. In some embodiments it is a single or double-stranded circular nucleic acid molecule. In some embodiments the vector is a virus. In some embodiments the vector is an expression vector, which may include one or more regulatory sequences and be capable of directing the expression of nucleic acids to which it is operably linked. An operable linkage is a linkage in which a coding nucleotide sequence of interest is linked to one or more regulatory sequence(s) such that expression of the nucleotide sequence sought to be expressed can be allowed. Thus, a regulatory sequence operably linked to a coding sequence is capable of effecting the expression of the coding sequence, for instance in an in vitro transcription/translation system or in a cell when the vector is introduced into the cell. A respective regulatory sequence need not be contiguous with the coding sequence, as long as it functions to direct the expression thereof. Thus, for example, intervening untranslated yet transcribed sequences may be present between a promoter sequence and the coding sequence and the promoter sequence can still be considered "operably linked" to the coding sequence.

The term "regulatory sequence" includes controllable transcriptional promoters, operators, enhancers, silencers, transcriptional terminators, 5' and 3' untranslated regions which interact with host cellular proteins to carry out transcription and translation and other elements that may control gene expression including initiation and termination codons. The regulatory sequences can be native (homologous), or can be foreign (heterologous) to the cell and/or the nucleotide sequence that is used. The precise nature of the regulatory sequences needed for gene sequence expression may vary from organism to organism, but shall in general include a promoter region which, in prokaryotes, contains both the promoter (which directs the initiation of RNA transcription) as well as the DNA sequences which, when transcribed into RNA, will signal synthesis initiation. Such regions will normally include those 5'-non-coding sequences involved with initiation of transcription and translation, such as the TATA box, capping sequence, CAAT sequence, and the like. These regulatory sequences are generally individually selected for a certain embodiment, for example for a certain cell to be used. The skilled artisan will be aware that proper expression in a prokaryotic cell also requires the presence of a ribosome-binding site upstream of the gene sequence-encoding sequence.

Where the vector is a nucleic acid molecule it may for example be or include a natural or synthetic single or double stranded prokaryotic vector. Illustrative examples of a prokaryotic vector are a plasmid or viral nucleic acid molecule, or any other nucleic acid molecule, such as for instance a YAC, a BAC, a bacteriophage-derived artificial chromosome (BBPAC), a cosmid or P1 derived artificial chromosome (PAC), that can be transfected or transformed into cells and replicate independently of, or within, the host cell genome. Illustrative examples of E. coli viral vectors include the lambda vector system gt11, gt WES.tB, Charon 4, illustrative examples of E. coli plasmid vectors pBR322, pBR325, ColE1, pSC101, pACYC177, pACYC1084, πVX, pUC8, pUC9, pUC18, pUC19, pLG339, pR290, pKC37, pKC101, SV 40, pBluescript II SK+/− or KS+/−, pQE, pIH821, pGEX, pET series, and any derivatives thereof. Three illustrative examples of Bacillus plasmids are pC194, pC221, and pT127. A suitable Streptomyces plasmid is 0.1101, and a streptomyces bacteriophages φC31. Examples of an eukaryotic plasmid include, but are not limited to, BPV, vaccinia, SV40, 2-micron circle, or their derivatives.

A circular double stranded vector can be linearised by treatment with an appropriate restriction enzyme based on the nucleotide sequence of the vector. A nucleic acid can be inserted into a vector by cutting the vector with a restriction enzyme and subsequently ligating the fragments together. Generally, a vector can be autonomously replicated in a cell (e.g. an episomal vector), or can be integrated into the genome of a cell, and replicated along with the host genome (e.g. a non-episomal mammalian vector). Integrating vectors may have at least one sequence homologous to a host, e.g. bacterial, chromosome that allows for recombination to occur between homologous DNA in the vector and the host chromosome. Integrating vectors can also include bacteriophage or transposon sequences. Episomal vectors such as plasmids are circular double-stranded DNA loops into which additional DNA segments can be ligated.

A vector as used in the present embodiment of a method according to the invention is provided with a nucleic acid sequence that encodes one member of a pair of complementing moieties. The two complementing moieties of the pair complement each other when brought into close physical proximity, i.e. without being brought in connection with each other. The term "close physical proximity" refers to a distance between the two complementing moieties that is below half, including below a quarter, below an eighth or further below, of the three-dimensional width of the smaller of the two respective moieties. Typically close physical proximity refers to a distance in nanoscale dimensions or below, including a distance in dimensions of chemical functional groups or below.

Together the two complementing moieties define a reporter factor. The reporter factor generally provides information to distinguish an instance or a cell in which the reporter factor has been formed from an instance or a cell where no reporter factor has been formed. The reporter factor, which may in some embodiments be a protein, may for instance effect a detectable signal, effect the phenotype of a cell or affect, including effect, the survival of a cell. In some embodiments the reporter factor is a factor that is capable of activating the expression of a protein. The protein may then in turn effect a signal and/or affect the phenotype of a respective host cell. In some embodiments the first and the second complementing moieties are two fragments, which may for instance define two domains of the reporter factor. A detectable signal may, without being limited thereto, be a colour, fluorescence, luminescence, expression of a marker, cell viability, relief of a cell nutritional requirement, cell growth or drug resistance.

As a further illustrative example, protein-fragment complementation based on the enzyme dihydrofolate reductase may be employed. In this protein-fragment complementation two peptides/proteins, being potential binding partners, are fused to complementary fragments of dihydrofolate reductase and expressed in a cell. Where the two complementing moieties complement each other to form dihydrofolate reductase the cell survives and grows in a selective medium (Pelletier, J. N., et al., *Proc. Natl. Acad. Sci. USA* (1998) 95, 12141-12146). A further example is the use of complementary fragments of the catalytic domain of the enzyme *Bordetella pertussis* adenylate cyclase (Karimova, G, et al., *Proc. Natl. Acad. Sci. USA* (1998) 95, 5752-5756). Two peptides/proteins, suspected to define a pair of binding partners, are fused to adenylate cyclase fragments. Complementation results in cAMP synthesis, which gives rise to a particular, identifiable phenotype. Yet a further suitable example described in U.S. Pat. No. 6,270,964 is beta-galactosidase complementation.

Accordingly, where a respective reporter factor is to be formed in a method according to the invention, two vectors are used. The first vector has, e.g. contains, is coupled to or includes, a nucleic acid sequence that encodes a first complementing moiety. The second vector has a nucleic acid sequence that encodes a second complementing moiety. The formation of a reporter factor can occur when the two peptides/proteins encoded by the vectors have been formed. If this is the case, formation of a reporter factor can occur when the two complementing moieties are brought into close physical proximity. This may be the case if the two complementing moieties are coupled to a pair of binding partners that form a complex with each other. In this regard, as indicated above, a vector used in the present embodiment is, in the course of carrying out the method of the invention, provided with a nucleic acid sequence that encodes one of a plurality of peptides and/or proteins, which are suspected to include pairs of binding partners.

In embodiments where a library of nucleic acid molecules is provided that encode a plurality of peptides/proteins among which a pair of binding partners is suspected, the two vectors provided in the method according to the invention each have a nucleic acid sequence that encodes one of the plurality of peptides/proteins. Accordingly the first vector has a nucleic acid sequence that encodes the first complementing moiety and a nucleic acid that encodes one of the plurality of peptides/proteins. In embodiments where a library of nucleic acid molecules is provided that encode a plurality of analyte peptides/proteins among which a binding partner of a target peptide/protein is suspected the first vector has a nucleic acid sequence that encodes one of the plurality of analyte peptides/proteins. The first vector further has a nucleic acid sequence that encodes the first complementing moiety. The second vector has a nucleic acid sequence that encodes the target peptide/protein. The second vector further has a nucleic acid sequence that encodes the second complementing moiety.

In some embodiments where a library of nucleic acid molecules is provided that encode a plurality of peptides/proteins among which a pair of binding partners is suspected a plurality of molecules of a first plasmid and a plurality of molecules of a second plasmid is provided. The first plasmid encodes a first complementing moiety, and the second plasmid encodes a second complementing moiety. When brought into close physical proximity the expressed first and second complementing moieties together define a reporter factor (supra). Into each plasmid molecule of the two pluralities of molecules of a first and of a second plasmid a single nucleic acid molecule of the library of nucleic acid molecules is inserted, i.e. one molecule of the nucleic acid molecules that encode the plurality of peptides and/or proteins.

In some embodiments where a library of nucleic acid molecules is provided that encode a plurality of analyte peptides/proteins among which a binding partner of a target peptide/protein is suspected a plurality of molecules of a first plasmid and a plurality of molecules of a second plasmid is likewise provided. Again, the first plasmid encodes a first complementing moiety, and the second plasmid encodes a second complementing moiety. In these embodiments into each plasmid molecule of the plurality of molecules of the first plasmid a single nucleic acid molecule of the library of nucleic acid molecules is inserted, which encode the plurality of analyte peptides/proteins. Thus each of the first plasmids carries a sequence encoding one of the analyte peptides/proteins. It also carries a sequence encoding the first complementing moiety. Into each plasmid molecule of the plurality of molecules of the second plasmid one nucleic acid molecule is inserted that is a molecule encoding the, or a, target peptide/protein. Hence, each of the second plasmids carries a sequence encoding a target peptide/protein as well as a sequence encoding the second complementing moiety.

The vectors are then in both of the above embodiments introduced into suitable host cells. This may be achieved using any technique known in the art. Vectors may be introduced into cells via transformation, in particular transduction, conjugation, transfection, mobilization or electroporation, to name a few examples. As an illustrative example, a suitable technique of stably introducing the vector into a plant cell is the use of *Agrobacterium tumefaciens* or *Agrobacterium rhizogenes* as a vector, with which the plant cell is infected. A further illustrative example of introduction into a plant cell is fusion of protoplasts with other entities, either minicells, cells, lysosomes or other fusible lipid-surfaced bodies.

As noted above, in some embodiments of a method according to the invention serves in identifying a binding partner of one or more peptides and/or proteins. The plurality of peptides/protein linked to the nucleic acid molecules encoding the same is contacted with the binding partner or with a sample (supra) such as a medium suspected to contain the binding partner. A mixture is thereby formed that includes both the plurality of peptides/proteins and the binding partner/target molecule. In embodiments where the method is a method of identifying a binding partner of at least two target molecules within a plurality of analyte molecules (including of peptides/proteins) a mixture is formed that includes both the plurality of peptides/proteins and the binding partner/target molecule. Unless a respective mixture is already provided (or binding partners are to be identified within one plurality of analyte molecules/peptides) in the method, forming the mixture is carried out by contacting the at least two target molecules with the plurality of analyte molecules. As described above, in some embodiments the method is a method of identifying a binding partner of at least two target molecules within a plurality of analyte peptides and/or proteins. In such embodiments providing at least one nucleic acid molecule encoding the at least one target peptide or protein is accordingly carried out by providing at least two nucleic acid molecules. Each of these nucleic acid molecule encodes one of the at least two target peptides or proteins.

In other embodiments the plurality of peptides and/or proteins is suspected to include one or more pairs of binding partners. In such embodiments both binding partners are accordingly a peptide and/or a protein. In such embodiments a complex between the binding partners may already have formed prior to the method of the invention. In one embodiment the complex is allowed to form during the method of the invention.

Other components of the system that may be added may for example include those necessary for transcription and/or translation of sequences of the nucleic acid molecules. These may be selected for the requirements of a specific system from the following: a suitable buffer, an in vitro transcription/replication system and/or an in vitro translation system containing all the necessary ingredients, an enzyme, a cofactor, RNA polymerase, nucleotides, nucleic acids (natural or synthetic), a transfer RNA molecule, a ribosome and an amino acid.

A suitable buffer is one in which all of the desired components of the biological system will be active. Its selection will therefore depend upon the requirements of each specific reaction system. Buffers suitable for biological and/or chemical reactions are known in the art and to a large extent commercially available.

The mixture formed, or—in embodiments where a pair of binding partners is to be identified within a plurality of peptides/proteins—the plurality of peptides/proteins is divided into compartments such as microcapsules. In typical embodiments non-membranous micro-compartmentalization/encapsulation systems based on phase partitioning of an aqueous environment in a colloidal system, such as an emulsion, are used. Hence, a heterogeneous system of two immiscible liquid phases with one of the phases dispersed in the other as droplets of microscopic or colloidal size may be used. Upon dividing the mixture or the plurality of peptides/proteins into compartments exchange of nucleic acid molecules between individual compartments is, at least essentially, prevented. This ensures an isolation of the compartments from other compartments in this regard. At the same time the formation and the composition of the compartments must not dissolve a complex formed between binding partners. Furthermore it may not hamper or prevent the process that is desired to be performed in the compartments such as a PCR or association to a capture probe (see below). A variety of compartmentalisation techniques are available that fulfil these requirements (see e.g. WO 2005/049787 for examples).

As an illustrative example, an emulsion may be formed from any suitable combination of immiscible liquids. Typically the peptides/proteins as well as other biochemical components are provided in an aqueous solution, such that one of the immiscible liquids is in such embodiments aqueous. An illustrative example of a suitable compartmentalisation is the formation of a water-in-oil emulsion. In such an emulsion water is a disperse, internal or discontinuous phase, i.e. the phase present in the form of finely divided droplets. A hydrophobic, typically non-polar, immiscible liquid is the matrix in which these droplets are suspended, i.e. the nondisperse, continuous or external phase. Such emulsions are termed "water-in-oil" (W/O). This has the advantage that the entire aqueous phase containing the biochemical components is compartmentalised in discreet droplets (the internal phase). The external phase, being a hydrophobic oil, generally contains none of the biochemical components and hence is inert.

Numerous examples of liquids that are immiscible with an aqueous phase are known. Such liquids are typically non-polar liquids. Examples of such liquids include, but are not limited to mineral oil, hexane, heptane, cyclohexane, benzene, toluene, dichloromethane, chloroform, carbon tetrachloride, carbon disulfide, dioxane, diethyl ether, diisopropylether, methyl propyl ketone, methyl isoamyl ketone, methyl isobutyl ketone, cyclohexanone, isobutyl isobutyrate, ethylene glycol diacetate, and a non-polar ionic liquid. Examples of a non-polar ionic liquid include, but are not limited to, 1-ethyl-3-methylimidazolium bis[(trifluoromethyl)sulfonyl]amide bis(triflyl)amide, 1-ethyl-3-methylimidazolium bis[(trifluoro-methyl)sulfonyl]amide trifluoroacetate, 1-butyl-3-methylimidazolium hexafluorophosphate, 1-hexyl-3-methylimidazolium bis(trifluoromethylsulfonyl)imide, 1-butyl-3-methylimidazolium bis(trifluoromethylsulfonyl)imide, trihexyl(tetradecyl)phosphonium bis[oxalato(2-)]borate, 1-hexyl-3-methyl imidazolium tris(pentafluoroethyl)trifluorophosphate, 1-butyl-3-methylimidazo hum hexafluorophosphate, tris(pentafluoroethyl)trifluorophosphate, trihexyl(tetradecyl)phosphonium, N"-ethyl-N,N,N',N'-tetramethylguanidinium, 1-butyl-1-methylpyrroledinium tris(pentafluoroethyl)trifluorophosphate, 1-butyl-1-methylpyrrolidinium bis(trifluoromethylsulfonyl)imide, 1-butyl-3-methyl imidazolium hexafluorophosphate, 1-ethyl-3-methylimidazolium bis(trifluoromethylsulfonyl)imide and 1-n-butyl-3-methylimidazolium. Recent approaches yielding additional ionic liquids based on modified imidazolium compounds have been briefly summarized by Giemoth (Angew Chemie Int Edition (2010), 49, DOI: 10.1002/anie.201002393).

Accordingly, a further example of a suitable compartmentalisation is the formation of a water-in-ionic liquid emulsion. In some embodiments the peptides/proteins as well as other biochemical components are provided in an ionic liquid such as ethylammonium nitrate or a dihydrogen phosphate ionic liquid. Various protic ionic liquids may be tested for their suitability as a solvent for carrying out a method of the invention. Protic ionic liquids are formed through the combination of a Brønsted acid and Brønsted base (see Greaves, T. L., & Drummond, C. J., Chem. Rev. (2008) 108, 206-237).

A water-in-oil emulsion may be stabilised by addition of one or more surface-active agents (surfactants). These surfactants are termed emulsifying agents and can act at the water/oil interface to prevent (or at least delay) separation of the phases. Many oils and many emulsifiers are suitable for the generation of water-in-oil emulsions. An illustrative example of a suitable oil is light white mineral oil and a non-ionic surfactant such as sorbitan monooleate and polyoxyethylenesorbitan monooleate. A further example of a surfactant is an anionic surfactant such as sodium cholate and sodium taurocholate. Sodium deoxycholate may for example be used at a concentration of 0.5% w/v, or below. Inclusion of such surfactants can in some cases increase the expression of the peptides/proteins and/or the activity thereof. Addition of some anionic surfactants to a non-emulsified reaction mixture completely abolishes translation. During emulsification, however, the surfactant is transferred from the aqueous phase into the interface and activity is restored. Where desired, addition of an anionic surfactant to a mixture to be emulsified can ensure that reactions proceed only after compartmentalisation.

Subdividing the mixture, or subdividing the plurality of peptides/proteins within which a pair of binding partners is to be identified—and thus typically subdividing the liquid that includes the same—into compartments may include adding a further liquid. In typical embodiments the mixture or the plurality of peptides/proteins within which a pair of binding partners is to be identified is included in a first liquid that is suitable for handling nucleic acid molecules and peptides and/or proteins. In embodiments where a mixture of a plurality of peptides/proteins and a target molecule is formed, the plurality of peptides/proteins may already be included in this first liquid. A second liquid may then be added, which is immiscible with the first liquid. Phase separation may be allowed to occur. As a result two phases may be formed with the first phase being defined by the first liquid and the second phase being defined by the second liquid. The first phase may form a plurality of compartments within the second phase. This may be achieved according to any protocol known in the art. Mixing the two phases may for instance be carried out by adding one phase dropwise to the other phase under stirring. Stirring may continue at a selected speed and for a selected period of time after adding one phase to the other has been accomplished. Thereby a desired size of the compartments may be achieved.

Creation of an emulsion generally requires the application of mechanical energy to force the phases together. Numerous techniques are available in the art in this regard, which utilise a variety of mechanical devices, including stirrers (such as magnetic stir-bars, propeller and turbine stirrers, paddle devices and whisks), homogenisers (including rotor-stator homogenisers, high-pressure valve homogenisers and jet homogenisers), colloid mills, ultrasound and membrane emulsification devices. The compartment size will vary depending upon the precise requirements of any individual selection process that is to be performed according to the present invention. In all cases, there will be an optimal balance between the number of peptides/proteins, the required enrichment and the required concentration of components in the individual microcapsules to carry out the desired process (see below).

Droplets of a respective emulsion may contain various matter that may assist, facilitate, permit and/or enhance a process that is to be carried out in the microenvironment of the droplets. Due to this capability such droplets have previously been termed "micro-reactors" (see Nakano, M., et al., *Journal of Bioscience & Bioengineering* (2005) 99, 3, 293-295).

Two illustrative examples of matter that may assist, facilitate, permit and/or enhance a process that is to be carried out are a capture probe and a ligating factor. A capture probe may for example be or include an antibody, a fragment thereof or a proteinaceous binding molecule with antibody-like functions, which is capable of associating to a complex formed between the two binding partners, such as the target molecule and the binding partner thereof (see above for examples) or the two peptides/proteins defining a pair of binding partners.

In some embodiments upon subdividing the mixture into a plurality of compartments each compartment includes at most about one molecule of the plurality of peptides and/or proteins. In some embodiments each compartment may include at most either about one member or molecule of the plurality of peptides and/or proteins or at most one complex between members/molecules of the plurality of peptides and/or proteins. Hence, in such embodiments any complex formed between binding partners, whether between a target molecule and a member of the plurality of peptides and/or proteins or between two peptides/proteins of the respective plurality, is segregated from the residual peptides and/or proteins.

In some embodiments the physical combination between analyte molecule and analyte labeling nucleic acid molecule and between target molecule and target labeling nucleic acid molecule is provided by a cell. The same may apply accordingly to a plurality of peptides and/or proteins each of which is physically combined with a member encoding nucleic acid molecule. Each of the respective cells has one analyte molecule and one analyte labeling nucleic acid molecule as well as one target molecule and one target labeling nucleic acid molecule (cf. above). In embodiments where a pair of a first and a second binding partner within a plurality of peptides and/or proteins is to be identified a respective cell has at most about one first member of the plurality of peptides/proteins and one second member of the plurality of peptides/proteins as well the corresponding member encoding nucleic acid molecules encoding the first and the second member of the plurality of peptides/proteins. Each cell may thus at most have one complex formed between a pair of binding partners. In such embodiments the corresponding plurality of cells is subdivided into a plurality of compartments. In some embodiments each compartment may include at most one cell that has the corresponding analyte and target molecules, e.g. peptides/proteins, and nucleic acid molecules.

As used herein the term "at most about one" in the context of analyte molecules, target molecules, members of the plurality of peptides and/or proteins, the corresponding labelling nucleic acid molecules, and of cells, is understood against the background of the fact that a distribution of such molecules or cells is Gaussian. A distribution of for example maximally one cell per compartment is accordingly an ideal assumption, which can however only be put into practice in terms of statistical distributions. At most about one complex of members of the plurality of peptides/proteins accordingly defines that the distribution of peptides/proteins is selected in such a way that on average at most one complex of members of the plurality of peptides/proteins can be found in each compartment. Nevertheless some compartments will also have more than one complex of members of the plurality of peptides/proteins. In some embodiments on average less than one complex of members of the plurality of peptides/proteins can be found in each compartment. At most about one cell per compartment likewise defines that the distribution of cells is selected in such a way that on average at most one cell can be found in each compartment. Nevertheless some compartments will also have more than one complex of members of the plurality of peptides/proteins. In some embodiments on average less than one cell can be found in each compartment.

In each individual compartment/microcapsule a process is allowed to occur. In some embodiments the process allowed to occur within each individual compartment/microcapsule includes the association of a capture probe to a complex between a pair of binding partners or a complex between the target molecule and the binding partner thereof. In some embodiments the process includes the formation of a linkage between member encoding nucleic acid molecules between a pair of binding partners. In addition to such a process one or more further processes may be allowed to occur, such as in vitro transcription and coupled transcription-translation. Furthermore, the effective concentration of molecules present in the compartment/microcapsules may be artificially increased by various methods that are well-known to those skilled in the art. These include, but are not limited to, the addition of volume excluding chemicals such as polyethylene glycols (PEG) and a variety of gene amplification techniques, including transcription using RNA polymerases such as those from bacteria such as *E. coli*, an eukaryote or bacteriophage; polymerase chain reaction (PCR); rolling circle amplification (RCA); nucleic acid sequence based amplification (NASBA); ligase chain reaction (LCR); QB replicase chain reaction; loop-mediated isothermal amplification (LAMP); transcription mediated amplification (TMA) and strand displacement amplification (SDA), including genome strand displacement amplification (WGSDA), multiple strand displacement amplification (MSDA), and gene specific strand displacement amplification (GS-MSDA). Gene amplification techniques requiring thermal cycling such as PCR and LCR may be used if the emulsions and the in vitro transcription or coupled transcription-translation systems are thermostable (the coupled transcription-translation systems may for instance be derived or originate from a thermostable organism such as *Thermus aquaticus*).

In some embodiments allowing the linkage of the two nucleic acid molecules of interest that are encompassed in the same compartment, i.e. the two member encoding nucleic acid molecules or the target molecule and the corresponding binding partner, includes ligation of the nucleic acid molecules. In some embodiments the respective linkage is achieved by overlap extension polymerase chain reaction. Overlap extension PCR is a technique that allows the formation of single polynucleotide molecules from smaller fragments. Amplifying the two nucleic acid molecules of interest with primers that have nucleotide sequences that are at least essentially complementary to each other yields nucleic acid molecules that anneal in the at least essentially complementary sequence. Usually each of the two primers has a 5' addition sequence identical to the 3' end of the nucleic acid molecule to be linked thereto. In the presence of a suitable polymerase the two nucleic acid molecules are thus being completed to a nucleic acid molecule that corresponds to a linkage product of the two nucleic acid molecules of interest. Hence, the two nucleic acid molecules are de facto linked to each other.

In some embodiments the internal environment of a compartment/microcapsule may be altered by addition of one or more reagents to the immiscible second phase, e.g. the oil phase, of the emulsion. Such a reagent may diffuse through the immiscible phase to the aqueous compartment. It may be desired to use a reagent that is at least partly water-soluble, such that a proportion thereof is distributed from the immiscible phase to the aqueous microcapsule environment. It may further be advantageous to select a reagent that is at least substantially insoluble in the immiscible second phase. Adding such a reagent into the second immiscible phase may be accompanied by a process that induces mixing, for example by mechanical agitation such as vortexing. Examples of a reagent which may be added via the oil phase include a substrate, a buffering component, an ion and a chelating agent. The internal pH of compartments/microcapsules may also be altered in situ by adding acidic or basic components to the oil phase. Similarly the ionic liquid proton activity, which corresponds to the pH value, of an ionic liquid may be altered.

In some embodiments the internal environment of a compartment/microcapsule is altered by changing a general condition such as the temperature to which the mixture is exposed. Any of the aforementioned changes of the internal environment of a compartment/microcapsule may allow a desired process to occur. A change in pH or temperature may for instance allow for the formation of a complex between a capture probe and the complex formed between two binding partners, whether between a target molecule and a member of the plurality of peptides and/or proteins or between two peptides/proteins of the respective plurality, is segregated from the residual peptides and/or proteins.

In embodiments where a binding partner, which is a peptide or protein, of a member of a plurality of peptides/proteins is identified or where a pair of binding partners within a plurality of peptides/proteins is identified, both binding partners may be physically linked to a nucleic acid molecule encoding the respective peptide/protein (see above). In such embodiments a process that is allowed to occur in the compartments/microcapsules may concern the two nucleic acid molecules. The two nucleic acid molecules may be allowed to be coupled, in particular to be joined to a combined nucleic acid molecule. As indicated above, matter that may assist, facilitate, permit and/or enhance a process allowed to occur out may be a ligating factor. Such a ligating factor, for example an enzyme known as a ligase, may have been added to the mixture before or upon subdividing the mixture into compartments. As a result each compartment may contain at least one ligating factor. If more than one nucleic acid molecule is present within a compartment the ligase may be allowed to link the respective nucleic acid molecules. As noted above, in some embodiments each compartment includes at most about one member of the plurality of peptides/proteins or at most one complex formed between such a peptide/protein and a binding partner. If in such an embodiment no other nucleic acid molecules where present in the mixture than those physically attached to the peptide/protein encoded by them, (supra) then more than one nucleic acid molecule can only be present in a compartment if a complex between two peptides or proteins or a peptide and a protein has been formed, which are both linked to a nucleic acid molecule. Accordingly, in such embodiments only nucleic acid molecules brought together by the formation of a complex between peptides/proteins linked thereto can be linked by the ligating factor. Other nucleic acids linked to a peptide/protein are segregated due to the formation of compartments.

A ligase is well known in the art as an enzyme that joins or "ligates" pieces of nucleic acid molecules as well as strand breaks and gaps. Various ligase enzymes are known in the art. Typically the ligase reaction depends on the presence of ATP (mammalian and viral enzymes) or NAD (bacterial enzymes) as cofactor. In such cases the ligase reaction generally involves the formation of an enzyme-adenylate complex and the transfer of AMP to a nucleic acid to be joined.

The method of the invention further includes allowing the compartments to disintegrate. Where an emulsion has been formed, it may for example be chemically or electrochemically demulsified, or by means of microwaves. During demulsification, for example by adding an emulsion breaker such as a surfactant or a salt, the plurality of compartments is at least largely joined to a single phase. As an illustrative example, the chemical and electrochemical break-up of oil-in-water emulsions with hydrolysing aluminium salts has recently been compared by Cañizares et al. (Journal of Hazardous Materials (2008) 151, 44-51). The compartments such as water-in-oil droplets may also be disintegrated by adding a phase in which the compartments are soluble. Water-in-oil droplets may for instance be disintegrated by adding an external aqueous phase. The phase that does not contain the plurality of peptides including any complex formed with a target molecule/binding partner, which may for example be an oil phase, may have become redundant. Where desired, this phase may be removed. Furthermore, if desired, the mixture formed from the contents of the previous compartments by disintegrating the same may subsequently be separated into compartments again.

Before disintegrating the compartments it may in some embodiments be desired to change the internal environment of the compartments/microcapsules to conditions where the process that has been allowed to occur (supra) can no longer take place. As two illustrative examples, the temperature may be changed or the pH may be shifted. This change of the internal environment of the compartments may be selected in order to avoid the respective process from occurring in an uncontrolled manner, once the compartments disintegrate and the content thereof gets in contact with the content of other former compartments. Other means of preventing the process from occurring may be selected. In some embodiments an inhibitor of a ligating factor or of a capture probe may be introduced. In some embodiments upon allowing the compartments to disintegrate a solution may be added that is of a state, e.g. temperature or pH, or that contains an inhibitor, that prevents the process from occurring, which has been allowed to occur in the compartments.

As explained above, in some embodiments of a method of identifying a pair of a first and a second binding partner a capture probe is added when the compartments are allowed to disintegrate or after allowing the compartments to disintegrate. The capture probe is capable of associating to the complex between the first and the second binding partner. In some of these embodiments retrieving the composite nucleic acid molecule includes allowing the capture probe to associate to the complex between the first and the second binding partner. Retrieving the composite nucleic acid molecule may also include retrieving the capture probe. Thereby the complex between the first and the second binding partner, combined with the composite nucleic acid molecule, is retrieved. Typically the capture probe will be retrieved after it has been allowed to associate to the complex between the first and the second binding partner.

After the plurality of compartments has disintegrated a mixture is formed that includes the former content of the plurality of compartments in a single phase together with any matter that may have been added, such as an inhibitor. In some embodiments the former content of the plurality of compartments may be deprived of a selected factor, such as a ligating factor or an unbound capture probe, i.e. a capture probe that has not formed a complex with a target molecule such as a complex between binding partners (supra). Removal of such a selected factor may be carried out simultaneously with allowing disintegration of the plurality of compartments, for example in order to prevent any undesired reaction of a respective factor with components that are released from other former compartments. In some embodiments the mixture that includes the former content of the plurality of compartments may be formed under conditions, e.g. of pH or temperature, that are known to prevent the above mentioned undesired reaction of a factor. As an illustrative example, a ligating factor that is capable of linking nucleic acid molecules may have a temperature operation range from about 25° C. to about 40° C. This ligating factor may have been present in the compartments formed. It may have been used to link nucleic acid molecules in a compartment that contained a complex of peptides/proteins that define binding partners and that are physically linked to nucleic acid molecules encoding the respective binding partners. In order to prevent such a ligating factor from non-specifically linking nucleic acid molecules released from previous compartments the temperature of the compartments may be brought to a value below 25° C. before allowing the compartments to disintegrate. Thereafter the temperature may, for the same purpose, be kept below 25° C. until the ligating factor is removed from the mixture formed by the disintegration of the compartments.

As noted above, in some embodiments a capture probe has been allowed to associate to a complex between members of the plurality of peptides/proteins or between a member of the plurality of peptides/proteins and a binding partner such as a target molecule out of a plurality of analyte molecules. In order to retrieve such a complex the capture probe is retrieved. In some embodiments any complex bound to the capture probe may then be released for analysis. In some embodiments analysis is carried out without releasing such a complex from the capture probe. In either case one or, where a pair of binding partners with each an attached nucleic acid molecule is to be identified, two member encoding nucleic acid molecules may be bound to the complex to which the capture probe is associated.

In some embodiments nucleic acid molecules linked to a complex between members of the plurality of peptides/proteins or between a member of the plurality of peptides/proteins and a further peptide/protein that is a binding partner have been allowed to be linked to form a composite nucleic acid molecule. This composite nucleic acid molecule is then retrieved, e.g. collected for identification purposes. Retrieving the composite nucleic acid molecule may include carrying out a primer based nucleic acid amplification. A primer based nucleic acid amplification may be carried out using a primer that is complementary to a part of the sequence of the target labeling nucleic acid molecule. Thereby the composite nucleic acid molecule is amplified.

Retrieving the composite nucleic acid molecule may also include adding a capture probe to the mixture (supra). The capture probe is capable of associating to the complex between the target molecule and the binding partner thereof. The capture probe is then retrieved. As a result the complex between the target molecule and the binding partner thereof is retrieved.

In some of these embodiments the primer based nucleic acid amplification is a polymerase chain reaction (PCR) or isothermal amplification. Examples of polymerase chain reaction include, but are not limited to, multiplex PCR, nested PCR and amplification refractory mutation specific (ARMS) PCR (also called allele-specific PCR (AS-PCR). The PCR is carried out by means of a pair of a first and a second primer. The first primer is complementary to a part of the sequence of the member encoding nucleic acid molecule of one of the binding partners, e.g. the first binding partner. The second primer is a universal primer. As a result the composite nucleic acid molecule is amplified. Examples of isothermal amplification, i.e. amplification without the need of a thermocycling apparatus, that may be used include, but are not limited to, strand displacement amplification (SDA), helicase based amplification, rolling circle amplification, loop-mediated isothermal amplification, helicase-dependent amplification and circular helicase-dependent amplification (cf also above).

In some embodiments the amplified composite nucleic acid molecule is purified. The nucleic acid molecule may for example undergo a conventional extraction using a solvent such as phenol and/or chloroform. Other examples of purifying the composite nucleic acid molecule include, but are not limited to, magnetic beads or spin/vacuum-columns. Commercially available reagents and/or kits for purifying nucleic acid molecules may be used (e.g., Promega, Invitrogen, Qiagen, Zymo Research, Genomed). The nucleic acid molecule may also be purified using an electrophoresis technique such as gel electrophoresis. Where desired the purified nucleic acid molecule may be concentrated by a conventional precipitation, using a solvent such as ethanol.

The nucleic acid sequence of the binding partner to be identified, for instance the nucleic acid sequence of the peptide/protein that is a binding partner of the target molecule is determined. In embodiments where both binding partners are linked to a nucleic acid molecule and these nucleic acid molecules have been linked, typically the nucleic acid sequence of both binding partners is identified. If one of the binding partners has already been known, for example where only one known target peptide/protein is used, only the sequence of the other binding partner, which is accordingly to be identified, needs to be determined. In embodiments where more than one pair of binding partners is to be identified simultaneously it is however generally required to determine the nucleic acid sequence of the entire composite nucleic acid molecule. In this way both binding partners of the binding pair are identified and can be allocated as defining a pair of binding partners. Thereby the pair of binding partners can be distinguished from other pairs of binding partners that may be present.

As already indicated above, the method of the present invention also encompasses embodiments where binding partners, e.g. peptides/proteins are used which are not physically linked to, but merely combined with, a nucleic acid molecule. In other embodiments the binding partners (e.g. peptides/proteins) are linked to a nucleic acid molecule, however this nucleic acid molecule is not encoding the binding partner linked thereto. In this regard any nucleic acid molecule can be linked to one or both binding partners as long as it is suitable to unequivocally identify the respective binding partner, to which it is attached. In such embodiments the above explanations likewise apply, the only difference being that the nucleic acid molecule attached to the respective binding partner does not encode the same. As an illustrative example, one or more synthetic or isolated nucleic acid molecules with a known sequence may be selected for its/their use in a method according to the invention. The nucleic acid molecule(s) has/have a known sequence or its sequence is determined before its/their use. The nucleic acid molecule or a selected member of a plurality of nucleic acid molecules may then be attached to a target peptide/protein, of which a binding partner is to be identified. A plurality of analyte peptides/proteins, which are suspected to include a binding partner of a target molecule such as a target peptide/protein, may be linked to nucleic acid molecules in a corresponding manner: For each member of the plurality of analyte peptides/proteins a nucleic acid molecule may be selected. The sequence of each nucleic acid molecule is already known or is determined. Each selected nucleic acid molecule is then linked to the selected peptide/protein. The plurality of peptides/proteins thus labelled with nucleic acid molecules suitable for identifying the peptides/proteins may then be used in the method of the invention. In some embodiments in compartments formed of a mixture with a target peptide/protein, nucleic acid molecules may be linked, e.g. by means of a ligating factor. The plurality of compartments may be disintegrated as described above. Following PCR using a primer specific for the nucleic acid sequence attached to a target peptide/protein the combined nucleic acid molecule may be amplified and sequenced. Thereby the sequence of the nucleic acid molecule attached to the binding partner is identified and accordingly the respective binding partner identified.

In the same manner binding partners within a mixture of peptides/proteins may be identified. As an illustrative example each member of a plurality of peptides/proteins may be linked to selected nucleic acid molecule. The peptides/proteins thus labelled with nucleic acid molecules suitable for identifying the peptides/proteins are combined and the formation of complexes of peptides/proteins is allowed. As long as the nucleic acid molecule(s) used has/have a known sequence or the sequence is determined before its/their use such nucleic acid molecule(s) and each nucleic acid molecule is attached to only one of the suspected binding partners, its nucleotide sequence is suitable for identifying the respective binding partner. Any complexes formed between binding partners can be identified by forming compartments as defined above and by ligating nucleic acid molecules in formed compartments as described above.

Any part of the method of the present invention may be performed in a manual or in an automated way, or in a combination thereof. In some embodiments the entire method of the invention is carried out in a semi-automatic or an automated manner and may be used as for instance a high throughput screening method. Pluralities of binding partners may be provided in the form of or selected from one or more libraries of e.g. molecules or cells. As an illustrative example, such a library may be a collection of various small organic molecules, chemically synthesized as model compounds. Automated distribution of compounds, liquid and reagents, as well as e.g. automated incubators are already well established in the art.

The method of the invention can also be applied to binding partners that are neither a peptide nor a protein. In this regard a binding partner may be any matter that can be linked to a nucleic acid molecule, such as a peptoid, a metabolite, a drug molecule, a drug candidate molecule, a drug metabolite, a lipid, a carbohydrate, a vitamin, a synthetic polymer, a cell, a microorganism, a virus or any combination thereof.

The term "isolating" and "isolation", as used herein, refer to the process of separating an entity from a heterogeneous population, for example a mixture, such that it is free of at least one substance which was present before the isolation process. In typical embodiments isolation refers to purification of an entity at least essentially to homogeneity.

Those skilled in the art will appreciate that the present invention provides the option to allow for embodiments, in which both binding partners, e.g. a protein/peptide and a target molecule, are displayed. This can be carried out in the form of a physical connection of a nucleic acid and binding partner, e.g. protein/peptide. Such an option may be of particular interest for cases where the target molecule is itself a protein or peptide.

The preceding explanations on a method of identifying binding partners that are a peptide or a protein apply to any of the related embodiments of a method of the invention as summarized above. Such methods may be a method of identifying a pair of a first and a second binding partner within a plurality of peptides and/or proteins, a method of identifying a binding partner of a target peptide or protein within a plurality of peptides and/or proteins, a method of identifying one or more pairs of a first and a second binding partner within a plurality of peptides and/or proteins, and a method of identifying a binding partner of at least one target peptide or protein within a plurality of analyte peptides and/or proteins (supra).

In some embodiments a method according to the invention is for instance a method of identifying a binding partner of a target peptide or protein within a plurality of peptides and/or proteins. The above said applies mutatis mutandis to such an embodiment. The target peptide or protein may be included in a member of a first plurality of peptides and/or proteins. The binding partner is suspected to be included in a member of a second plurality of peptides and/or proteins. Each member of the first and the second plurality of peptides and/or proteins is physically combined with a member encoding nucleic acid molecule (supra). The respective member encoding nucleic acid molecule includes a nucleotide sequence encoding the peptide or protein combined therewith. The method includes combining the first and the second plurality of peptides and/or proteins. Thereby a mixture is formed (supra).

This embodiment further includes allowing the formation of a complex between the target peptide or protein and the binding partner thereof. The method also includes subdividing the mixture into compartments. As a result each compartment includes at most about one member or about one complex between members of the combined pluralities of peptides and/or proteins. Further, the method includes allowing the member encoding nucleic acid molecule of the target peptide or protein and the member encoding nucleic acid molecule of the binding partner of the formed complex to be linked. Thereby the method includes forming a composite nucleic acid molecule. The method also includes allowing the compartments to disintegrate.

The present embodiment also includes retrieving the composite nucleic acid molecule. Retrieving the composite nucleic acid molecule may include carrying out a primer based nucleic acid amplification. The primer based nucleic acid amplification is in some embodiments carried out using a primer that is complementary to a part of the sequence of the member encoding nucleic acid molecule that encodes the target peptide or protein. Thereby the composite nucleic acid molecule is amplified. A capture probe may be added to the mixture. This capture probe may be capable of associating to the complex between the target peptide or protein and the binding partner thereof. In such an embodiment the capture probe may be retrieved. Thereby the complex between the target peptide or protein and the binding partner thereof may be retrieved.

As explained above, the primer based nucleic acid amplification may be one of a polymerase chain reaction (PCR) and isothermal amplification. Isothermal amplification may in some embodiments be one of strand displacement amplification (SDA), helicase based amplification and rolling circle amplification. PCR may for instance be carried out using a pair of a first and a second primer. The first primer is complementary to a part of the sequence of the member encoding nucleic acid molecule that encodes the target peptide or protein. The second primer may for example be a universal primer.

Further, the method includes determining the sequence of the composite nucleic acid molecule. Thereby the method includes identifying the binding partner. The method of the present embodiment may further include purifying the amplified composite nucleic acid molecule. Purifying the amplified composite nucleic acid molecule may for instance include extracting the same.

The above explanations on the physical combination likewise apply to the physical combination between the members of the first plurality of peptides and/or proteins and the member encoding nucleic acid molecules. Accordingly, this physical combination may include one of a covalent bond, a non-covalent bond, a linking molecule, a cell, a virus, a phage and a ribosome. A respective cell may for instance be a prokaryotic or a eukaryotic cell. An illustrative example of a suitable eukaryotic cell is a yeast such as *S. cerevisiae*. Two further illustrative examples of a suitable eukaryotic cell are an insect cell such as an Sf9 cell or a fungal cell such as *Aspergillus nidulans*. A respective prokaryotic cell may for instance be one of *E. coli* and *B. subtilis*.

The invention also provides a kit of parts for identifying a binding partner of at least one target peptide or protein within a plurality of analyte peptides and/or proteins. The kit includes one or more containers filled with one or more of the above described molecules or components that can be used in a method according to the invention. Associated with such container(s) there is in some embodiments provided a notice in the form of instructions on how to use the kit to carry out a method according to the present invention. Accordingly, the kit is typically a kit for carrying out one or more methods as detailed above.

The kit includes a nucleic acid molecule that encodes the target peptide or protein, a first primer and a second primer. The first primer is complementary to a part of the sequence of the nucleic acid molecule that encodes the target peptide or protein. The second primer is a universal primer. The nucleic acid molecule that encodes the target peptide or protein is in some embodiments included in a vector. The vector may have a nucleic acid sequence that encodes a first complementing moiety of a pair of a first and of a second complementing moiety. The vector may be a nucleic acid molecule (supra). It may in some embodiments be an expression vector. These first and second complementing moieties are designed such that they complement each other when brought into physical proximity. In complementing each other they together define a reporter factor. The kit may further include a second vector. The second vector has a nucleic acid sequence that encodes the second complementing moiety of the pair of a first and of a second complementing moiety. The kit may also include means for forming a library of nucleic acid molecules encoding the plurality of analyte peptides and/or proteins. In some embodiments the kit also includes a host cell. The host cell may be suitable for expressing a sequence included in or with a vector, e.g. an expression vector.

The invention further provides a kit of parts for identifying a binding partner of a target peptide or protein. The kit includes a plurality of composite nucleic acid molecules. Each composite nucleic acid molecule of the plurality of composite nucleic acid molecules includes the sequence of a first peptide or protein and the sequence of a second peptide or protein. The first peptide or protein and the second peptide or protein define a pair of binding partners, which are capable of forming a complex with each other. The plurality of composite nucleic acid molecules is generally obtainable by carrying out one of the methods described above. In some embodiments it has been obtained by a respective method. The plurality of composite nucleic acid molecules may have any number. It may for example be a library of at least 100 000, at least $10^6$, at least $10^7$, $10^8$, $10^9$, or $10^{10}$, including at least $10^{11}$, at least $10^{12}$ or at least $10^{13}$ nucleic acid molecules.

The kit can be used to carry out a primer based nucleic acid amplification such as PCR (supra). For this purpose the kit includes a universal primer. A second primer, which is not included in the kit, can be selected according to the target peptide or protein of interest. This second primer will need to be at least essentially complementary to a part of the sequence encoding the target peptide or protein. Upon carrying out nucleic acid amplification a composite nucleic acid molecule is amplified that encodes a binding partner of the target peptide or protein of interest. In this regard the kit may include a notice in the form of instructions on how to use the kit to carry out nucleic acid amplification, possibly including recommendations regarding the selection of the second primer that has a sequence matching a part of the sequence of the target peptide or protein (supra). Typically the plurality of composite nucleic acid molecules and the universal primer are included in separate containers within the kit.

In order that the invention may be readily understood and put into practical effect, particular embodiments will now be described by way of the following non-limiting examples. It is understood that modification of detail may be made without departing from the scope of the invention.

Exemplary Embodiments of the Invention

Detailed knowledge of the protein-protein interaction network (also known as the interactome) in a given biological system is crucial to understanding it fully. With the availability of various genomes, the number of known or predicted proteins has grown exponentially. However, functional annotation of these proteins has lagged behind growth in genomic data. In an effort to rectify this situation, multiple groups have carried out genome-wide screens with yeast two-hybrid (Bartel, P. L., et al., Nat Genet (1996) 12, 1, 72-77; Giot, L, et al., Science (2003) 302, 5651, 1727-1736; LaCount, D J, et al., Nature (2005) 438, 7064, 103-107; Li, S, et al., Science (2004) 303, 5657, 540-543; Rain, J C, et al., Nature (2001) 409, 6817, 211-215; Titz, B, et al., PLoS One (2008) 3, 5., e2292; Uetz, P, et al., Science (2006) 311, 5758, 239-242; Parrish, J R, et al Genome Biol (2007) 8, 7, R130; Rual, J F, et al., Nature (2005) 437, 7062, 1173-1178; Stelzl, U, et al., Cell (2005) 122, 6, 957-968; Ito, T, et al., Proc Natl Acad Sci USA (2001) 98, 8, 4569-4574; Uetz, P, et al., Nature (2000) 403, 6770, 623-627), using protein chips (Zhu, H., et al., Science (2001) 293, 5537, 2101-2105) and affinity pull-downs followed by mass spectrometry (Ho, Y., et al., Nature (2002) 415, 6868, 180-183; Gavin, A C, et al., Nature (2002) 415, 6868, 141-147; Krogan, N J, et al., Nature (2006) 440, 7084, 637-643). Among the techniques commonly used to study protein interactions on a genomic level, two-hybrid systems are particularly well suited to high-throughput applications. Typically, arrays or pooled libraries of ORFs fused to an activation domain are mated to cells containing ORFs fused to a DNA-binding domain. In the array method, individual bait proteins are mated in parallel to every member of a pre-defined activation domain-ORF fusion array (Uetz et al., 2000, supra). Interactions are then identified simply by noting the location of the positive diploids. This method is quite laborious however, as it involves mating each bait protein to the activation domain-ORF fusion array one at a time.

In the library based approach, pooled activation domain-ORF fusions are mated to DNA binding domain-ORF fusions, with interacting diploids chosen by growth on selective plates. The identity of the interacting partners is then determined by PCR amplification and sequencing. The reproducibility of the potential interactions identified in the first round is quite variable, ranging from 20% for arrays to 60% and above for libraries (Rual et al., 2005, supra;. Stelzl et al., 2005, supra; Uetz et al., 2000, supra; Terradot, L, et al., Mol Cell Proteomics (2004) 3, 8, 809-819).

Multiple yeast two-hybrid screens have been conducted in various model organisms to discover genomic interaction maps, the first being applied to the T7 bacteriophage (Bartel et al., 1996, supra). Uetz et al. (2000, supra) and Ito et al. (2001, supra) conducted high throughput experiments with most of the ~6000 genes in the *S. cerevisiae* genome, discovering 957 and 4549 interactions respectively. Surprisingly, only limited overlap was found between these interactomes (Ito et al., 2001, supra), likely due to incomplete querying of all possible binary interactions as well as limitations on the number of potential positives that could be economically sequenced (Uetz et al., 2000, supra).

Similar screens have been subsequently carried out for *D. melanogaster* (Giot et al., 2003, supra), *H. pylori* (Rain et al., 2001, supra), *C. elegans* (Li et al., 2004, supra), *P. falciparum* (LaCount et al., 2005, supra) and by two separate groups for humans (Rual et al., 2005, supra; Stelzl et al., 2005, supra), along with other organisms. As with the two yeast studies, unexpectedly little overlap exists between the interactomes uncovered by the two human studies (17 interactions) despite an overlap of about 1000 proteins in their libraries (Rual et al., 2005, supra; Stelzl et al., 2005, supra; Ratushny, V, & Golemis, E, Biotechniques (2008) 44, 5, 655-662). The reasons for this are thought to be insufficient coverage of all possible combinations of gene pairs (each study involves only a fraction of the total number of possible genes in the human genome), a limit being set on the number of positive diploids that were sequenced due to cost considerations in one case (Uetz et al., 2000, supra), contaminating false positives as well as false negatives that are known to occur with the yeast two-hybrid technique (Huang, H, et al., PLoS Comput Biol (2007) 3, 11, e214). The solutions to these problems is to undertake more extensive screens, particularly for larger genomes (such as the human genome), including multiple copies of each gene, possibly split into individual domains, and increasing the number of positive diploids that are sequenced. Such an effort is likely to place great strain on the resources of an individual laboratory.

Another consequence of the rapid increase in the amount of genomic data available is the absence of suitable analytical reagents such as antibodies to investigate the predicted proteome. This is due to the low throughput of conventional antibody development protocols. Many groups have developed novel technologies to address this situation, involving Protein Fragment Complementation Assays (PCAs), selectively infective phage and combinatorial yeast-phage display (Bartel et al., 1996, supra; Rual et al., 2005, supra; Uetz et al., 2000, supra; Jung, S, et al., J Immunol Methods (1999) 231, 1-2, 93-104; Bowley, D R, et al., Proc Natl Acad Sci USA (2009) 106, 5, 1380-1385; Secco, P, et al., Protein Eng Des Sel (2009) 22, 3, 149-58). These techniques rely on simultaneous combinatorial expression of antigen and antibody libraries and conditional enzymatic activity or Fluorescence Activated Cell Sorting (FACS) for selection of cognate pairs. While they are able to generate antibodies much faster than was possible before, these methods too, seem to lack a simple means of storage and transmission of the information generated therein, instead relying on a community wide annotation of the antigen-antibody pairs (Bowley et al., 2009, supra).

To simplify this bottleneck, Hastie and Pruitt (Hastie, A. R, & Pruitt, S C, Nucleic Acids Res (2007) 35, 21, e141) have developed an innovative technique which involves Cre recombinase mediated linkage of interacting genes in vivo. The joining of interacting genes to form a single segment of DNA naturally preserves interaction data. These fused genes can then be pooled without loss of information, and processed in parallel to generate short sequence tags, called binary interaction tags (BI-tags). However, this method will require modification of existing plasmid libraries and strains, and cannot be readily applied to other methods such as combinatorial yeast-phage display (Bowley et al., 2009, supra).

As explained above, a method according to the invention enables genes encoding interacting proteins to be linked in a single segment of DNA. As a result the information from for instance diverse two-hybrid assays can be stored, duplicated and interrogated with ease. In the following examples it is also demonstrate that this technique is applicable in other related contexts such as bacterial two-hybrid systems, and novel formats such as combinatorial yeast-phage display.

Figure 1:
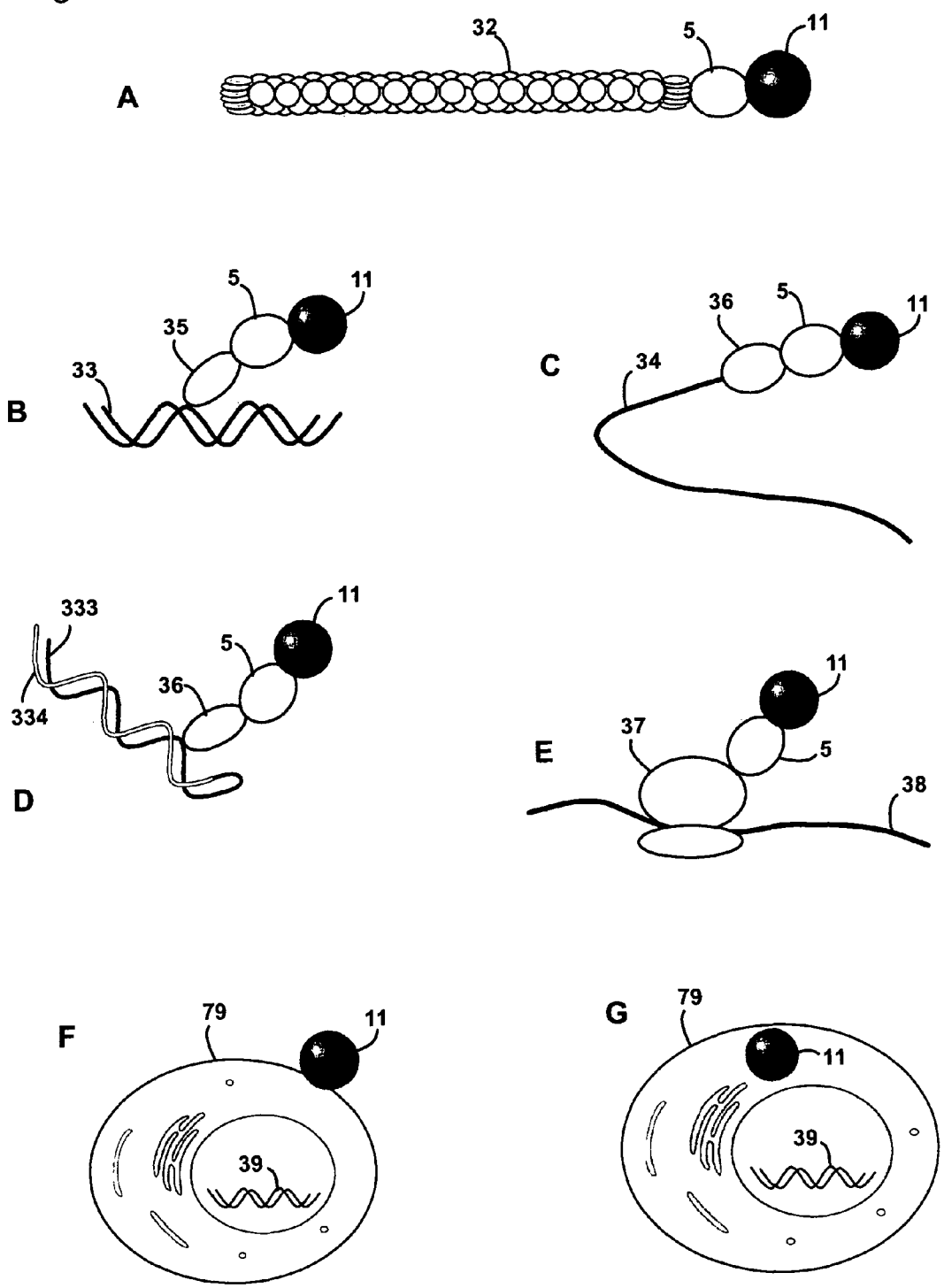
FIG. 1 depicts examples how a peptide or a protein (11) and a nucleic acid molecule encoding the peptide or a protein can be physically combined with each other in an embodiment of the invention. A: virus display; B: DNA display; C: mRNA display; D: cDNA display; E: ribosome display; F: cell display; G: intracellular expression (5: linking peptide; 32: viral vector; 33, 34, 39, 333, 334: encoding nucleic acid molecule; 35: DNA-binding protein; 36: puromycin molecule; 37: ribosome; 38: mRNA; 79: cell; 335: complementary cDNA).

FIG. 1 depicts exemplary embodiments of physically combining with each other a peptide or a protein and a nucleic acid molecule encoding the peptide or a protein. Typically a nucleic acid molecule is provided that codes for the peptide or protein. The nucleic acid is introduced into a cell. There it is being expressed, i.e. translated into amino acids and the peptide or protein formed. A simple way of providing physical combination is thus expression (G) of a nucleic acid molecule (39) in a suitable cell (79) to form the encoded peptide or a protein (11) within the cell. A further example is expression of the peptide or a protein (11) encoded by a nucleic acid molecule (39) on the cell surface of the suitable cell (79) (F), whereby the formation of a complex with a potential binding partner can occur outside the respective cell. If a viral vector (32) is used (for instance a bacterial phage or a phagemid), in which the nucleic acid molecule is included, it can easily be isolated. Where a protein of a viral envelope is fused to the peptide or a protein of interest (11), for instance via a linking peptide (5) a physical link is formed (A). In covalent DNA display (B) a covalent bond is formed between encoded peptide or protein (11) and encoding nucleic acid molecule (33), for example using the DNA-binding protein P2A (35). With the DNA-binding protein and the peptide or a protein of interest (11) a fusion protein is formed, again for example via a linking peptide (5). By means of a puromycin molecule (36), a covalent bond between the encoding nucleic acid molecule (34) and the encoded peptide/protein (11), for instance via a linking peptide (5), can be formed in mRNA display (C). In addition, the encoding nucleic acid molecule (334) may be hybridized to an at least essentially complementary cDNA (333) in cDNA display (D). The cDNA carries the puromycin molecule (36), the encoded peptide/protein (11), and optionally a linking peptide (5). By stabilizing the complex between ribosome (37), mRNA (38) and the encoded peptide/protein (11), possibly including a linking peptide (5), e.g. by means of chloramphenicaol, a physical link is formed in ribosome display (E).

Figure 2A:
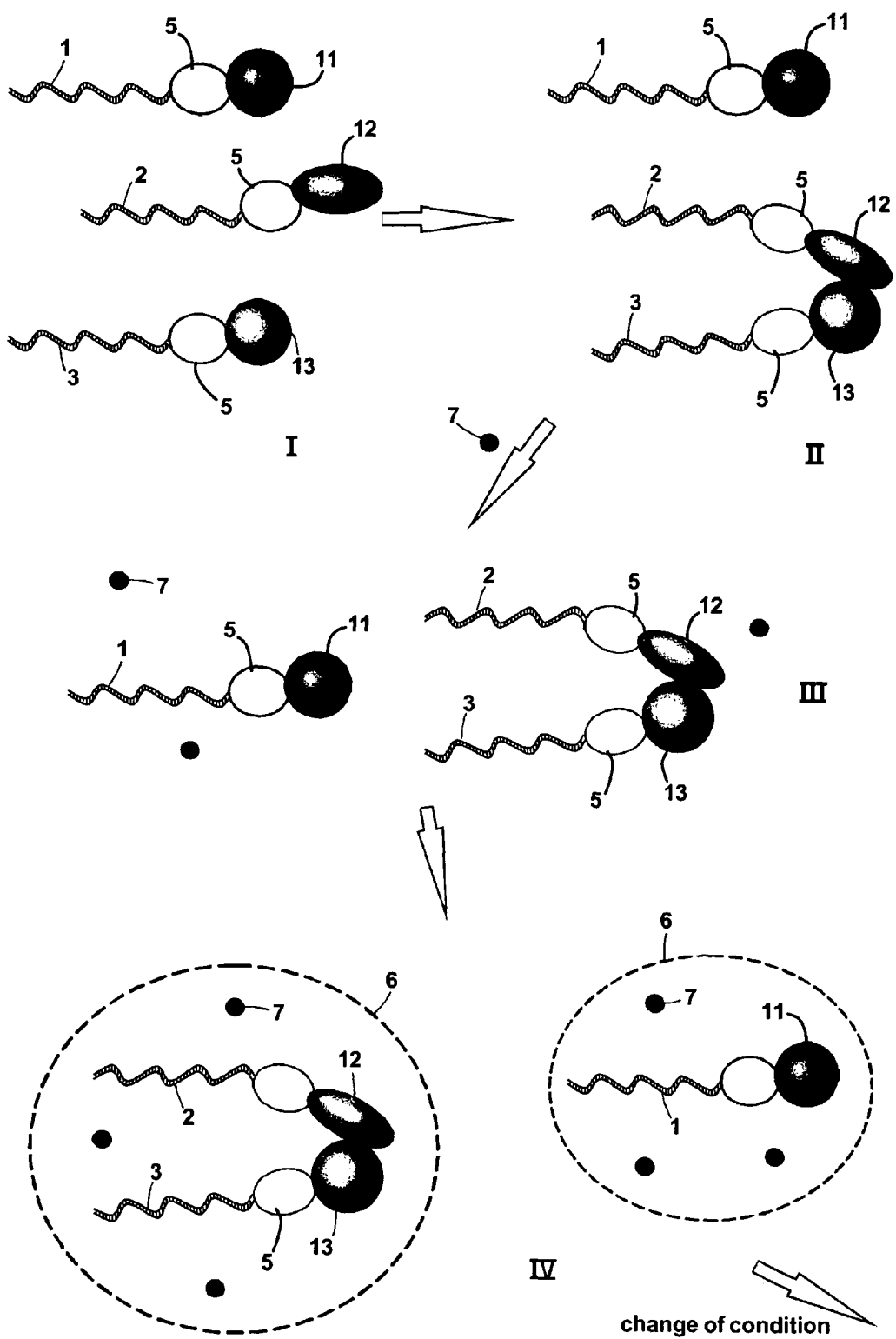
FIG. 2A depicts a schematic of an embodiment of a method according to the present invention, in which a pair of a first (12) and a second (13) binding partner within a plurality of peptides and/or proteins (11, 12, 13) is identified, which are physically linked to a member encoding nucleic acid molecule (1, 2, 3) via a linking moiety (5). In a compartment (6) a factor (7) links the nucleic acid molecules (2, 3) to a joined nucleic acid molecule (4), which can then be retrieved and analyzed via a capture probe (9).
Figure 2A:
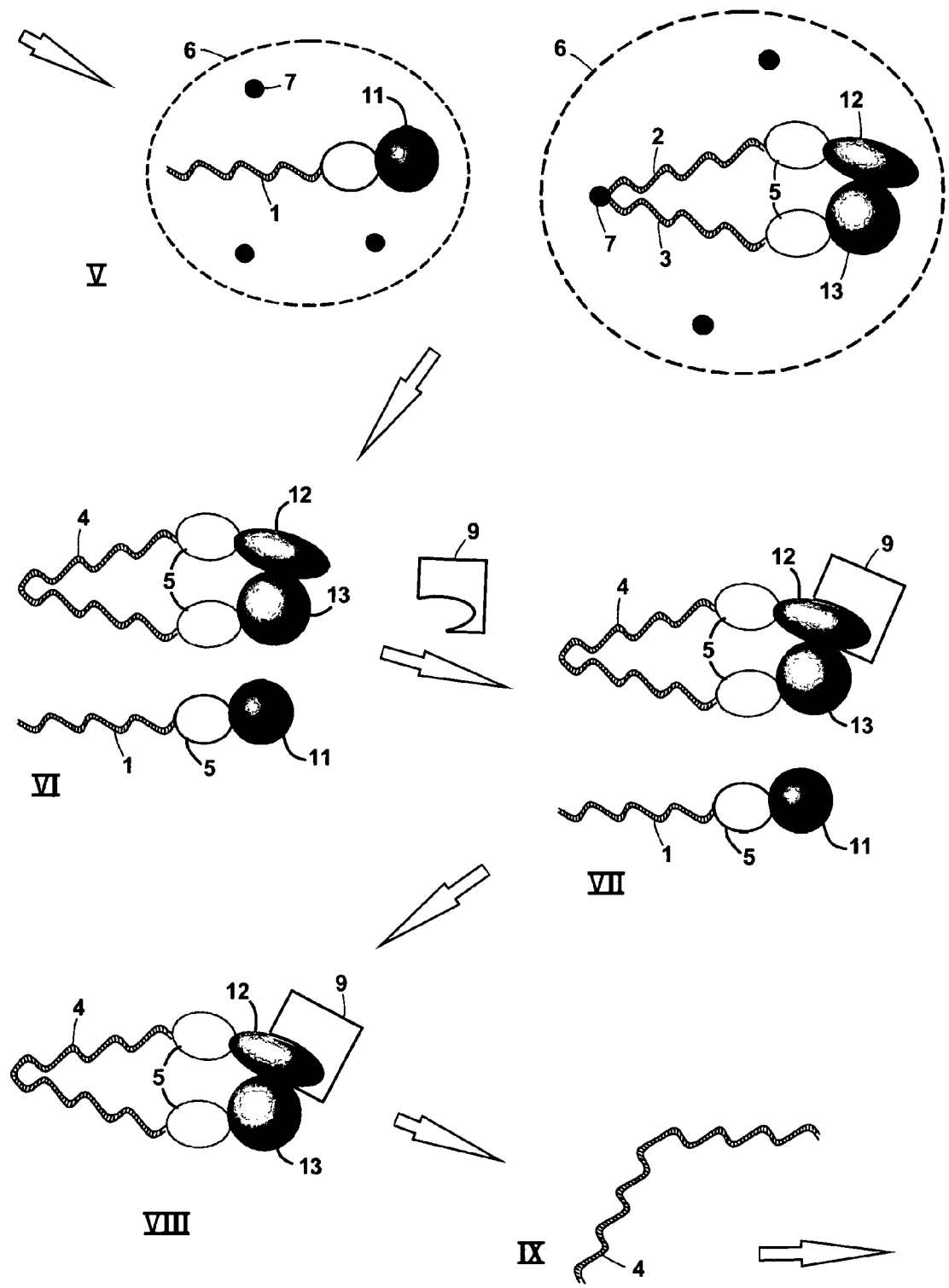
Figure 2A:
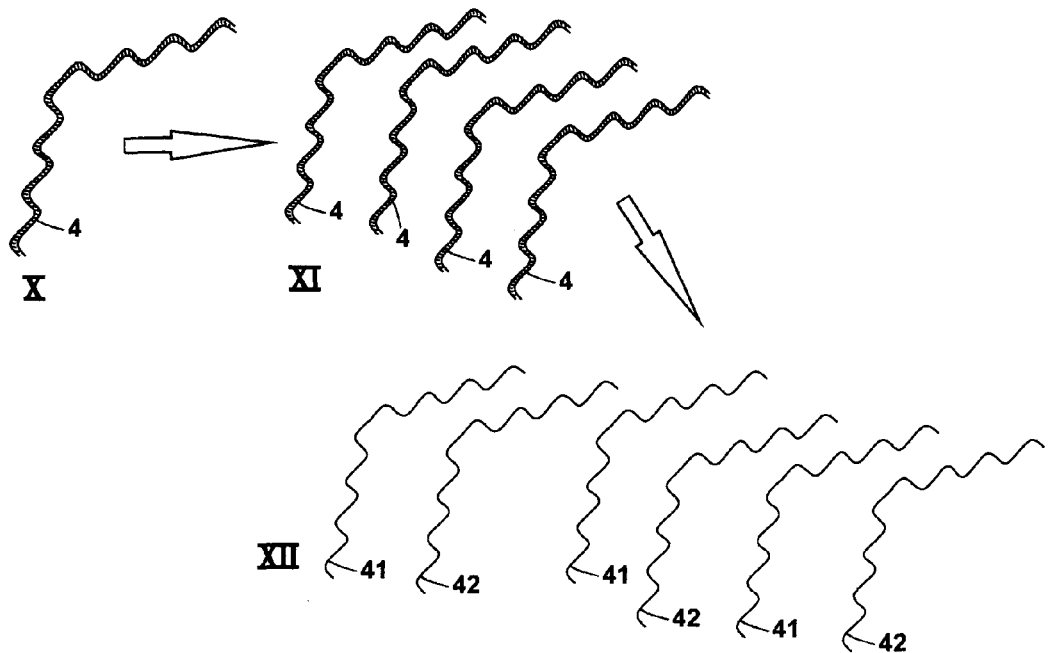

FIG. 2A depicts a schematic of an embodiment of the present invention. In this method a pair of a first (12) and a second binding partner (13) within a plurality of peptides and/or proteins is identified. The plurality of peptides and/or proteins is provided, which includes the first binding partner (12), the identity of which is known (I). The plurality of peptides and/or proteins is further suspected to include a second binding partner (13). The second binding partner (13) will in this case form a complex with the first binding partner (12)(II). Each member of the plurality of peptides and/or proteins (11, 12, 13) is physically linked to a member encoding nucleic acid molecule (1, 2, 3) via a linking moiety (5). These nucleic acid molecules (e.g. (2) and (3)) have a nucleotide sequence that encodes the corresponding peptide (e.g. (12) and (13), respectively), to which they are linked. A factor (7) that is able to link nucleic acid molecules is added to the plurality of peptides and/or proteins under conditions were this factor is inactive, for example at a temperature that is below the temperature range at which the factor is active (III). The plurality of peptides and/or proteins is subdivided into compartments, such that each compartment (6) comprises at most about one complex formed between a pair of binding partners (IV). Upon a change of one or more conditions, such as a change of temperature or the addition of a further factor, the factor (7) is allowed to gain activity. The member encoding nucleic acid molecule (2) of the first binding partner (12) and the member encoding nucleic acid molecule (3) of the second binding partner (13) are thereby allowed to be linked (V). As a result a joined nucleic acid molecule (4) is formed (depicted in the next step). The compartments are allowed to disintegrate (VI). A capture probe (9), capable of associating to the complex of the two binding partners, is added and the capture probe allowed to associate to the respective complex (VII). The capture molecule and thus also the complex between the first and the second binding partner are retrieved (VIII). The physical links between the linking moieties (5) and the joined nucleic acid molecule (4) of the two member encoding nucleic acid molecules (2, 3) is cleaved, so that the joined nucleic acid molecule (4) is released (IX). The joined nucleic acid molecule (4) is amplified (X1) and the two strands of the nucleic acid molecule (41, 42) are separated for sequencing, e.g. according to the Sanger method (XII).

In one embodiment of the method depicted in FIG. 1, the plurality of peptides and/or proteins is provided in the form of a mixture. This mixture is being obtained by contacting a target molecule such as for instance the first binding partner or the second binding partner with a first plurality of peptides and/or proteins, which may be taken to define a source plurality or a root plurality of peptides and/or proteins.

Figure 2B:
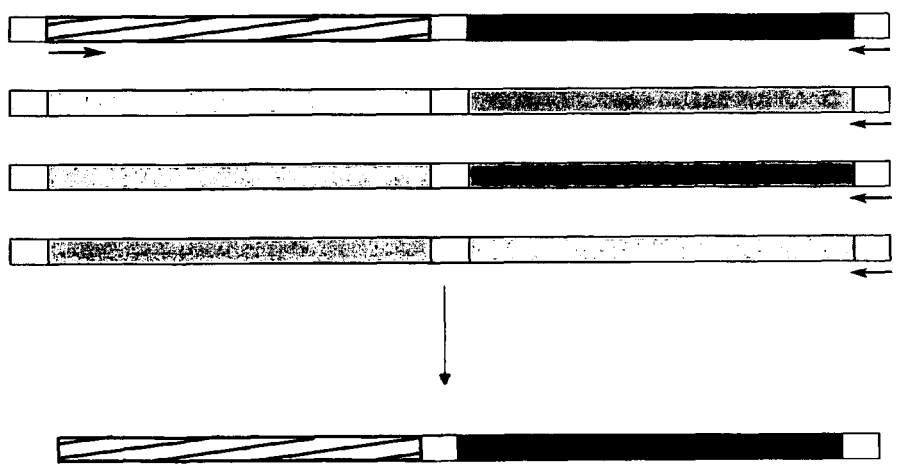
FIG. 2B illustrates the selective amplification of binding partners containing gene of interest.

FIG. 2B illustrates schematically the selective amplification of a joined nucleic acid molecule of two member encoding nucleic acid molecules that encode binding partners, which may be taken to be interacting pairs. A gene specific oligonucleotide is used so that only templates containing the gene specified by the oligonucleotides are amplified. The addition of this gene specific oligonucleotide ensures that only fused nucleic acid molecule encoding binding partners and thereby including the gene of interest, are amplified. The sequence of the amplified products can be determined to identify the binding partner.

Figure 2C:
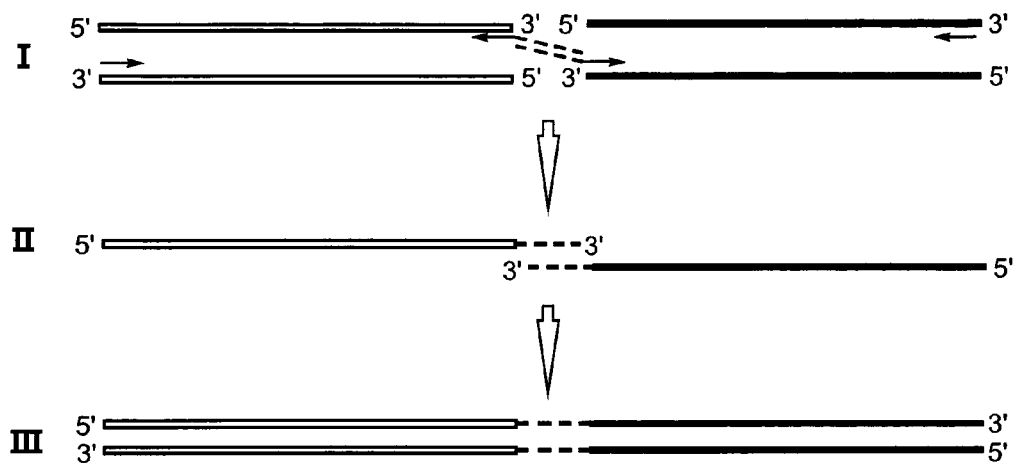
FIG. 2C sketches the splicing-by-overlap-extension (SOE) procedure.

FIG. 2C illustrates schematically the splicing-by-overlap-extension (SOE) procedure. I: A few cycles of asymmetric PCR are carried out with an excess of outer oligonucleotides. II: Annealing and extension of overlapping 3' ends is performed. III: The final SOE product is obtained.

Figure 3:
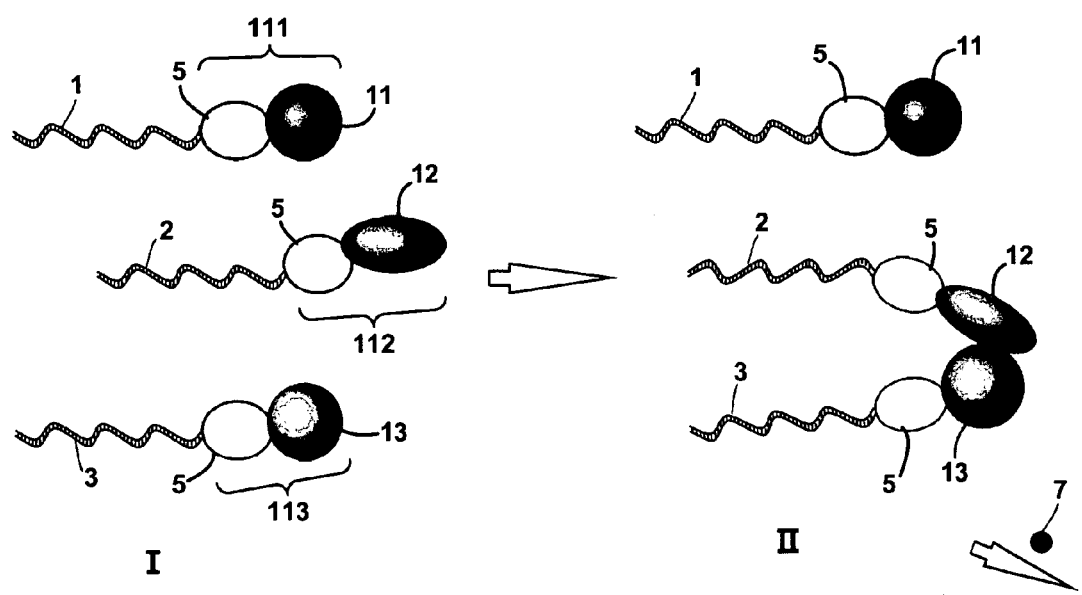
FIG. 3 depicts a schematic of an embodiment of a method according to the present invention of identifying within a plurality of fusion peptides and/or proteins (111, 112, 113) a binding partner (13) of a target peptide or protein (12). The peptides and/or proteins are included in fusion peptides and/or proteins, which also include a linking peptide or protein (5). In a compartment (6) a factor (7) links the nucleic acid molecules (2, 3) to a joined nucleic acid molecule (4), which is then amplified using PCR, purified and analyzed.
Figure 3:
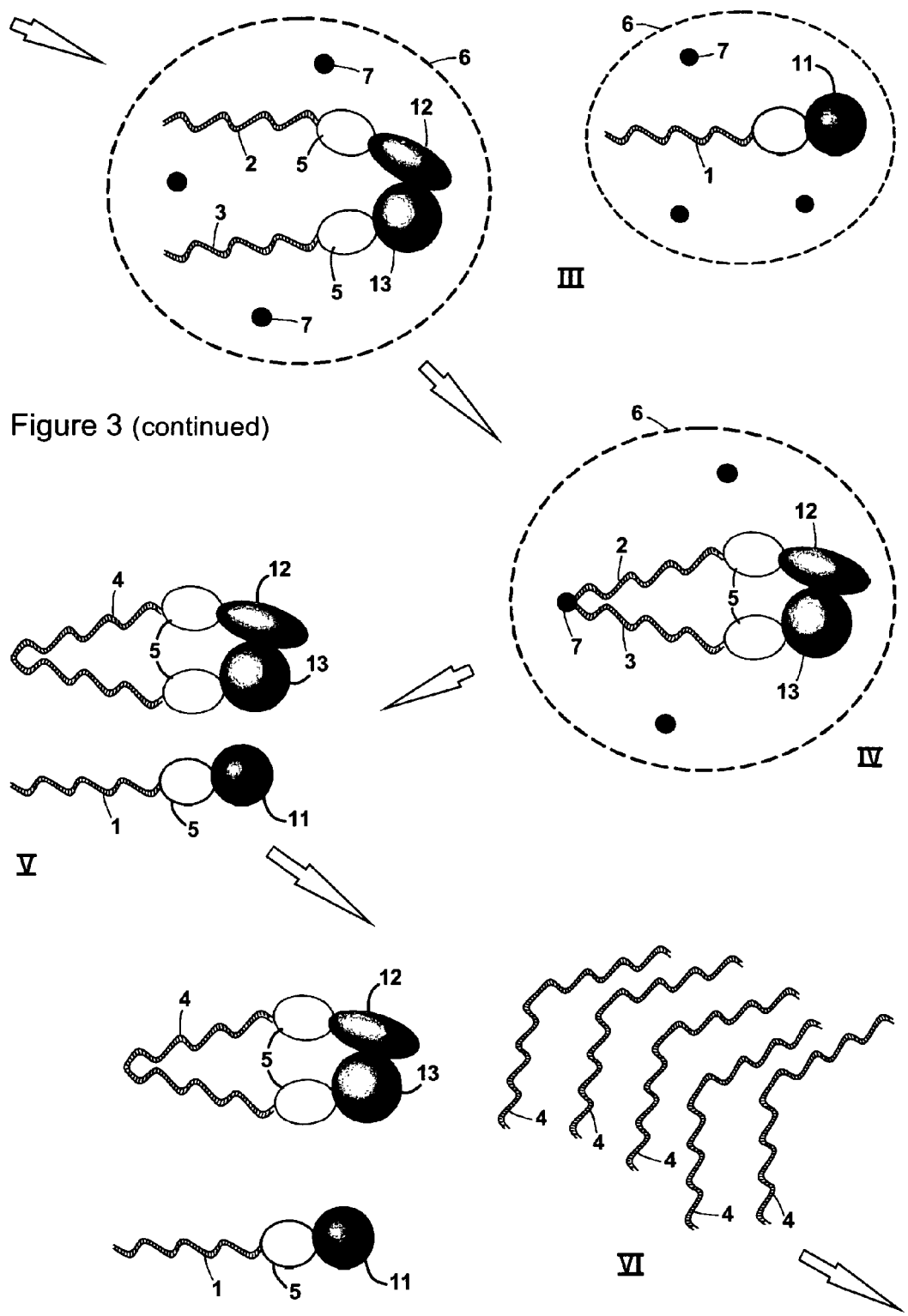

FIG. 3 depicts another schematic of an embodiment of the present invention. In this method a plurality of fusion peptides and/or proteins (111, 112, 113) is provided (I). Each member of the plurality of fusion peptides and/or proteins includes a linking peptide or protein (5) (such as HaeIII methylase) and a further peptide or protein (11, 12, 13). The linking peptide or protein (5) of each member of the plurality of fusion peptides and/or proteins is physically linked to a member encoding nucleic acid molecule (1, 2, 3). Each of the member encoding nucleic acid molecules includes a nucleotide sequence that encodes the fusion peptide or protein (111, 112, 113) linked thereto. One of the further peptides or proteins included in the plurality of fusion peptides and/or proteins is the target peptide or protein (12). Additionally, the other further peptides and/or proteins (11, 13) are suspected to include a binding partner that is capable of forming a complex with the target peptide or protein (12). A complex between the target peptide or protein (12) and the binding partner (13) may be allowed to form (II). Alternatively, this complex may also have formed before carrying out the method of the invention. A factor (7) is added that is capable of ligating the ends of nucleic acid molecules, and the plurality of peptides and/or proteins is subdivided into compartments (6) (III). Each of the formed compartments includes not more than one member or one complex between members of the plurality of peptides and/or proteins. The complex between the target peptide or protein (12) and the binding partner (13), each of which being linked to the corresponding member encoding nucleic acid molecule (2, 3), is thus separated from the remaining further peptides or proteins. The factor (7) links the member encoding nucleic acid molecule of the target peptide or protein (2) and the member encoding nucleic acid molecule of the binding partner (3) (IV). Thus a composite nucleic acid molecule (4) is formed that is physically linked to the target peptide or protein (12) and to the binding partner (13) (depicted in the next step). The compartments (6) are allowed to disintegrate (V). Accordingly a mixture of the plurality of fusion peptides and/or proteins is formed again. A PCR is carried out a using a pair of a first and a second primer. The first primer is complementary to a part of the sequence of the member encoding nucleic acid molecule encoding the target peptide or protein (not shown). The second primer is a universal primer (not shown). Accordingly, the composite nucleic acid molecule (4) is amplified (VI). The composite nucleic acid molecule (4) is purified, such that the plurality of fusion peptides and/or proteins with the linked member encoding nucleic acid molecules is at least essentially removed (VII). The sequence of the composite nucleic acid molecule is determined by means of an automated sequencer (50) (VIII, IX).

Figure 4:
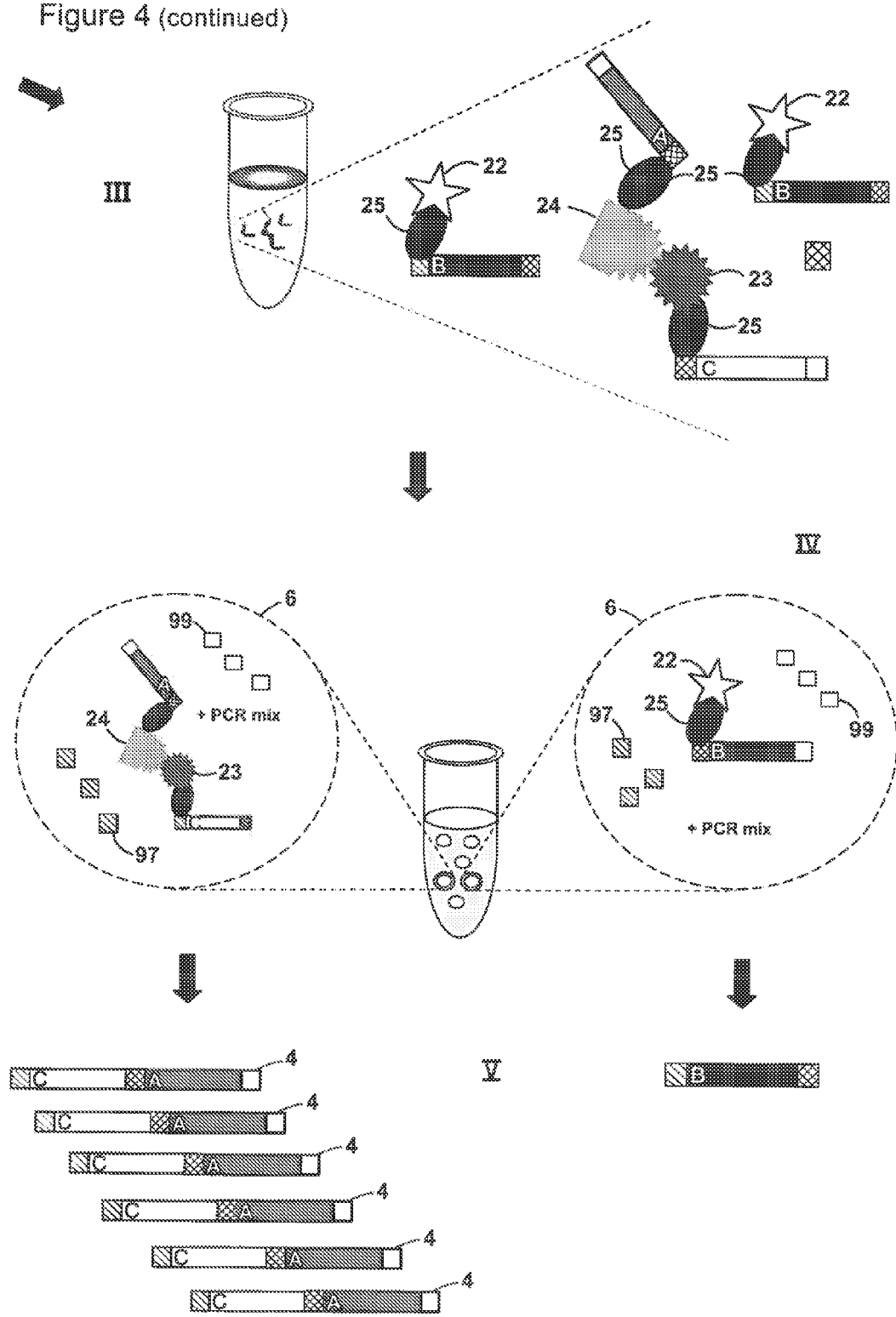
FIG. 4 depicts a further schematic of an embodiment in which a pair of two binding partners (23, 24) within a plurality of peptides and/or proteins encoded by a variably tagged cDNA library is identified. Following in-vitro translation each peptide and/or protein is linked to a cDNA molecule encoding it via a linker molecule (25). In a compartment the binding partners are linked and after disintegration of the compartment amplified.
Figure 4:
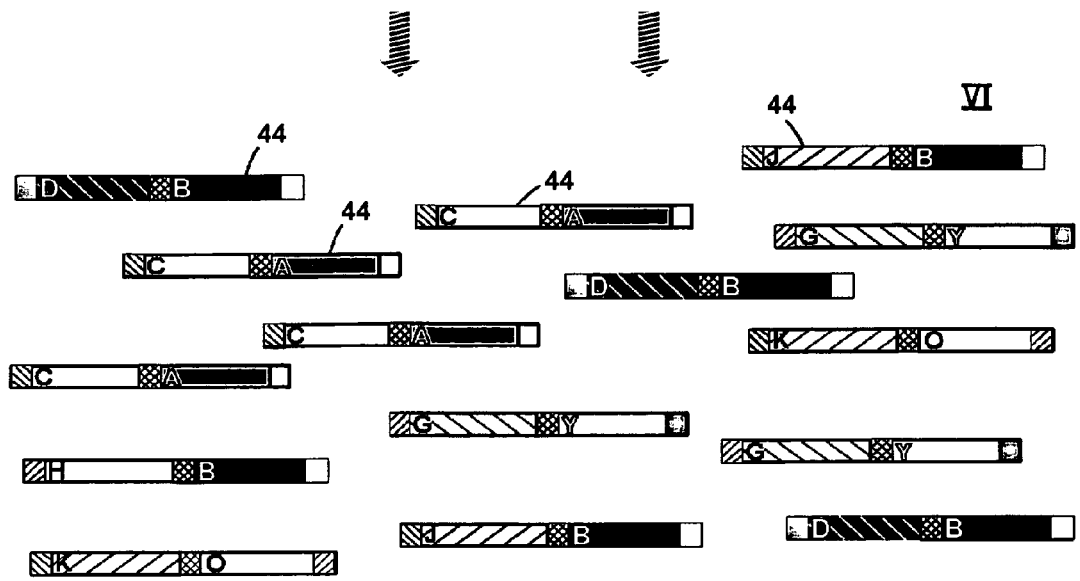

FIG. 4 depicts a further schematic of an embodiment of the present invention. A variably tagged cDNA library is provided (I). The tagged nucleotide sequences are denoted with reference numerals 97, 98 and 99. The proteins and/or peptides encoded by the cDNA molecules are formed by in-vitro translation (II). Thereby each formed protein/peptide is allowed to bind back only to the cDNA with the encoding gene. Each protein/peptide formed is linked to the corresponding cDNA molecule via a linker molecule (25). Within the plurality of peptides and/or proteins (22, 23, 24) the formation of a complex between a first (23) and a second (24) binding partner is allowed (III). The plurality of peptides and/or proteins is subdivided into compartments (6) (IV). Each of the formed compartments includes not more than one member of the plurality of peptides and/or proteins (22) or one complex between members (23, 24) of the plurality of peptides and/or proteins. The member encoding nucleic acid molecules of the first and the second binding partner ("A" and "C") are linked and the compartments allowed to disintegrate (V). Using this method a nucleic acid library of composite nucleic acid molecules (44) can be formed (VI), in particular where a large tagged cDNA library is provided—for instance encoding a plurality of proteins/peptides that is larger than 10 000, 100 000, than $10^6$, $10^7$, $10^8$, $10^9$, or $10^{10}$, including larger than $10^{11}$, than $10^{12}$ or than $10^{13}$ (exemplary number also indicated in FIG. 41). In this regard the present invention also provides a kit that includes a corresponding plurality of composite nucleic acid molecules (44). The library composite nucleic acid molecules (44) can then be used to probe for interactants of a given target protein by PCR using a target-specific oligonucleotide primer and a universal primer (see FIG. 5).

Figure 5:
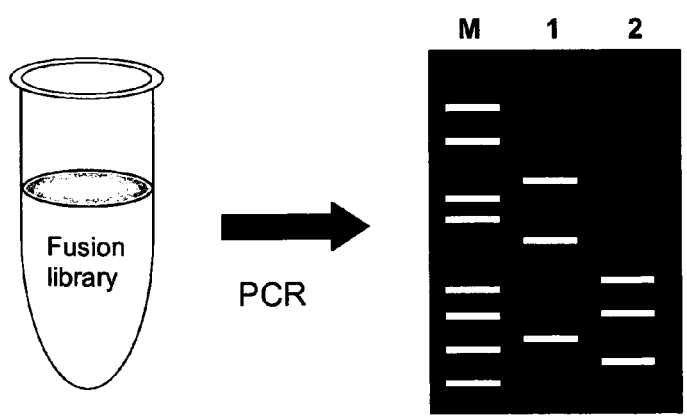
FIG. 5 depicts gel electrophoresis of a library of linked nucleic acid molecules formed using a method of the current invention. The composite nucleic acid molecules can be probed to identify interactants of a certain target peptide or protein molecule by PCR using a target-specific oligonucleotide and a universal primer. A representative gel is shown wherein different composite nucleic acid molecules (encoding interactant proteins) to target protein 1 (lane 1) and target protein 2 (lane 2) are amplified by PCR.

FIG. 5 depicts an example of an additional step to separate composite nucleic acid molecules that may have been formed in a method according to the invention. A library of linked nucleic acids formed using a method according to the current invention can be probed to identify interactants of a target molecule/peptide by PCR using a target-specific oligonucleotide and a universal primer. For analysis of the depicted gel different composite nucleic acid molecules were amplified by PCR. The nucleic acid molecules included sequences that encoded interactant proteins to target protein 1 (lane 1) and target protein 2 (lane 2). Separation of composite nucleic acid molecules may be desired where a plurality of peptides and/or proteins may for instance include a first binding partner as well as a second binding partner, a third binding partner, and a fourth binding partner. Each of the second, the third and the fourth binding partner may be capable of forming a complex with the known first binding partner, for example alternatively. Further, in some embodiments at least two target molecules may be used in a method according to the invention. Each target molecule may form a complex with one or more binding partners. In order to separate these complexes gel electrophoresis may be used (bands are symbolized for a plurality of known marker nucleic acids (M) and two lanes (1) and (2)).

FIG. 6A illustrates the use of the yeast two hybrid system, which may be included into or combined with the method of the invention. A first peptide or protein, termed the bait (indicated with "X"), is linked to a DNA-binding domain (DBD) of a transcription factor. The transcription factor is capable of binding to an upstream activating sequence (UAS), such as a promoter, of a reporter gene. A second peptide or protein, termed the prey (indicated with "Y"), is linked to an activating domain (AD) of the same transcription factor. If the bait and the prey form a complex, physical contact between the DNA-binding domain and the activating domain is established. As a result, the upstream activating sequence is activated and typically the reporter gene expressed. In a standard protocol in the art, yeast is seeded onto a plate in the absence of a selected (lower part of the figure). The yeast used lacks the ability of forming a reporter enzyme, for example due to a lack of a required transcription factor. The activity of the reporter enzyme can be visualised. A first plasmid is used, which includes a sequence encoding a fusion protein/peptide of the DNA-binding domain of the missing factor and a first protein, and a second plasmid, which includes a sequence encoding a fusion protein/peptide of the activating domain of the missing factor and a second protein. Upon growing the yeast forms colonies. If in a yeast cell, from which a colony has formed, interaction between the first and the second protein has occurred, the cells of the colony (81) can be identified by a colour generated by the reporter enzyme. Colonies without such interaction (80) cannot produce a corresponding colour.

Figure 6B:
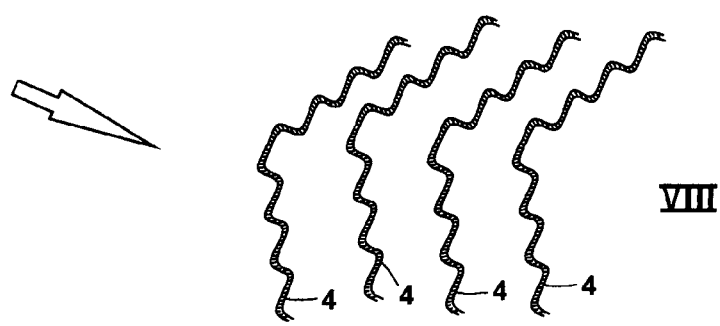
FIG. 6B depicts a schematic of a method of identifying a binding partner of a target peptide or protein (12). A plurality of member encoding nucleic acid molecules (3, 15, 17) is screened by introduction into in a host cell (79) using a nucleic acid molecule (2) that has a sequence encoding a target peptide or protein (12). The member encoding nucleic acid molecules encode a fusion protein of the respective peptide/protein (13, 14) and a first complementing moiety (76). Correspondingly, the target peptide or protein (12) is expressed as a fusion peptide/protein with a second complementing moiety (75). Cells (81) can be identified in which the complementing moieties form a reporter peptide. Such cells are collected and distributed into separate compartments. The nucleic acids encoding the binding partners are linked and retrieved, for example in a manner resembling the example depicted in FIG. 3.

FIG. 6B depicts a schematic of a method of identifying a binding partner of a target peptide or protein according to a method of the present invention. A plurality of member encoding nucleic acid molecules (3, 15, 17) is provided (I). Each of the member encoding nucleic acid molecules includes a sequence encoding a peptide or protein that is to be analysed for its ability of forming a complex with the target peptide or protein. The plurality of member encoding nucleic acid molecules is screened for molecules that are suspected to encode a binding partner of the target peptide. Each member encoding nucleic acid molecule is introduced into a different host cell (79) (II). A further nucleic acid molecule (2) is introduced into each host cell (79) (III), which includes a sequence that encodes the target peptide or protein. A plurality of different nucleic acid molecules, encoding a plurality of different target peptides (or proteins) may be used. In such embodiments only one target peptide encoding nucleic acid molecule is introduced into each cell. Each of the member encoding nucleic acid molecules further include a sequence encoding a first complementing moiety (cf the description for details). The nucleic acid molecule that includes a sequence for the target peptide or protein further includes a sequence that encodes a second complementing moiety. The first and the second complementing moiety together form a functionally active factor that provides a signal, for example by modulating the expression of a reporter gene of the host cell (79). The cells express the peptides. In a cell where the target peptide/protein and the corresponding binding partner thereof are expressed together, a complex of the two interacting binding partners forms. In such a cell the first and the second complementing moiety together form a functionally active factor. Host cells in which interaction between the complementing moieties has occurred (81) can be distinguished from host cells where no such interaction has occurred (80), e.g. based on the action of the reporter gene (IV). Host cells (81) thus identified are sorted for further processing. A factor (7) may be added that is capable of ligating the ends of nucleic acid molecules, and the plurality of cells is subdivided into compartments (6) (V). Each of the formed compartments includes not more than one cell (81). Cells are allowed to disintegrate and the two nucleic acid molecules inside the compartment that encode the two binding partners are allowed to be linked (VI), for example by the factor 7. This may be a primer for a suitable nucleic acid amplification that allows linked nucleic acids to be formed. As a result a composite nucleic acid molecule (4) is formed (depicted in the next step). The compartments (6) are allowed to disintegrate (VII). The obtained copy/copies of the composite nucleic acid molecule(s) may be further amplified (VIII).

Figure 7:
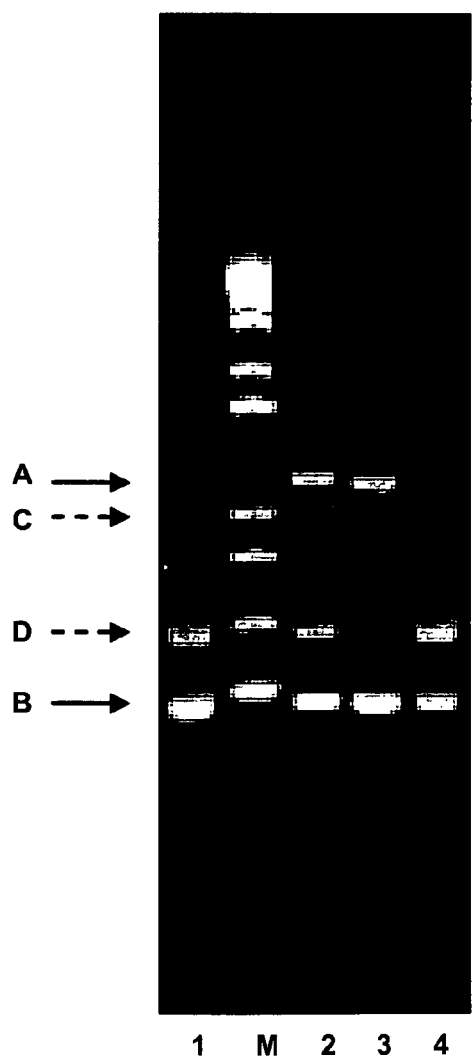
FIG. 7 depicts a cross-over test of the cognate linkage of plasmid inserts present in two bacterial cell lines. Cells were emulsified and processed as described below. Lane 1: Non-emulsified aqueous control. Lane 2: Top fraction from emulsion reaction. Lane 3: Middle fraction from emulsion reaction. Lane 4: Bottom fraction from emulsion reaction. M: Molecular weight marker.

FIG. 7 illustrates carrying out a method according to the invention on a bacterial system, in chromatographic analysis. Cognate linkage of plasmid inserts present in two bacterial cell lines is depicted. Cells were emulsified and processed as described below. $10^6$ cells each of BC165 and BC166 were emulsified and subjected to SOE-PCR. Cognate linkage of 2 plasmid inserts present in BC165 results in a 1150 bp band (A). Cognate linkage of two plasmid inserts present in BC166 results in a 480 bp band (C). Incorrect (non-cognate) linkage of plasmid inserts from BC165 and BC166 results in bands corresponding to 1000 bp (D) and 640 bp (B). Lane 1 refers to non-emulsified aqueous control, M refers to the DNA ladder.

Lane 2 indicates the top fraction of emulsion SOE-PCR, lane 3 denotes the middle fraction while lane 4 indicates the bottom fraction which also contains lysed emulsion droplets.

As can be seen, emulsification (notably the top and middle fractions, lanes 2 and 3) results in the predominant isolation of the correctly linked plasmid inserts (A and B), indicating segregation of single bacterial cells into individual emulsion compartments. In the absence of emulsification all four possible linkage combinations are seen, with no clear enrichment of the desired products A and B (Lane 1).

FIG. 8A illustrates schematically cells (79) containing two different plasmids (white and hatched donuts), each of which carries a different insert (black, striped, stippled, diamond). The cells are emulsified in reaction mixture. Emulsification ensures segregation of cells into individual compartments and correct (clonal) linkage of the plasmid inserts (products A and B). As FIG. 8B illustrates, without the formation of compartments the cells (and plasmids) are allowed to randomly interact during linkage procedure. Thereby both correct linkage products (A and B) and incorrect linkage products (C and D) are formed.

FIG. 10 illustrates how the emulsion formation can be optimized. A: Lane T indicates the top fraction of emulsion SOE-PCR, lane B denotes the bottom fraction while lane B' indicates lysed emulsion. Lane M refers to the DNA ladder. Correctly spliced 1350 bp and 1200 bp bands arising from YC16_14 and Yc16_6 are numbered 2 and 3 respectively. Incorrect splicing leads to 990 bp and 1560 bp bands numbered 4 and 1 respectively. The faint lower bands are unspliced individual amplicons from YC16_14 and YC16_6. Note that incorrect band 4 becomes very prominent in lane B' when emulsion is not intact; correspondingly band 3 becomes fainter. B: Templates from lanes T and B were diluted 100 fold, and 1 µl of this was used as a template for secondary PCR in emulsion using nested oligos A and D. The results show that it is possible to consistently re-amplify the library resulting from the primary emulsion SOE-PCR without affecting the relative composition.

FIG. 11 depicts a further example of carrying out a method according to the invention by forming an emulsion. Lane 1 indicates the top emulsion fraction; Lane 2 the Middle emulsion fraction; Lane 3 the Bottom emulsion fraction; Lane 4 the Lysed emulsion fraction; Lane 5 the Aqueous control, and Lane M refers to the DNA ladder. Cognate linkage of 2 plasmid inserts present in YC9 results in 1100 bp band (A). Cognate linkage of 2 plasmid inserts present in YC3 results in 625 bp band (B). Incorrect (non-cognate) linkage of plasmid inserts from YC9 and YC3 results in bands corresponding to 1150 bp (C) and 575 bp (D). As can be taken from the figure, the desired products A and B are strongly enriched in emulsion relative to mispaired bands C and D, implying that most cells remain isolated during the emulsion PCR process.

FIG. 12 shows the retrieval of a desired SOE sequence from a mixture using emulsion SOE, also illustrating model selection and illustrates determining the threshold of detection. Lane T indicates the top fraction of emulsion SOE-PCR, lane B denotes the bottom fraction while lane B' indicates lysed emulsion. Lane Aq refers to non-emulsified aqueous control; M refers to the DNA ladder. The correct sized band is highlighted. Note that a product is also seen in the lysed emulsion lane (lane 3). This is likely due to the fact that lysis may happen after splicing of pGBK and pACT2 inserts, as well as carry-over of genuine spliced YC8 DNA from the bottom fraction. (A) 1000, 100, 10 and 0 YC8 cells, as indicated, were mixed with 250,000 YC16 library cells and subjected to emulsion SOE-PCR. After completion of SOE-PCR, the emulsion was lysed and 1 µl of the extract was used as a template for secondary PCR using nested oligos A and p53rev3 which amplify the correctly spliced YC8 SOE product. The results were run on the above agarose gel. (B) Further refinement of the threshold of detection was undertaken by mixing 500, 300, 200, 100 and 0 cells respectively, as shown, with 250,000 YC16 library cells. The same procedure as described in (A) was carried out. The detection limit of the current embodiment is in the order of 500 cells in 250,000. This is suitable for application of this technique to yeast two hybrid library vs. library experiments.

In the examples illustrated herein, in vitro compartmentalization of cells in water-in-oil emulsions is employed. Within each emulsion droplet, an interacting gene pair from a single cell (or cell-phage pair in the case of yeast-phage display (Bowley et al., 2009, supra) are linked using splicing by overlap extension PCR (SOE-PCR). Once interacting pairs are linked as a single segment of DNA, they can be pooled, amplified, disseminated to the wider community and interrogated for interactions involving genes of interest using gene specific primers.

A cross-over test of the cognate linkage of plasmid inserts present in two bacterial cell lines is illustrated in the following. Cells were emulsified and processed as follows:

Materials

Oil Phase:

A non-ionic surfactant (SPAN 80—Sigma Aldrich), a non-ionic surfactant emulsifier (TWEEN 80—Sigma Aldrich) and hydrophilic polyethylene oxide (TRITON X-100—BDH) were added to light mineral oil (Sigma Aldrich) to final concentrations of 4.5%, 0.4% and 0.05% respectively. Usually the components were mixed using a magnetic stirrer and stored at 4° C. The oil phase was used within 2 weeks of preparation.

In subsequent experiments a modified mineral oil and surfactant mix (called the 9% CSR mix) was prepared by doubling the surfactant concentrations used by Ghadessy et al. (*Proc Natl Acad Sci U.S.A.* (2001) 98, 8, 4552-4557) thereby containing 9% v/v SPAN 80 (Sigma), 0.8% v/v TWEEN 80 (Sigma), and 0.1% TRITON X-100 (BDH) in light mineral oil (Sigma). The 9% CSR mix was stored at 4° C. and was thoroughly mixed just prior to usage.

Aqueous Phase:

PCR reagents were from Bioline.

*E. coli* Strains:

XL-1 Blue (Stratagene) cells were transformed with both the pet22b and DsRed vectors. This strain is named BC 166. BC 165 is an XL-1 Blue strain carrying the same vectors except that the pet22b vector contains a 550 bp Leukaemia inhibitory factor (Lif) insert, while the DsRed vector has a 150 bp Δ-fos insert. Log-phase BC165 and BC166 cells were washed 3 times with 1 ml PBS prior to use.

Primers:

The following primers were used to carry out splicing by overlap extension (SOE) and secondary PCR:

```
PetF2:
                                        (SEQ ID NO: 1)
5'-CAT CGG TGA TGT CGG CGA T-3',

PetF3:
                                        (SEQ ID NO: 2)
5'-ATA GGC GCC AGC AAC CGC ACC TG-3',

Pet22-RSOE:
```

-continued

```
                                          (SEQ ID NO: 3)
5'-GGC GCG CCA TGG GAA TAG CTA GGT TAG

CAG CCG GAT CTC AGT G-3',

DsRed-FSOE:
                                          (SEQ ID NO: 4)
5'-CTA GCT ATT CCC ATG GCG CGC CTA GCG

CTA CCG GAC TCA GAT CTC-3', pDS-R:
                                          (SEQ ID NO: 5)
5'-CAC CTT GAA GCG CAT GAA CTC C-3',

DSR-nest:
                                          (SEQ ID NO: 6)
5'-CTC GGA GGC CAT GGT G-3'
```

Methods

Emulsion Preparation:

250 μl of 1×SOE PCR aqueous phase mix comprised $MgCl_2$ (1.5 mM), dNTPs (200 μM), PetF2 (500 nM), Pet22-RSOE (20 nM), DsRed-FSOE (20 nM.) p-DSR (500 nM.), Taq Polymerase (10 units), BC165 cells (1×10$^7$), BC166 cells (1×10$^7$), BSA (100 μg/ml).

200 μl of the above aqueous phase was added to 400 μl of the oil phase in a NUNC Cryotube vial. The vial was securely fastened using adhesive tape to an IKA MS2 minishaker. The tube was then agitated at 2350 rpm for 6 min 30 sec. Thereafter, 35 μl of the emulsion was aliquoted into multiple 200 μl PCR strips and subjected to PCR. The remaining 50 μl, aqueous phase was used as non-emulsified PCR control.

When the 9% CSR mix was used, during emulsification, 400 μl of the 9% CSR mix was placed in a CryoTube (Nunc) along with a small magnetic 8 mm×3 mm pivoted stirbar on a magnetic stirrer (Corning PC-620D) at ~550 rpm. 200 μl ice-cold aqueous PCR mix was then added to the above at the rate of 1 drop per 5 seconds, totaling about 70 seconds. The mixture was allowed to stir for a further 120 seconds, and then removed from the magnetic stirrer. 35 μl emulsion was aliquoted into 15 tubes from two 8-tube strips, with the last tube containing un-emulsified PCR mix as a control. The strips were then placed on a PCR block for thermal cycling.

Emulsion Fractionation:

In general, a small amount of aqueous phase is found at the bottom of the emulsion after completion of SOE-PCR. This represents merged droplets and contains a high concentration of incorrectly fused genes (miscognate bands) due to the mixing of multiple templates. This lysed emulsion fraction is removed by careful pipetting from each tube and pooled. Next, 10 μl of emulsion is withdrawn from the bottom from each tube of the 8-tube strip and pooled. This fraction is referred to as the bottom fraction and represents the relatively larger droplets that tend to sink to the bottom. The remainder of the emulsion, called the top fraction is then pooled and all fractions are extracted as described below. This procedure is repeated for all the tubes containing a given emulsion.

Emulsion Extraction:

After the PCR protocol was complete, the tubes were allowed to remain upright at room temperature for a further 1-2 hours to allow large aqueous droplets to settle to the bottom of the tube. Thereafter, 10 μl was removed from the bottom of each tube. This part of the emulsion was pooled and labeled the bottom fraction. The remaining emulsion was pooled in another tube and called the top fraction. Both tubes were spun at 800×g for 2 minutes on a benchtop centrifuge (Eppendorf). This causes the bigger aqueous droplets, which are likely a product of the merger of multiple droplets, to settle at the bottom of the tube. This aqueous fraction was carefully removed from both top and bottom fractions and pooled in a separate tube, labeled the lysed emulsion fraction. 900 μl diethyl ether was then added to the remaining emulsion from the top and bottom tubes, the contents vortexed and spun down at 16100×g for 2 minutes on a benchtop centrifuge. This causes emulsion lysis and separation of the aqueous and hydrophobic phases, with the aqueous phase at the bottom of the tube. The hydrophobic phase was carefully removed with a pipette. Another 900 μl diethyl ether was added to the aqueous phase and the above procedure was repeated to yield the product of the emulsion PCR.

PCR:

Unless otherwise indicated, the following thermal cycling protocol was used for emulsions:

94° C. for 5 minutes, 94° C. for 10 seconds, 60° C. for 45 seconds, 72° C. for 90 seconds, total 30 cycles.

Secondary PCR:

Unless otherwise indicated, the secondary PCR reaction comprised: 1 μl extracted emulsion PCR template, $MgCl_2$ (1.5 mM), dNTPs (200 uM), PetF$_3$ (200 nM), DSR-nest (200 nM), Taq polymerase (limit) in a final volume of 30 μL.

The PCR protocol was as follows: 94° C. for 5 minutes, 94° C. for 10 seconds, 55° C. for 20 seconds, 72° C. for 90 seconds, total of 25 cycles.

Splicing by Overlap Extension (SOE)-PCR Procedure and Oligonucleotides:

Typical emulsion SOE-PCR reactions have a total volume of 250 μl and contain: 1× Biotaq $NH_4$ buffer (Bioline), 200 nM Gal4ADF forward oligonucleotide (5' AATACCACTAC AATGGATGATG 3', SEQ ID NO: 7), 200 nM reverse oligonucleotide D (5' CCCGGAATTAGCTTGGCTGCAAC 3', SEQ ID NO: 8), and 20 nM each of SOE oligonucleotides H2HB2 (5' CCGCCGCTACCACCACCGCCAAGAT GGTGCACGATGCACAGTTG 3', SEQ ID NO: 9) and H2HC2 (5'GGCGGTGGTGGTAGCGGCGG AGTGCGACATCATCATCGGAAGAGAGTAG 3', SEQ ID NO: 10). Lyticase from *Arthrobacter* Luteus (Sigma) was added at a final concentration of ~350 units/ml. 10 units of 1 mmolase DNA polymerase (Bioline) was used. Yeast cells were suspended in 1 ml PBS, washed 5× and then counted using a hemocytometer (Brightline). Typically, 250,000 cells were then suspended in 5 μl PBS and added to the ice-cold PCR mix, just before the emulsification procedure. Thermal cycling was carried out on a PTC-200 (MJ Research) instrument. The protocol for emulsion SOE-PCR was as follows: 37° C. for 1 hour (lyticase digestion), 95° C. for 10 minutes (activation of 1 mmolase), followed by 35 cycles of 95° C. for 10 seconds, 57° C. for 30 seconds and 72° C. for 2 minutes. A final 72° C., 5 minute extension step was included.

Rescue PCR Oligonucleotides and Procedure:

For secondary PCR, the typical volume of the final reaction is 30 μl, containing 1×BioTaq $NH_4$ buffer, 200 nM oligonucleotide A (5' CTATTCGATGATGAAGATACCCCAC-CAA ACC 3', SEQ ID NO: 11) and 200 nM of oligonucleotide p53rev4 (5' GGAACTGTTACA CATGTAGTTGTAG 3', SEQ ID NO: 12). Generally 1 μl of primary extracted PCR product was used as the template. One unit of BioTaq DNA polymerase was used. The thermal cycling procedure, unless otherwise mentioned is as follows: 95° C. for 5 minutes, followed by 35 cycles of 95° C. for 10 seconds, 57° C. for 10 seconds and 72° C. for 2 minutes.

Oligonucleotides and Protocol Used for Bacterial Emulsion SOE-PCR:

petF2 (SEQ ID NO: 1) and DsRev (5' CACCTTGAAGCG-CATGAACTCC 3', SEQ ID NO: 5) were used as outer primers. Internal SOE primers are petRSOE (SEQ ID NO: 3) and DsFSOE (SEQ ID NO: 4). The secondary rescue PCR oligonucleotides were petF3 (SEQ ID NO: 2) and DsR-rev (5' CTCGGAGGAGGCCATGGTG 3', SEQ ID NO: 13). The thermal cycling protocol is an initial heating step of 95° C. for 5 min, followed by 30 cycles of 95° C. for 10 sec, 60° C. for 45 sec and 72° C. for 90 sec.

Results

Basic Scheme of Operation

Each cell known to contain two interacting genes is a repository of protein-protein interaction data. However, this information is not easily accessible. To rectify this problem, it was opted in the present invention to link the two interacting genes into one segment of DNA by Splicing by Overlap Extension-PCR (SOE-PCR) (Horton, R M, et al., Methods Enzymol (1993) 217, 270-9) as shown in FIG. 2C, which can then be isolated, amplified and interrogated using common DNA manipulation techniques. To accomplish this simultaneously with a large number of cells without linking non-cognate genes from different cells, a mixture of cells was emulsified to isolate them from each other (Tawfik & Griffiths, 1998, supra; Griffiths, A D, & Tawfik, D S, Trends Biotechnol (2006) 24, 9, 395-402). In addition, lyticase was added to digest the yeast cell wall, rendering the interacting genes accessible to PCR reagents.

The outer primers for the SOE procedure used are GAL4ADF, which is complementary to the GAL4 Activation Domain in plasmid pACT2, and D, which is complementary to the pGBKT7 vector after the Multi-Cloning Site (MCS). Internal primers are H2HB2 and H2HC2, which have complementary 5' halves, and 3' ends complementary to the pACT2 and pGBKT7 vectors respectively. Hotstart DNA polymerase 1 mmolase (Bioline) is used to prevent primer dimerization from occurring during the lyticase digestion step. After the SOE-PCR mix is constituted, an appropriate number of cells is added, followed immediately by emulsification (see materials and methods). The number of cells is chosen such that each aqueous droplet in emulsion is very unlikely to contain more than one cell. The emulsion is then placed on a PCR block. The first step is an one hour incubation at 37° C., which allows the lyticase to digest the cell wall. The next step is a 10 minutes incubation at 95° C., which both activates the Immolase enzyme, and releases the plasmids from the lyticase treated cells. Subsequent steps are typical of SOE-PCR (see materials and methods).

After the SOE-PCR in emulsion is complete, the emulsion is lysed by ether treatment and the linked genes from each cell are recovered and pooled to form an interacting gene library. This library can then be propagated by simple PCR amplification. Subsequently, one can interrogate this library for interactions of a gene of interest by designing a gene-specific primer, and using it in conjunction with a primer complementary to the opposite vector (see e.g. FIG. 2B or FIG. 8A).

Emulsion Conditions Optimization

It is necessary to have an emulsion that undergoes minimal lysis at the higher temperatures experienced during PCR. This may usually be accomplished by more vigorous stirring, making the aqueous droplets smaller and therefore less likely to merge. However, since the cells have a certain minimum size, and the droplets must also have space for the PCR reagents, a threshold is placed on how small the droplets can become. Ideally droplets should be no smaller than the largest size capable of thermal stability during PCR cycling. To determine the optimum conditions, two different oil phase compositions were tested, the CSR mix (Ghadessy et al., Proc Natl Acad Sci USA (2001) 98, 8, 4552-4557) used for a similar situation and a composition that contains twice the concentration of surfactants as the CSR mix (called 2×CSR mix). 400 µl of these compositions were placed in a NUNC Cryotube along with a small magnetic stirbar and 200 µl of aqueous phase was added. The two phases were mixed by stirring at ~550 rpm on a Corning PC-620D magnetic stirrer for 30, 60 and 120 seconds. Higher stirring is undesirable due to the formation of aqueous droplets that are of a very small size. The respective emulsions were aliquoted in 8 well strip tubes and subjected to PCR thermal cycling. The results are shown in FIG. 9A. It is clear that the 2×CSR mix, stirred at 550 rpm for about 120 seconds is optimal for the current application, as it is resistant to thermal lysis, and provides a sufficiently large droplet size (FIG. 9B, FIG. 9C). Nevertheless, a small amount of emulsion lysis does occur; this is countered by fractionating the emulsion as described above.

Proof-of-Concept Experiment

A primary requirement for this method to be useful is for inadvertent linkage of genes from different cells to be minimized. To test how well emulsification helps achieve this, a simple experiment consisting of two yeast strains, YC16_6 and YC16_14, was devised. 250,000 cells of each strain are added to the abovementioned SOE-PCR mix, immediately emulsified in the 2×CSR mix and subjected to the SOE-PCR protocol described above. The size of the SOE linked products from YC16_6 and YC16_14 are 1210 bp and 1350 bp. Mis-cognate SOE linkage of the pACT2 insert from YC16_6 and the pGBKT7 insert from YC16_14 leads to a product of 990 bp, while mis-cognate linkage of the YC16_14 pACT2 insert with the YC16_6 pGBKT7 insert gives a product of 1570 bp (FIG. 8B).

If the pACT2 and pGBKT7 inserts from YC16_6 and YC16_14 are linked in a cognate manner due to emulsification, the correct 1210 bp and 1350 bp bands should predominate over the incorrect 990 bp and 1570 bp bands. The result of the proof-of-concept experiment (FIG. 10A) is consistent with this prediction. While emulsified lanes have mostly the correct sized SOE bands, the non-emulsified control shows a very high concentration of the 990 bp band. The relative enrichment of the correct SOE bands may be judged by comparing the proportion of correct to incorrect bands in the emulsified vs. non-emulsified experiments. The extracted products from the emulsion PCR were further amplified using nested oligonucleotides. The secondary amplification was done in emulsion to prevent larger fragments being outcompeted by smaller ones (Ghadessy et al., 2001, supra). The results of this second PCR demonstrate that interactome libraries obtained by this method can be amplified without diminishing the percentage representation of larger SOE-linked products (FIG. 10B).

Threshold of Detection/Model Selection

Figure 12B:
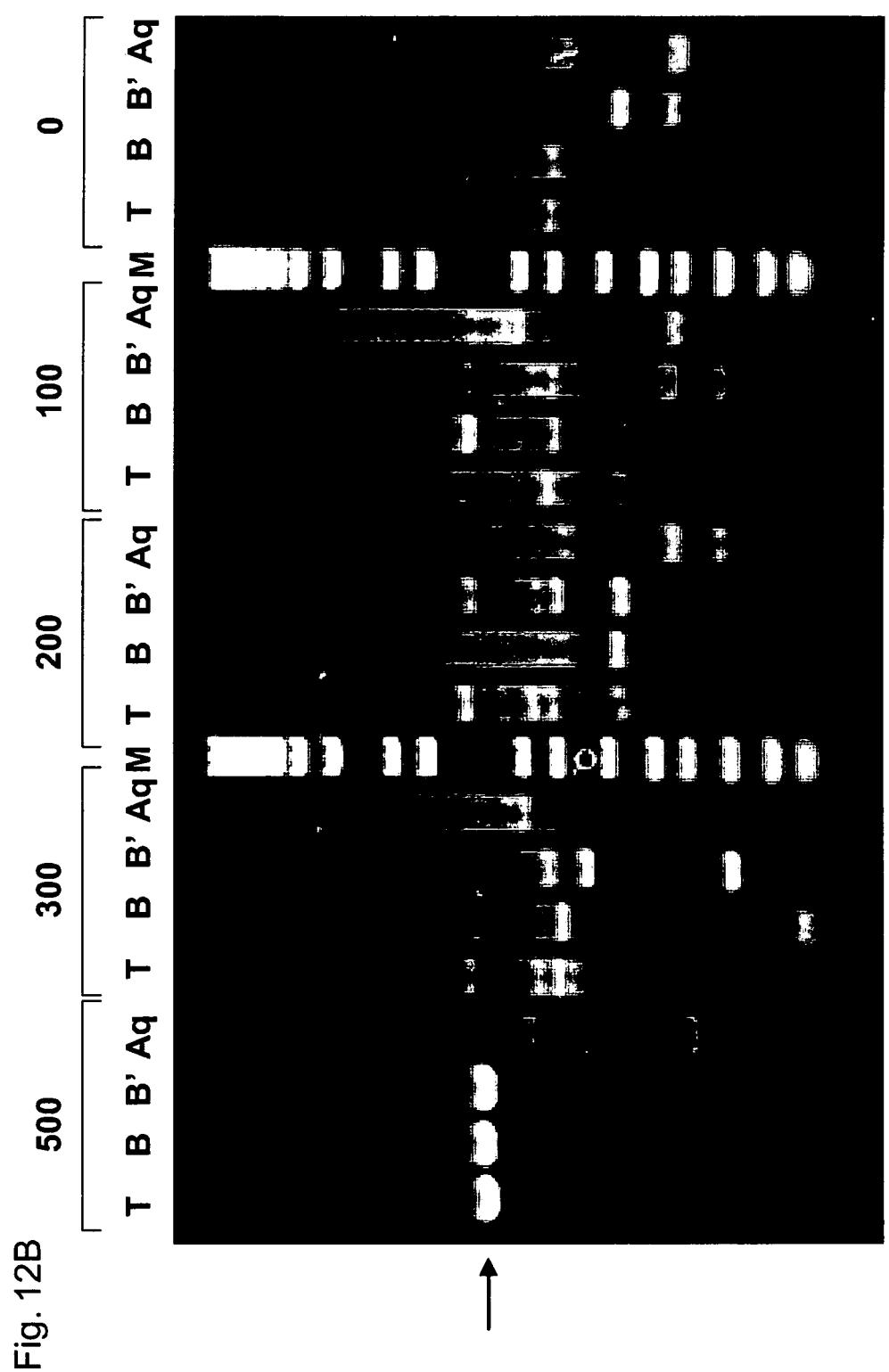

It is likely that a minimum number of cells representing each interaction will need to be present to reliably detect that interaction in subsequent secondary PCRs. This is owing to multiple causes, such as mis-priming on more abundant templates, a failure of some cells to be digested by lyticase, and presence of two cells in the same droplets. To detect what this threshold is, the following experiment was conducted: 1000, 100, 10 and 0 cells from a well characterized strain, YC8, carrying the human p53 gene on the pACT2 vector and the keratin 5 gene on a pGBK vector were mixed with 250,000 cells, each carrying both pACT2 and pGBK vectors containing random inserts, called the YC16 library, (to simulate a library of diverse interacting genes) and subjected to emulsion SOE-PCR as described above. After SOE-PCR, the emulsion were the extracted with ether, and 1 µl of the extract was used as a template for PCR with p53rev3, a primer specific to the p53 gene in YC8 and primer A, which is nested with respect Gal4ADF, used in the SOE PCR reaction (see e.g. FIG. 2 and FIG. 8 for schematic explanation). Whilst 1000 cells result in a clear product corresponding to a successful YC8 SOE-PCR (FIG. 12A), lower dilutions cannot be detected. Further analysis was carried out with 500, 300, 200 and 100 cells of YC8 diluted into 250,000 cells of the YC16 library. The results show that 500 target cells in a background of 250,000 library cells is the detection threshold (FIG. 12B).

Application to Bacterial Two-Hybrid System

Apart from the popular yeast two-hybrid system, two hybrid technologies exist in E. coli (Karimova, G, et al., Proc Natl Acad Sci USA (1998) 95, 10, 5752-5756) and mammalian systems (Lee, J W, & Lee, S K, Methods Mol Biol (2004) 261, 327-336; Fu, L, & Liang, J J, J Biol Chem (2002) 277, 6, 4255-4260; Luo, Y., et al., Biotechniques (1997) 22, 2, 350-352). Some groups have undertaken small scale bacterial two-hybrid experiments to discover limited interaction networks (Di Lallo, G., et al., Microbiology (2003) 149, Pt 12, 3353-3359; Maggi, S, et al., Microbiology (2008) 154, 10, 3042-3052; Marbouty, M., et al., J Bacteriol (2009) 191, 16, 5123-5133; Karimova, G, et al., J Bacteriol (2005) 187, 7, 2233-2243). To test whether E. coli two-hybrid is amenable to emulsion SOE-PCR, a simplified proof-of-concept experiment with two bacterial strains, BC165 and BC166 was carried out. Both strains contain two vectors, pet22b and pDsRed. BC165 contains a 600 bp Leukemia inhibitory factor (Lif) insert in the pet22b vector and a 180 bp c-fos fragment in the pDSRed vector. BC166 carries the vectors only, without any insert. petF2 and DsRev were used as the outer primers, while petRSOE and DsFSOE were the internal primers with complementary 5' ends. As with the yeast two-hybrid experiment, cognate SOE-PCR gave rise to 1150 bp and 480 bp bands from BC165 and BC166 respectively. Non-cognate SOE between the pet22b and DsRed amplicons of the two strains results in 1000 bp and 650 bp bands (see FIG. 7). 106 cells of each strain were added to a SOE-PCR mix and immediately emulsified and subjected to SOE-PCR as described above. The emulsion was fractionated into top, middle, bottom and lysed fractions and extracted using ether. A small amount of the extract was used as a template for PCR using nested oligonucleotides petF3 and DsR-rev. The secondary PCRs were run on an agarose gel (FIG. 7). The results clearly show that emulsion SOE-PCR preserves cognate pairing, resulting in a predominance of the correctly spliced products, whereas the aqueous control reaction leads to a stochastic distribution of the various SOE combinations. It is concluded that emulsion SOE-PCR technology can be extended to bacterial two-hybrid systems as well.

Discussion

The availability of genome sequence data has identified a large number of predicted proteins which are not functionally annotated and do not have reagents like antibodies directed against them. To rectify this situation, high throughput methods like library vs. library yeast two hybrid, combinatorial PCAs or yeast-phage display have been developed. However, the information that these techniques generate is in the form of cognate pairs of genes in cells or complementary yeast cells and phage. This information is not easily stored, replicated or disseminated. Also, sequencing large numbers of individual clones to transform interaction information from biological to digital form places a significant burden on most laboratories. Hastie and Pruitt (2007, supra) proposed a method that uses Cre recombinase and vectors carrying Cre recombination sites to physically link interacting genes into a single DNA sequence. The interaction information is therefore preserved even after the cells carrying the two genes are ruptured. Further they propose an innovative means of generating short sequence tags from the linked genes to lower the amount of sequencing required.

However, this method requires modification of existing strains, vectors and libraries and would be inapplicable to some high throughput methods like combinatorial yeast-phage display wherein the interacting pairs are not in the same cell (Bowley et al., 2009, supra). The iCLIP method we describe is completely in vitro and should be compatible with most current high throughput interaction detection techniques. Using this method we demonstrate the ability to link genes encoding interacting proteins. The interactome library size for current genome wide yeast two-hybrid ranges from ~1000 to about 4500 for yeast, and about 3000 for human interactome screens (Rual et al., 2005, supra; Stelzl et al, 2005, supra; Ito et al., 2001, supra; Uetz, et al., 2000, supra). It is thought that the total size of the interactome ranges from about 37000-75000 for yeast to almost 300,000 for humans (Rual et al., 2005, supra; Grigoriev, A, Nucleic Acids Res (2003) 31, 14, 4157-4161; Hart, G T, et al., Genome Biol (2006) 7, 11, 120). Based on the inventors' results, it can presently be assumed that each interaction should be represented by about 500 cells to ensure detectability (FIG. 3)—albeit further optimization may reveal a lower threshold value. For the total theoretical human interactome, this equals about $1.5 \times 10^8$ cells. Considering that 250,000 cells are processed in one iCLIP reaction, this number of cells will require about 600 reactions for complete coverage. The inventors' experience suggests that this is well within practical limits. Naturally, current screens which only encompass a small fraction of the full interactomes should be easily covered. At the same time, many improvements are desirable. The usage of automated emulsification machines (as for instance disclosed on www.raindancetechnologies.com) to create uniform and easily manipulated droplets should permit standardization and lower the amount of time required for processing a given interactome. This may also help to improve the sensitivity of the iCLIP process since the likelihood of cells being encapsulated in very small droplets is eliminated. Further refinements such as using bio-informatics tools to carefully design rescue primer sequences and modified high specificity oligos (Moreau, V, et al., Nucleic Acids Res (2009) 37, 19, e130) are contemplated.

It is interesting to speculate about novel technologies that might be enabled by our method. For instance, ribosome display is unrivalled in terms of library size and cycle time (Schaffitzel, C, et al., J Immunol Methods (1999) 231, 1-2, 119-135). It is tempting to visualize a very large library of genes expressed using ribosome display and the respective proteins allowed to interact. These interacting protein pairs could then be emulsified and the interaction captured using Reverse Transcription-SOE PCR. While some caveats such as concentration and kinetic limitations may apply to this suggestion, it seems like a promising avenue enabled by the method proposed by us. Displaying proteins on the surface of bacteria or phage and allowing interaction followed by emulsion SOE-PCR are possibilities along the same lines. Similarly, a library of small molecules tagged with unique oligonucleotide "barcodes" could be allowed to interact with mRNA or bacterial surface displayed proteins. Emulsification and SOE of these interacting pairs would allow the protein-small molecule interactome to be deciphered, forming a valuable resource for drug discovery.

The listing or discussion of a previously published document in this specification should not necessarily be taken as an acknowledgement that the document is part of the state of the art or is common general knowledge.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method of identifying a binding partner of at least one target molecule within a plurality of analyte molecules, wherein the target molecule is physically combined with a target labeling nucleic acid molecule, the target labeling nucleic acid molecule comprising a specific nucleotide sequence suitable for identifying the target molecule combined therewith, the method comprising:

contacting the target molecule with the plurality of analyte molecules, thereby forming a mixture,
wherein the binding partner is suspected to be a member of the plurality of analyte molecules, and wherein each member of the plurality of analyte molecules is physically combined with an analyte labeling nucleic acid molecule, each analyte labeling nucleic acid molecule comprising a selected nucleotide sequence suitable for identifying the analyte molecule combined therewith;

allowing the formation of a complex between the target molecule and the binding partner thereof within the mixture;

subdividing the mixture into a plurality of compartments, such that each compartment comprises at most about one member of the group consisting of:
(i) one target molecule, and
(ii) one complex between a target molecule and an analyte molecule;

thereby segregating a complex between a target molecule and an analyte molecule from the residual members of the plurality of analyte molecules;

allowing the target labeling nucleic acid molecule and the analyte labeling nucleic acid molecule to be linked, thereby forming a composite nucleic acid molecule;

allowing the plurality of compartments to disintegrate;

retrieving the composite nucleic acid molecule; and determining the sequence of the analyte labeling nucleic acid molecule, thereby identifying the binding partner of the target molecule.

2. The method of claim 1, wherein retrieving the composite nucleic acid molecule comprises at least one of:

(i) carrying out a primer based nucleic acid amplification using at least one primer that is complementary to a part of the sequence of the target labeling nucleic acid molecule, thereby amplifying the composite nucleic acid molecule; and (ii)
adding to the mixture a capture probe, the capture probe being capable of associating to the complex between the target molecule and the binding partner thereof, and retrieving the capture probe, thereby retrieving the complex between the target molecule and the binding partner thereof.

3. The method of claim 1, wherein subdividing the mixture into a plurality of compartments is carried out such that each compartment comprises at most about one member of the group consisting of:

(i) one target molecule,
(ii) one complex between a target molecule and an analyte molecule, and
(iii) one analyte molecule.

4. The method of claim 1, further comprising:
after subdividing the mixture into compartments releasing the physical combination between the analyte molecule defining the binding partner of the target molecule and the analyte labeling nucleic acid molecule combined therewith, thereby releasing the analyte labeling nucleic acid molecule.

5. A method of identifying a pair of a first and a second binding partner within a plurality of peptides and/or proteins, wherein the first and the second binding partners are capable of forming a complex, the method comprising:
providing a plurality of peptides and/or proteins, in a plurality of cells, wherein each member of the plurality of peptides and/or proteins is physically combined with a member encoding nucleic acid molecule, the member encoding nucleic acid molecule comprising a nucleotide sequence encoding the peptide or protein combined therewith;
subdividing the plurality of peptides and/or proteins in a plurality of cells, into compartments, such that each compartment comprises at most about one member or about one complex between members of the plurality of peptides and/or proteins in a plurality of cells,
thereby segregating a complex between the first and the second binding partner from the residual peptides and/or proteins;
allowing the member encoding nucleic acid molecule of the first binding partner and the member encoding nucleic acid molecule of the second binding partner to be linked,
thereby forming a composite nucleic acid molecule;
allowing the compartments to disintegrate;
retrieving the composite nucleic acid molecule; and
determining the sequence of the composite nucleic acid molecule, thereby identifying the first and/or the second binding partner.

6. The method of claim 5, wherein retrieving the composite nucleic acid molecule comprises:
carrying out a primer based nucleic acid amplification using a primer that is complementary to a part of the sequence of the member encoding nucleic acid molecule,
thereby amplifying the composite nucleic acid molecule.

7. The method of claim 5, wherein the composite nucleic acid molecule formed by a linkage of the member encoding nucleic acid molecule of the first binding partner and the member encoding nucleic acid molecule of the second binding partner is physically combined with the complex between the first and the second binding partner.

8. The method of claim 5, further comprising:
after subdividing the mixture into compartments releasing the physical combination between the member encoding nucleic acid molecules and the binding partners.

9. The method of claim 5, wherein the physical combination is a cell and wherein each member of the plurality of peptides and/or proteins is covalently linked to one of a first and a second complementing moiety,
wherein the first and the second complementing moiety, when brought into physical proximity, complement each other, thereby together defining a reporter factor.

10. The method of claim 9, wherein each member of the plurality of peptides and/or proteins and the complementing moiety are comprised in a fusion protein encoded by the member encoding nucleic acid molecule.

11. The method of claim 10, wherein the plurality of peptides and/or proteins is provided by expressing under suitable conditions a plurality of member encoding nucleic acid molecules in a plurality of cells, wherein each member encoding nucleic acid molecule encodes a single fusion protein, each fusion protein comprising one member of the plurality of peptides and/or proteins and one of the first and the second complementing moiety.

12. The method of claim 11, comprising allowing the expression of only one pair of a first and a second member encoding nucleic acid molecules in each of the plurality of cells, wherein the first nucleic acid molecule encodes a fusion protein having the first complementing moiety and the second nucleic acid molecule encodes a fusion protein having the second complementing moiety.

13. The method of claim 5, wherein the member encoding nucleic acid molecule of the first binding partner and the member encoding nucleic acid molecule of the second binding partner are allowed to be linked after the mixture is divided into compartments.

14. The method of claim 13, wherein the member encoding nucleic acid molecule of the first binding partner and the member encoding nucleic acid molecule of the second binding partner are allowed to be linked within a compartment obtained by subdividing the mixture into compartments.

15. The method of claim 5, wherein allowing the member encoding nucleic acid molecules to be linked comprises ligation of the nucleic acid molecules or overlap extension polymerase chain reaction.

16. A method of identifying a binding partner of a target peptide or protein within a plurality of peptides and/or proteins, wherein the target peptide or protein is comprised in a member of a first plurality of peptides and/or proteins and the binding partner is suspected to be comprised in a member of a second plurality of peptides and/or proteins, wherein each member of the first and the second plurality of peptides and/or proteins is physically combined with a member encoding nucleic acid molecule, the member encoding nucleic acid molecule comprising a nucleotide sequence encoding the peptide or protein combined therewith,
the method comprising:
combining the first and the second plurality of peptides and/or proteins, thereby forming a mixture;
allowing the formation of a complex between the target peptide or protein and the binding partner;
subdividing the mixture into compartments, such that each compartment comprises at most about one member or about one complex between members of the combined pluralities of peptides and/or proteins;
allowing the member encoding nucleic acid molecule of the target peptide or protein and the member encoding nucleic acid molecule of the binding partner of the formed complex to be linked,
thereby forming a composite nucleic acid molecule;
allowing the compartments to disintegrate;
retrieving the composite nucleic acid molecule; and
determining the sequence of the composite nucleic acid molecule, thereby identifying the binding partner.

17. The method of claim 16, wherein retrieving the composite nucleic acid molecule comprises one of:
(i) carrying out a primer based nucleic acid amplification using a primer that is complementary to a part of the sequence of the member encoding nucleic acid molecule encoding the target peptide or protein, thereby amplifying the composite nucleic acid molecule; and
(ii)
adding to the mixture a capture probe, the capture probe being capable of associating to the complex between the target peptide or protein and the binding partner thereof, and retrieving the capture probe, thereby retrieving the complex between the target peptide or protein and the binding partner thereof.

18. The method of claim 16, wherein the physical combination between the members of the first and of the second plurality of peptides and/or proteins is a cell and wherein each member of the first plurality of peptides and/or proteins is covalently linked to a first complementing moiety and each member of the second plurality of peptides and/or proteins is covalently linked to a second complementing moiety, wherein the first and the second complementing moiety, when brought into physical proximity, complement each other, thereby together defining a reporter factor.

19. The method of claim 16, wherein each member of the first plurality of peptides and/or proteins and the first complementing moiety are comprised in a fusion protein encoded by the member encoding nucleic acid molecule of the member of the first plurality of peptides and/or proteins.

20. The method of claim 16, wherein each member of the second plurality of peptides and/or proteins and the second complementing moiety are comprised in a fusion protein encoded by the member encoding nucleic acid molecule of the member of the second plurality of peptides and/or proteins.

21. The method of claim 20, wherein each member of the first plurality of peptides and/or proteins and the first complementing moiety are comprised in a fusion protein encoded by the member encoding nucleic acid molecule of the member of the first plurality of peptides and/or proteins, and each member of the second plurality of peptides and/or proteins and the second complementing moiety are comprised in a fusion protein encoded by the member encoding nucleic acid molecule of the member of the second plurality of peptides and/or proteins,
wherein said fusion proteins are provided by expressing under suitable conditions a plurality of member encoding nucleic acid molecules of the first plurality of peptides and/or proteins and a plurality of member encoding nucleic acid molecules of the second plurality of peptides and/or proteins.

22. The method of claim 21, comprising allowing the expression of only one pair of about one member encoding nucleic acid molecule of the first plurality of peptides and/or proteins and about one member encoding nucleic acid molecule of the second plurality of peptides and/or proteins in each of the plurality of cells.

23. A method of identifying one or more pairs of a first and a second binding partner within a plurality of peptides and/or proteins, wherein the first and the second binding partner are capable of forming a complex, the method comprising:
providing a library of nucleic acid molecules encoding a plurality of peptides and/or proteins, wherein the plurality of peptides and/or proteins is suspected to comprise the one or more pairs of a first and a second binding partner;
providing a plurality of members of a first vector and a plurality of members of a second vector, the first vector having a nucleic acid sequence encoding a first complementing moiety, the second vector having a nucleic acid sequence encoding a second complementing moiety, wherein the first and the second complementing moiety, when brought into physical proximity, complement each other, thereby together defining a reporter factor,
providing each member of the two pluralities of a first and of a second vector with one nucleic acid molecule of the library of nucleic acid molecules encoding the plurality of peptides and/or proteins,
introducing one of the members of the first vector and one of the members of the second vector into the same suitable cell, wherein both the first and the second vector each have one nucleic acid molecule encoding one of the plurality of peptides and/or proteins,
allowing in the cell the expression of the pair of peptides and/or proteins encoded by the nucleic acids provided with the vectors,
collecting any cell in which the formation of the reporter factor is detected,
subdividing individual collected cells in which the formation of the reporter factor is detected into compartments, such that each compartment comprises at most about one cell,
allowing in the compartments the member encoding nucleic acid molecule of the first binding partner and the member encoding nucleic acid molecule of the second binding partner to be linked,
thereby forming a composite nucleic acid molecule;
allowing the compartments to disintegrate;
retrieving the composite nucleic acid molecule; and
determining the sequence of the composite nucleic acid molecule, thereby identifying the first and/or the second binding partner.

24. The method of claim 23, wherein the first vector is a plasmid encoding the first complementing moiety, wherein the plurality of members of the first vector is a plurality of molecules of the first plasmid and wherein providing each member of the first vector with one nucleic acid molecule is inserting one nucleic acid molecule into each member of the pluralities of molecules of the first plasmid.

25. The method of claim 23, wherein the second vector is a plasmid encoding the second complementing moiety, wherein the plurality of members of the second vector is a plurality of molecules of the second plasmid and wherein providing each member of the second vector with one nucleic acid molecule is inserting one nucleic acid molecule into each member of the pluralities of molecules of the second plasmid.

26. The method of claim 23, wherein retrieving the comtposite nucleic acid molecule comprises at least one of:
(i) carrying out a primer based nucleic acid amplification using a primer that is complementary to a part of the sequence of the member encoding nucleic acid molecule of the first binding partner,
thereby amplifying the composite nucleic acid molecule; and
(ii) adding to the mixture a capture probe, the capture probe being capable of associating to the complex between the first and a second binding partner, and
retrieving the capture probe, thereby retrieving the complex between the first and a second binding partner.

27. A method of identifying a binding partner of at least one target peptide or protein within a plurality of analyte peptides and/or proteins, wherein the target peptide or protein and the binding partner thereof are capable of forming a complex, the method comprising:
providing a library of nucleic acid molecules encoding the plurality of analyte peptides and/or proteins, wherein the plurality of peptides and/or proteins is suspected to comprise a binding partner of the at least one target peptide or protein;
providing at least one nucleic acid molecule encoding the at least one target peptide or protein;
providing a plurality of members of a first vector and a plurality of members of a second vector, the first vector having a nucleic acid sequence encoding a first complementing moiety, the second vector having a nucleic acid sequence encoding a second complementing moiety, wherein the first and the second complementing moiety, when brought into physical proximity, complement each other, thereby together defining a reporter factor, providing each member of the plurality of members of the first vector with one nucleic acid molecule of the library of nucleic acid molecules encoding the plurality of analyte peptides and/or proteins, providing each member of the plurality of molecules of the second vector with one nucleic acid molecule of the at least one nucleic acid molecule encoding the at least one target peptide or protein, introducing one of the members of the first vector and one of the members of the second vector into the same suitable cell, allowing in the cell the expression of the pair of peptides and/or proteins encoded by the nucleic acids provided with the vectors, collecting any cell in which the formation of the reporter factor is detected, subdividing individual collected cells in which the formation of the reporter factor is detected into compartments, such that each compartment comprises at most about one cell, allowing in the compartments the member encoding nucleic acid molecule of the first binding partner and the member encoding nucleic acid molecule of the second binding partner to be linked, thereby forming a composite nucleic acid molecule;

allowing the compartments to disintegrate;

retrieving the composite nucleic acid molecule; and determining the sequence of the composite nucleic acid molecule, thereby identifying the binding partner of the target peptide or protein.

28. The method of claim 27, wherein the first vector is a plasmid encoding the first complementing moiety, wherein the plurality of members of the first vector is a plurality of molecules of the first plasmid and wherein providing each member of the first vector with one nucleic acid molecule is inserting one nucleic acid molecule into each member of the pluralities of molecules of the first plasmid.

29. The method of claim 27, wherein the second vector is a plasmid encoding the second complementing moiety, wherein the plurality of members of the second vector is a plurality of molecules of the second plasmid and wherein providing each member of the second vector with one nucleic acid molecule is inserting one nucleic acid molecule into each member of the pluralities of molecules of the second plasmid.

30. The method of claim 27, wherein retrieving the composite nucleic acid molecule comprises at least one of:
(i) carrying out a primer based nucleic acid amplification using a primer that is complementary to a part of the sequence of the nucleic acid molecule encoding the target peptide or protein,
thereby amplifying the composite nucleic acid molecule; and
(ii) adding to the mixture a capture probe, the capture probe being capable of associating to the complex between the target peptide or protein and the binding partner thereof, and
retrieving the capture probe, thereby retrieving the complex between the target peptide or protein and the binding partner thereof.

31. The method of claim 27, being a method of identifying a binding partner of at least two target molecules within a plurality of analyte peptides and/or proteins, wherein providing at least one nucleic acid molecule encoding the at least one target peptide or protein is carried out by providing at least two nucleic acid molecules, each nucleic acid molecule encoding one of the at least two target peptides or proteins.

* * * * *